(12) United States Patent
Kolb et al.

(10) Patent No.: US 7,928,210 B2
(45) Date of Patent: Apr. 19, 2011

(54) NUCLEOSIDE BASED PROLIFERATION IMAGING MARKERS

(75) Inventors: Hartmuth C. Kolb, Playa Del Rey, CA (US); Joseph C. Walsh, Pacific Palisades, CA (US); Robert M Yeh, Culver City, CA (US); Kai Chen, Los Angeles, CA (US); Umesh Gangadharmath, Los Angeles, CA (US); Brian Duclos, Los Angeles, CA (US); Vani P. Mocharla, Los Angeles, CA (US); Farhad Karimi, Canton, MA (US); Henry C. Padgett, Hermosa Beach, CA (US); Qianwa Liang, Hacienda Heights, CA (US); Tieming Zhao, Los Angeles, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 503 days.

(21) Appl. No.: 12/074,538

(22) Filed: Mar. 3, 2008

(65) Prior Publication Data

US 2009/0016958 A1    Jan. 15, 2009

Related U.S. Application Data

(60) Provisional application No. 60/904,223, filed on Mar. 1, 2007.

(51) Int. Cl.
*C07H 21/02* (2006.01)
*C07H 21/04* (2006.01)

(52) U.S. Cl. .............. 536/23.1; 536/25.3; 536/25.32; 536/27.1; 536/27.13; 536/28.1

(58) Field of Classification Search .................. None
See application file for complete search history.

(56) References Cited

FOREIGN PATENT DOCUMENTS

| | | |
|---|---|---|
| EP | 0417999 | 3/1991 |
| EP | 1270017 | 1/2003 |
| JP | 2007126412 A | 5/2007 |
| WO | WO 88/07986 | 10/1988 |
| WO | WO 9700089 | 1/1997 |
| WO | WO 9707829 | 3/1997 |
| WO | WO 99/44646 | 9/1999 |
| WO | WO 0105439 A1 | 1/2001 |
| WO | WO 03/099840 | 12/2003 |
| WO | WO 03099342 A1 | 12/2003 |
| WO | WO 2004087139 | 10/2004 |
| WO | WO 2004096138 A2 | 11/2004 |
| WO | WO 2005/020885 | 3/2005 |
| WO | WO 2005044312 A1 | 5/2005 |
| WO | WO 2008024826 A2 | 2/2008 |
| WO | WO 2008049644 A1 | 5/2008 |

OTHER PUBLICATIONS

Dai et al: Regioselective arylation of 2'-deoxyribonucleosides on amido or imino sited by copper (II)-mediated direct coupling with arylboronic acids Tetrahedron Elservier Science Publishers, Amsterdam, NL, vol. 62, No, 8, Feb. 20, 2006, pp. 1764-1771, XP005269250 ISSN: 0040-4020 Compounds dG, 1b, lo-lq.
Ikehara M et al: "Studies on Nucleosides and Nucleotides.LXXXIX. Purine Cyclonucleosides. (43) Syntheses and Porperties of 2'-Halogeno-2'-deoxyguanosines" Chemical and Pharmaceutical Bulletin, Pharmaceutical Society of Japan, Tokyo, vol. 29, No. 11 Jan. 1, 1981, pp. 3281-3285, XP002980857 ISSN: 0009-2363 Compounds IVa-d.
Zavgorodny S et al,: "1-Alkylthioalkylation of nucleoside hydroxyl functions and its synthetic applications: a new versatile method in nucleoside chemistry" Tetrahedron Letters, Elsevier, Amsterdam, vol. 32, No. 51, Jan. 1, 1991, pp. 7593-7596, XP002200270 ISSN: 0040-4039 Compound 5.
Namavari M et al: "Synthesis of 8-[<18>F] flouroguanine derivatives: in vivo probes for imaging gene expression with positron emission tomography" Nuclear Medicine and Biology, Elsevier, NY, US vol. 27, No. 2, Feb. 1, 2000, pp. 157-162, XP004196583 ISSN: 0969-8051 Compound 3d.
Lee Y W., et al., "Tumor Uptake of Radiolabelled Pyrimidine Bases and Pyrimidine Nucleosides in Animal Models: VI. 1-(3'-[36C1]-Chloro-, 1-(3'[82Br]-Bromo- and 1-(3'-[123I]-Iodo-3'-Deoxy-Beta-D-Arabinofuranosyi)uraci", International Journal of Applied Radiation and Isotops, Pergamon Press,, New York, NY, US, vol. 35, No. 11, Nov. 1, 1984 (pp. 1057-1061).
Alauddin Mian M., et al., "Synthesis of [18F]-Labeled N-3(Substituted) Thymidine Analogues: N-3([18F]Fluorobutyl) Thymidine ([18F]-FBT) and N-3([18F]Fluoropentyl)Thymidine ([18F]-FPT) for PET", Journal of Labelled Compounds and Radiopharmaceuticals, vol. 49, No. 12, Oct. 2006 (pp. 1079-1088).
Wagner M., et al., "3'-[18F]Fluoro-3'-Deoxythymidine ([18F]-FLT) As Positron Emission Tomography Tracer for Imaging Proliferation in a Murine B-Cell Lymphoma Model and in the Human Disease", Cancer Research, American Association for Cancer Research, Baltimore, MD, US, vol. 63, No. 10, May 15, 2003 (pp. 2681-2687).
Kang Se Hun, et al., "Simple and High Radiochemical Yield Synthesis of 2'-Deoxy-2'[18F]Fluorouridine Via a New Nosylate Precursor", Journal of Labelled Compounds and Radiopharmaceuticals, vol. 49, No. 14, Dec. 2006 (pp. 1237-1246).
Alauddin Mian M., et al., "A General Synthesis of 2'-Deoxy-2'-[18]Fluoro-1-Beta-D-Arabinofuranosyluracil and its 5-Substituted Nucleosides", Journal of Labelled Compounds and Radiopharmaceuticals, vol. 46, No. 4, Mar. 30, 2003 (pp. 285-289).
Ghosh Pradip, et al., "N3-Substituted Thymidine Analogues III: Radiosynthesis of N3-[(4-[18F]Fluoromethyl-Phenyl)Butyl]Thymidine ([18F]-FMPBT) and N3[(4-[18F]Fluoromethyl-Phenyl)Pentyl] Thymidine ([18F]-FMPPT) for PET", Journal of Labelled Compounds and Radiopharmaceuticals, vol. 50, No. 13-14, Nov. 2007 (pp. 1185-1191).

(Continued)

*Primary Examiner* — Patrick T Lewis
(74) *Attorney, Agent, or Firm* — Joshua B. Ryan

(57) ABSTRACT

Disclosed herein are novel radiolabeled nucleosides and methods for detecting cellular proliferation in a mammal, the method comprising administrating an effective amount of a radiolabeled nucleoside; the method comprising: a) administering to the mammal a diagnostically effective amount of the nucleoside to the mammal; b) allowing the nucleoside to distribute into the effective tissue; and c) imaging the tissue, wherein an increase in binding of the compound to tissue compared to a normal control level of binding indicates that the mammal is suffering from a disease involving cellular proliferation.

31 Claims, 6 Drawing Sheets

OTHER PUBLICATIONS

Simon, et al., "An Efficient F-18 Labeling Method for PET Study: Huisgen 1,3-Dipolar Cycloaddition of Bioactive Substances and F-18-Labeled Compounds", Tetrahedron Letters, Elsevier, Amsterdam, vol. 48, No. 23, Jun. 4, 2007 (pp. 3953-3957).

Anthony F. Shields, "Positron Emission Tomography: 24. Labeled Pyrimidines in PET Imaging", 2006, Springer, Peter E. Valk, Dominique Delbeke, Dale L. Baily, David W. Townsend and Michael N. Maisey, London (pp. 375-385).

Balzarini, et al. "The effect of a methyl or 2-fluoroethyl substituent at the N-3 position of thymidine, 3'-fluoro-3'-deoxythymidine and 1-beta-D-arabinosylthymine on their antiviral and cytostatic activity in cell culture." Antiviral Chemistry & Chemotherapy (2006), 17:17-23.

Robins, et al. Nucleic acid related compounds. 42. A general procedure for the efficient deoxygenation of secondary alcohols. Regiospecific and stereoselective conversion of ribonucleosides to 2'-deoxynucleosides. J. Am. Chem. Soc. (1983), 105(12):4059-4065.

Schinazi, et al. "Antiviral and antineoplastic activities of pyrimidine arabinosyl nucleosides and their 5'- amino derivatives." J. Med. Chem. (1979), 22(10):1273-1277.

Toyohara, et al. "Alkyl-fluorinated thymidine derivatives for imaging cell proliferation I. The in-vitro evaluation of some alkyl-fluorinated thymidine derivatives." Nuclear Medicine and Biology (2006), 33:751-764.

Toyohara, et al. "Alkyl-fluorinated thymidine derivatives for imaging cell proliferation II. Synthesis and evaluation of N3-(2-[18F]fluoroethyl)-thymidine." Nuclear Medicine and Biology (2006), 33:765-772.

Schwartz, et al., "Evaluation of 5'-deoxy-5'-[F-18] fluorothymidine as a tracer of intracellular thymidine phosphorylase activity", Nuclear Medicine and Biology 34 (2007) 471-478.

NUCLEOSIDE BASED PROLIFERATION IMAGING MARKERS

CROSS-REFERENCE TO RELATED APPLICATIONS

This application claims priority to U.S. Provisional Application No. 60/904,223, filed Mar. 1, 2007.

The present invention relates to radioactively labeled nucleoside analogs substituted at the 3-N, 3'-O and 2'-O positions with various linkers useful for modifying their in vivo pharmacokinetics. In one embodiment, the nucleoside analogs are thymidine analogs. These compounds display high cellular uptake and phosphorylation rates, undergo facile radiolabeling and display favorable tumor to background uptake ratios. Preferred compounds localize within tumors having high populations of cells in the S-phase. Preferred compounds can be used to detect rapidly proliferating cells in vivo and thus identify patients with diseases marked by abnormally proliferating cells such as cancer. Additionally, these analogs may be used as surrogate markers to monitor efficacy of therapy.

BACKGROUND OF THE INVENTION

PET, being a molecular imaging technology, detects a myriad of diseases non-invasively. PET imaging systems create images based on the distribution of positron-emitting isotopes in the tissue of a patient. The isotopes are typically administered to a patient by injection of probe molecules that comprise a positron-emitting isotope, such as F-18, C-11, N-13, or O-15, covalently attached to a molecule that metabolizes or localizes in the body (e.g., glucose) or that binds to receptor sites within the body. In some cases, the isotope is administered to the patient as an ionic solution or by inhalation. Clinicians employ PET to accurately detect, stage, and restage cancer in patients. One of the most widely used positron-emitter labeled PET molecular imaging probes is 2-deoxy-2-[$^{18}$F]fluoro-D-glucose ([$^{18}$F]FDG). Because early changes in glucose utilization have been shown to correlate with outcome predictions, clinicians use PET-FDC imaging to monitor cancer chemo- and radiotherapy. Other molecularly targeted PET imaging tracers are being developed to image other enzyme-mediated transformations in cancer tissue. Ongoing research efforts are directed at identifying additional biomarkers that show a very high affinity to and specificity for, tumor targets to support cancer drug development and to provide health care providers with a means to accurately diagnose disease and monitor treatment. Such imaging probes can dramatically improve the apparent spatial resolution of the PET scanner, allowing smaller tumors to be detected, and nanomole quantities to be injected in patients.

While the clinical use of PET for detecting cancer is growing, FDG based imaging does have limitations. Accumulation in inflammatory tissue limits the specificity of FDG-PET. Conversely, nonspecific FDG uptake may also limit the sensitivity of PET for tumor response prediction. Therapy induced cellular stress reactions have been shown to cause a temporary increase in EDG-uptake in tumor cell lines treated by radiotherapy and chemotherapeutic drugs. Further, physiological high normal background activity (i.e., in the brain) can render the quantification of cancer-related FDG-uptake impossible in some areas of the body. Ongoing research efforts are directed to identifying additional biomarkers that show a very high affinity to, and specificity for, tumor targets to support cancer drug development and to provide health care providers with a means to accurately diagnose disease and monitor treatment. Such imaging probes can dramatically improve the apparent spatial resolution of the PET scanner, allowing smaller tumors to be detected, and nanomole quantities to be injected in patients. A promising area for the development of these new agents focuses on imaging the enzymes associated with cellular proliferation. More specifically, new PET imaging agents that mimic the natural nucleoside thymidine offer the opportunity to directly observe the enzymatic pathways associated with thymidine metabolism and cell proliferation.

The nucleoside thymidine (FIG. 1) fulfills a vital role in cell growth via its participation in DNA replication and cell division. The cellular recruitment and utilization of thymidine occurs via discreet pathways. Nucleoside transporters ENT1 and/or CNT1 shuttle thymidine from the extracellular matrix into cells. In certain cancer cells, nucleoside transporter expression increases several fold to meet the demand for DNA synthesis and thymidine utilization. Once inside the cell, human thymidine kinase-1 (hTK-1) metabolizes thymidine into its 5'-O-monophosphate derivative, preparing it for incorporation into the growing DNA chain. The rate of thymidine metabolism varies depending on the stage of cell growth. In the resting phase, the consumption and incorporation of thymidine by the cell slows as DNA replication also slows. However, in the waking phase, or S phase, over-expression of hTK-1 is needed to metabolize the larger quantity of thymidine transported across the cell membrane.

Proliferating cancer cells increase their demand for thymidine by up-regulating both nucleoside transporters and hTK-1. The difference in thymidine uptake between cancer cells and normal cells translates into preferential imaging of the metabolic fate of thymine analogs in cancer cells in the presence of normal cells. Thus, radiotracers undergo transport across the cellular membrane, although the specific mechanism of action of this transport remains unknown, followed by 5'-O-phosphorylation metabolism by thymidine kinase. The metabolizing phosphorylation step effectively traps the tracer intracellularly and preferential accumulation of the tracer builds within cancer cells. This targeted accumulation leads to visualization of cancer cells in the presence of normal cells.

The fluorinated analog of thymidine 3'-[8F]Fluoro-3'-deoxythymidine (FLT), FIG. 2, successfully visualizes thymidine kinase activity in vivo. Non-radioactive FLT was originally developed as an antiviral then as a potential therapeutic for HIV; however, its toxicity profile prevented its therapeutic use. Fortunately, radiolabeled FLT showed promise as an imaging agent for detecting cancer. Radiolabeled FLT uptake by cancer cells correlates well with tumor proliferation and can be used to monitor response to therapy. Clinicians use radiolabeled FLT to assist in detecting and staging lung tumors and brain gliomas. More specifically, FLT imaging can characterize malignant from benign tumors and determine proliferation rates of lung tumors. For use in detecting and staging non-small cell lung cancers, FLT may provide additional information regarding the risk of recurrence after resection.

FLT successfully mimics thymidine recruitment and metabolism in vivo, although there are exceptions. For instance, while hTK-1 recognizes FLT as a substrate, mitochondrial thymidine kinase-2 (TK-2) does not and metabolizes FLT poorly. This serendipitous selectivity aids the detection of hTK-1 activity in vivo even in the presence of low levels of mitochondrial TK-2 expression. FLT also displays a favorable metabolic profile relative to another DNA proliferation marker, $^{11}$C-thymidine. Unlike the rapid catabolism of phosphorylated $^{11}$C-thymidine into various metabolites, FLT-phosphate resists thymidine phosphorylase catabolism. This metabolic stability simplifies the interpretation of PET images as there are fewer metabolites present. $^{11}$C-thymidine based PET imaging requires complicated mathematical models for image interpretation to compensate for $^{11}$C-thymidine derived metabolites. FLT exhibits a fairly typical biodistribution pattern: it localizes in the bladder and kidneys, which excrete undegraded FLT. However, the liver retains FLT although mainly as the glucoronidated species. FLT also distributes amongst haematopoietic bone marrow, a site of high cellular proliferation. On average, the injected dose per gram of FLT in tumors is 5%.

Despite the clinical success of FLT, imaging with FLT does have certain drawbacks. First, and most importantly, FLT uptake in tumors consistently remains lower than FDG uptake. This low tumor uptake has made imaging difficult because of the low signal to noise ratios. Additionally, the high hepatic retention of FLT prevents accurate imaging of tumors and metastases near the liver thus limiting the utility of FLT in the clinical setting.

FMAU (FIG. 3) is another nucleoside analog that has shown promise as a proliferative marker. While its uptake in cancer cells appears promising, the multistep radiosynthetic method for preparing this molecule severely limits its use as a standard clinical biomarker.

Previous work by Eriksson and coworkers offered the initial direction towards designing new thymidine-based imaging agents. They discovered that 3-N boronated thymidine analogs containing large closo-carboranylalkyl groups served as boron neutron capture therapy agents (FIG. 4). In addition to using the boron cage as a sink for incoming neutrons, several pharmacokinetic benefits happen to make these thymidine analogs more successful than anticipated. First, the boron group adds sufficient lipophilicity thus aiding in its transport across cell membranes. Secondly, because of the steric bulk at the 3-N position, these boronated compounds remained substrates for hTK-1 but not hTK-2. These results confirm the finding that hTK-1 tolerates bulky substituents preferentially over TK-2. These compounds are also taken up and retained by hTK-1 expressing cells in vitro but not retained in non-TK-1 expressing cells. While these carboranylated thymidines cannot be used directly for PET imaging, they do provide insight into other thymidine analogs that may image hTK-1 activity in vivo.

SUMMARY OF THE INVENTION

Accordingly, new thymidine analogs that may be useful for imaging cell proliferation in vivo should provide improved pharmacokinetic profiles, such as a higher % ID/g, leading to stronger signal to noise ratios. An increase in % ID/g may result from thymidine analogs having higher intracellular phosphorylation rates relative to FLT. Radiolabeled derivatives of thymidine that preserve the 3'-hydroxy group may undergo higher rates of phosphorylation relative to FLT because hTK-1 phosphorylates thymidine faster than FLT. If these derivatives are transported into the cells and are phosphorylated faster than FLT, this may lead to higher signal to noise ratios in vivo and, ultimately, to more sensitive detection of proliferating cells. This technology may provide clinicians with the means necessary to more accurately stage tumors, predict a response to therapy and monitor efficacy of therapy.

In one embodiment, the present invention relates to novel radioactively labeled nucleoside analogs, such as thymidine analogs, that are useful for detecting elevated cellular proliferation in vivo using positron emission tomography (PET). In one embodiment, the nucleoside analogs are represented in FIG. 5. In another embodiment, the nucleoside analogs are the thymidine analogs. The unique series of analogs of the present application exhibit a higher cellular uptake in proliferating cancer cells and a higher formation of the 5'-O-phosphorylated metabolite relative to FLT. In addition to their elevated cell uptake and phosphorylation rates, these analogs display favorable tumor to background ratios necessary for successful imaging procedures, such as by PET imaging.

In one embodiment, the structural components of these novel nucleoside analogs, include the base scaffold and a novel linker. In one variation, the structural components of thymidine scaffold and a linker that are useful for modifying the pharmacokinetic profile in vivo and a radioactive isotope such as [$^{18}$F]-fluorine or [$^{11}$C]-carbon. In one embodiment, the nucleoside analogs are the thymidine analogs. These analogs may be used for identifying patients having an abnormal population and localization of cells in the S-phase, a biomarker related to cancer. As used herein, the biomarker is a measurable characteristic that predicts a clinical endpoint for measuring or monitoring a disease. A "surrogate marker" is a biomarker that substitutes for a clinical endpoint. In one aspect, the surrogate marker is a specific case of a biomarker. That is, the surrogate marker is not simply a predictor of a clinical endpoint but may be used as a reliable substitute for a clinical endpoint. The present compositions and methods of using the composition of the present application provide data that validate the use of the method as effective surrogate markers. An example of a clinical endpoint is the assessment of a therapeutic's clinical efficacy.

In another aspect of the invention, these compounds may also be used as surrogate markers to monitor the efficacy of therapeutic treatment of cancer.

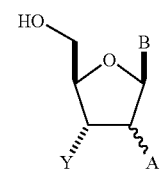

1 wherein the variables A, Y, R$^2$, R$^3$ and R$^4$ are as defined herein and

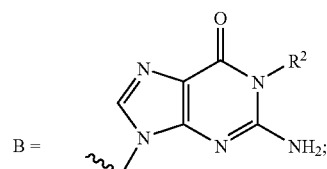

B1

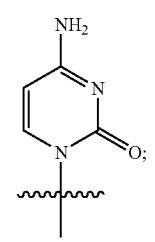

B2

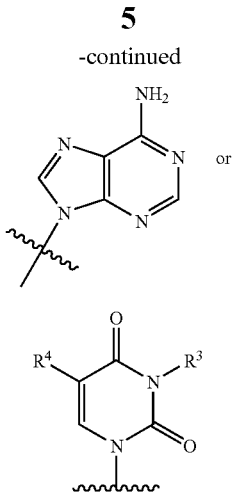

In addition to the exemplary embodiments, aspects and variations described above, further embodiments, aspects and variations will become apparent by reference to the drawings and figures and by examination of the following descriptions.

DETAILED DESCRIPTION OF THE INVENTION

Figure 1:
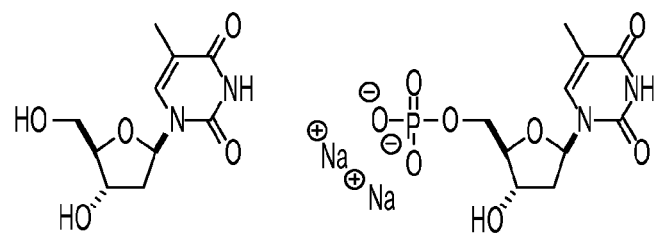
FIG. 1 shows the structure of thymidine and thymidine 5'-O-monophosphate.
Figure 2:
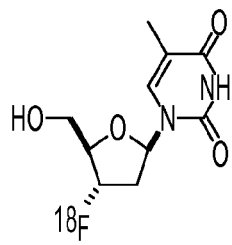
FIG. 2 shows the structure of 3'-[$^{18}$F]fluoro-3'-deoxythymidine (FLT).
Figure 3:
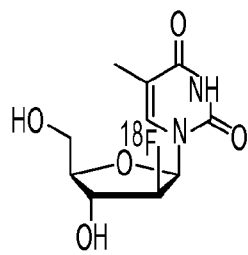
FIG. 3 shows the structure of 1-(2'-deoxy-2'-[$^{18}$F]fluoro-β-D-arabinofuranosyl)-5-methyluracil (FMAU).
Figure 4:
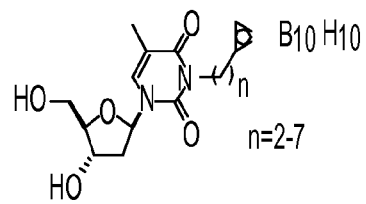
FIG. 4 shows the structure of 3-N boronated thymidine (Eriksson et al).
Figure 5:
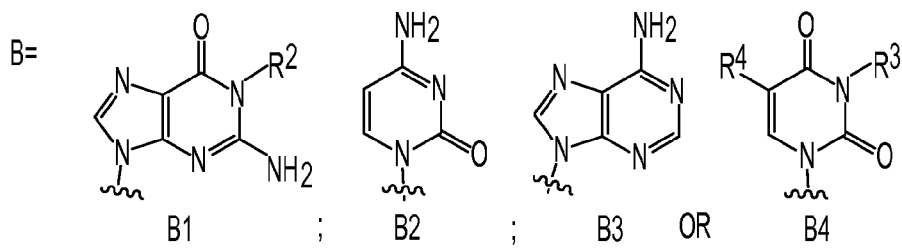
FIG. 5 shows the structure of nucleoside analogs.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. Unless specifically noted otherwise herein, the definitions of the terms used are standard definitions used in the art of organic synthesis and pharmaceutical sciences. Exemplary embodiments, aspects and variations are illustrated in the figures and drawings, and it is intended that the embodiments, aspects and variations, and the figures and drawings disclosed herein are to be considered illustrative and not limiting.

As used herein, the singular forms "a", "an", "the", include plural referents unless the context clearly dictates otherwise.

"Halogen" or "halo" means F, Cl, Br and I.

"Alkyl" means a saturated monovalent hydrocarbon radical having straight or branched moieties. Examples of alkyl groups include, but are not limited to, methyl, ethyl, n-propyl, isopropyl and t-butyl.

"Alkenyl" means an alkyl moieties having at least one carbon-carbon double bond wherein alkyl is as defined above. Examples of alkenyl include, but are not limited to, ethenyl and propenyl.

"Alkynyl" means alkyl moieties having at least one carbon-carbon triple bond wherein alkyl is as defined above. Examples of alkynyl groups include, but are not limited to, ethynyl and 2-propynyl.

"Alkylene" or "alkylenyl" means a saturated, divalent hydrocarbon radicals i.e., generally present as a bridging or linking group between two other groups, having straight or branched moieties. Examples of alkylene groups include —CH$_2$-(methylene); —CH$_2$CH$_2$-(ethylene); —CH$_2$CH$_2$CH$_2$-(propylene), —CH(CH$_3$)CH$_2$-(isopropylene) etc."

"Amino" means a nitrogen moiety having two further substituents where a hydrogen or carbon atom is attached to the nitrogen. For example, representative amino groups include —NH$_2$, —NHCH$_3$, —N(CH$_3$)$_2$, —NHC$_{2-3}$-alkyl, —N(C$_{2-3}$-alkyl)$_2$ and the like. Unless indicated otherwise, the compounds of the invention containing amino moieties may include protected derivatives thereof. Suitable protecting groups for amino moieties include acetyl, tert-butoxycarbonyl, benzyloxycarbonyl and the like.

"Aryl" means an organic radical derived from an aromatic hydrocarbon by removal of one hydrogen, such as phenyl, naphthyl, indenyl, indanyl and fluorenyl. "Aryl" encompasses fused ring groups wherein at least one ring is aromatic.

"Arylene" or "arylenyl" means an organic radical derived from an aromatic divalent radical by removal of at least two hydrogens, from a group such as phenyl, naphthyl, indenyl, indanyl and fluorenyl. An arylene is generally present as a bridging or linking group between two other groups. Non-exclusive examples of such arylene groups include 1,3-disubstituted phenyl, 1,4-disubstituted phenyl, etc.

A "biological target" can be any biological molecule involved in biological pathways associated with any of various diseases and conditions, including cancer (e.g., leukemia, lymphomas, brain tumors, breast cancer, lung cancer, prostate cancer, gastric cancer, as well as skin cancer, bladder cancer, bone cancer, cervical cancer, colon cancer, esophageal cancer, eye cancer, gallbladder cancer, liver cancer, kidney cancer, laryngeal cancer, oral cancer, ovarian cancer, pancreatic cancer, penile cancer, glandular tumors, rectal cancer, small intestine cancer, sarcoma, testicular cancer, urethral cancer, uterine cancer, and vaginal cancer), diabetes, neurodegenerative diseases, cardiovascular diseases, respiratory diseases, digestive system diseases, infectious diseases, inflammatory diseases, autoimmune diseases, and the like. Exemplary biological pathways include, for example, cell cycle regulation (e.g., cellular proliferation and apoptosis), angiogenesis, signaling pathways, tumor suppressor pathways, inflammation (COX-2), oncogenes, and growth factor receptors. The biological target may also be referred to as the "target biomacromolecule" or the "biomacromolecule." The biological target can be a receptor, such as enzyme receptors, ligand-gated ion channels, G-protein-coupled receptors, and transcription factors. The biologically target is preferably a protein or protein complex, such as enzymes, membrane transport proteins, hormones, and antibodies.

"Cycloalkyl" means non-aromatic saturated cyclic alkyl moieties consisting of one or more rings, wherein said rings (if more than one) share at least one carbon atom, wherein alkyl is as defined above. Examples of cycloalkyl include, but are not limited to, cyclopropyl, cyclobutyl, cyclopentyl, cyclohexyl, cycloheptyl, bicyclo-[3.1.0]-hexyl, bicyclo-[2.2.1]-hept-1-yl, norbornyl, spiro[4.5]decyl, spiro[4.4] nonyl, spiro[4.3]octyl, spiro[4.2]heptyl and adamantanyl.

"HaloC$_{1-4}$alkyl" or "HaloC$_{1-6}$alkyl" for example, means a C$_{1-4}$alkyl or C$_{1-6}$alkyl group that is substituted with at least one halogen atom on a carbon atom of the alkyl group. Non-exclusive, representative examples of such haloC$_{1-6}$alkyl include F—CH$_2$—, F—CH$_2$CH$_2$—, F—CH$_2$CH$_2$CH$_2$—, CHF$_2$—, CHF$_2$CH$_2$—, CHF$_2$CH$_2$CH$_2$—, Br—CH$_2$—, Br—CH$_2$CH$_2$—, Br—CH$_2$CH$_2$CH$_2$—, CHBr$_2$—, CHBr$_2$CH$_2$—, CHBr$_2$CH$_2$CH$_2$— and the like.

"Heterocyclic" or "heterocycloalkyl" means a non-aromatic cyclic groups consisting of one or more rings, wherein the rings (if more than one) share one or two atoms and each ring contains up to four heteroatoms (i.e. from zero to four heteroatoms, provided that at least one ring contains at least one heteroatom). The heterocyclic groups of this invention can also include ring systems substituted with one or more O, S(O)$_{0-2}$, and/or N—R$^{10}$ as heteroatoms, wherein R$^{10}$ is as defined herein, and wherein the subscript "0-2" of S(O)$_{0-2}$ represents an integer of 0, 1 or 2. Thus, S(O)$_2$ represents the group consisting of S, S(=O), and S(O)$_2$. Examples of non-aromatic heterocyclic groups are aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo [3.1.0]hexanyl, 3-azabicyclo[4.1.0]heptanyl, quinolizinyl, quinuclidinyl, 1,4-dioxaspiro[4.5]decyl, 1,4-dioxaspiro[4.4] nonyl, 1,4-dioxaspiro[4.3]octyl and 1,4-dioxaspiro[4.2]heptyl.

"Heteroaryl" means an aromatic group containing one or more heteroatoms (O, S, or N), preferably from one to four heteroatoms. In certain variation, for example, the heteroaryl may be optionally substituted as provided herein. Such substitution may include a halo group, such as fluoro. A heteroaryl may be a monocyclic or a polycyclic group. Examples of heteroaryl groups are pyridinyl, pyridazinyl, imidazolyl, pyrimidinyl, pyrazolyl, triazolyl, pyrazinyl, quinolyl, isoquinolyl, 1,2,3,4-tetrahydroquinolyl, tetrazolyl, furyl, thienyl, isoxazolyl, thiazolyl, oxazolyl, isothiazolyl, pyrrolyl, indolyl, benzimidazolyl, benzofuranyl, indazolyl, indolizinyl, phthalazinyl, triazinyl, 1,3,5-triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl and azaindolyl. In certain aspects of the present application, the heteroaryl is a triazinyl group, or in particular, a 4-substituted-1H-1,2,3-triazol-1-yl group.

A "kinase" as used herein and also as defined and as well known in the art, is an enzyme that transfers a phosphate from adenosine triphosphate (ATP) onto a substrate molecule. A kinase includes a binding site for ATP, which is a cofactor in the phosphorylation, and at least one binding site for the substrate molecule, which is typically another protein.

"Leaving group", as used herein refers to groups that are readily displaced under certain conditions, for example, by a nucleophile, such as an amine, a thiol or an alcohol nucleophile or its salt. Such leaving groups are well known in the art and include, for example carboxylates, N-hydroxysuccinimide, N-hydroxybenzotriazole, halides, triflates, tosylates, —OR and —SR and the like.

A "ligand" is a molecule, preferably having a molecular weight of less than about 800 Da., more preferably less than about 600 Da., comprising a group exhibiting affinity for one or more binding sites on a biological target molecule, such as a protein. The ligands preferably exhibit nanomolar binding affinity for the biological target molecule. In certain aspects as disclosed herein, a ligand is used interchangeably with a "substrate."

As used herein, where a divalent group, such as a linker for example, is represented by a structure —O—X— as described herein, or generically as -A-B-, as shown below for example, it is intended to also represent a group that may be attached in both possible permutations, as noted in the two structures below.

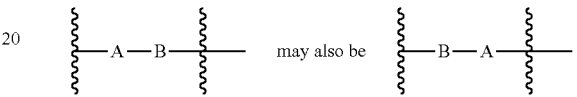

For example, when a divalent group such as the group "—N(R$^{10}$)C(O)—" is provided, for example, the group is intended to also include both the divalent group —N(R$^{10}$)C (O)— and also the divalent group —C(O)N(R$^{10}$)—.

The substituents or the groups C$_{1-6}$alkyl, C$_{3-6}$cycloalkyl, C$_{3-12}$cycloalkylC$_{1-5}$alkyl, C$_{6-14}$aryl, C$_{6-14}$aryloxy, C$_{6-10}$arylC$_{1-4}$alkyl, heteroaryl, heteroaryloxy etc. . . . of the variables R$^1$, R$^2$, R$^3$, R$^4$, R$^{10}$ and R$^{11}$ are also optionally further substituted by substituents selected from the group consisting of amino, halo, cyano, nitro, hydroxy, —SH, —SC$_{1-6}$alkyl, —C(O)NH$_2$, —C(S)NH$_2$, haloC$_{1-6}$alkyl, perhaloC$_{1-6}$alkyl, C$_{1-6}$alkyl, C$_{3-6}$cycloalkyl, C$_{3-12}$cycloalkyl, C$_{6-14}$aryl and heteroaryl. In certain variations, the substituents are amino and hydroxy.

In certain aspect of the present application, the heteroaryl substituent is a 4-substituted-1H-1,2,3-triazol-1-yl. In the radiolabeled compounds of the present application, a radionuclide may be attached to an aryl group of the compound of Formula 1, or a 2-($^{18}$F-fluoroethyl)-, 2-($^{18}$F-fluoromethyl)-, a $^{11}$C-methoxy-group that is attached to a compound of Formula 1, for example, and/or the radionuclide may be attached to any one or more of the variables R$^1$, R$^2$, R$^3$, R$^4$, R$^{10}$ and R$^{11}$ by way of a $^{18}$F-fluoroethyl-group, a $^{18}$F-fluoromethyl-group, a $^{11}$C-methoxy-group, 4-[($^{18}$F-fluoroethyl)-1H-1,2-3-triazol-1-yl]-ethoxy-group, 4-[($^{18}$F-fluoroethyl)-1H-1,2-3-triazol-1-yl]-propyloxy-group, a $^{123}$I, a $^{124}$I, a $^{125}$I or a $^{131}$I group, and the like. Unless otherwise noted, a compound represented as being substituted by an atom, such as the generic representation by the atom fluorine in F—CH$_2$CH$_2$— or F—CH$_2$CH$_2$O— as attached to a compound of the Formula 1, for example, is intended to cover both the naturally occurring element $^{19}$F (fluorine-19) as well as the $^{18}$F (fluorine-18) isotope(s) of the element itself.

The term "optionally substituted" or "substituted" refers to the specific substituents or groups, such as an alkyl, alkylenyl, cycloalkyl, cycloalkylenyl, aryl, arylenyl, heteroaryl, heteroarylenyl, etc. . . . wherein one to four hydrogen atoms in the group may be replaced by one to four substituents, for example, independently selected from the substituents amino, halo, cyano, nitro, hydroxy, —SH, —SC$_{1-6}$alkyl, —OC$_{1-6}$alkyl such as methoxy, ethoxy, isopropoxy, etc. . . . , —C(O)NH$_2$, —C(S)NH$_2$, haloC$_{1-6}$alkyl, perhaloC$_{1-6}$alkyl, C$_{1-6}$alkyl, C$_{3-6}$cycloalkyl, C$_{3-12}$cycloalkyl, C$_{6-14}$aryl and heteroaryl, or as specifically disclosed herein. In addition, the substituents may also include alkyl, aryl, alkylene-aryl, hydroxy, alkoxy, aryloxy, perhaloalkoxy, heterocyclyl, azido, amino, guanidino, amidino, halo, alkylthio, oxo, acylalkyl, carboxy esters, carboxyl, carboxamido, acyloxy, aminoalkyl, alkylaminoaryl, alkylaminoalkyl, alkoxyaryl, arylamino, phosphono, sulfonyl, carboxamidoaryl, hydroxyalkyl, haloalkyl, alkoxyalkyl and perhaloalkyl. In addition, in certain aspect of the present application, the term "optionally substituted" or "substituted" in reference to the variables $R^1$, $R^2$, $R^3$, $R^4$, $R^{10}$ and $R^{11}$, includes groups substituted by one to four substituents, as identified above, that further comprise a positron or gamma emitter. Such positron emitters include, but are not limited to, $^{11}C$, $^{13}N$, $^{15}O$, $^{18}F$, $^{123}I$, $^{124}I$, $^{125}I$, $^{131}I$ and $^{77}Br$.

The terms "patient" and "subject" refer to any human or animal subject, particularly including all mammals.

"Radiochemical" is intended to encompass any organic, inorganic or organometallic compound comprising a covalently-attached radioactive isotope, any inorganic radioactive ionic solution (e.g., $Na[^{18}F]F$ ionic solution), or any radioactive gas (e.g., $[^{11}C]CO_2$), particularly including radioactive molecular imaging probes intended for administration to a patient (e.g. by inhalation, ingestion, or intravenous injection) for tissue imaging purposes, which are also referred to in the art as radiopharmaceuticals, radiotracers, or radioligands. Although the present invention is primarily directed to synthesis of positron-emitting molecular imaging probes for use in PET imaging systems, the invention could be readily adapted for synthesis of any radioactive compound comprising a radionuclide, including radiochemicals useful in other imaging systems, such as single photon emission computed tomography (SPECT).

"Radioactive isotope" refers to isotopes exhibiting radioactive decay (i.e., emitting positrons) and radiolabeling agents comprising a radioactive isotope (e.g., $[^{11}C]$methane, $[^{11}C]$carbon monoxide, $[^{11}C]$carbon dioxide, $[^{11}C]$phosgene, $[^{11}C]$urea, $[^{11}C]$cyanogen bromide, as well as various acid chlorides, carboxylic acids, alcohols, aldehydes, and ketones containing carbon-11). Such isotopes are also referred to in the art as radioisotopes or radionuclides. Radioactive isotopes are named herein using various commonly used combinations of the name or symbol of the element and its mass number (e.g., $^{18}F$, F-18, or fluorine-18). Exemplary radioactive isotopes include I-124, F-18 fluoride, C-11, N-13, and O-15, which have half-lives of 4.2 days, 110 minutes, 20 minutes, 10 minutes, and 2 minutes, respectively.

A "monosaccharide," "disaccharide" or "oligosaccharide" that forms part of the linker X attached to the oxygen atom and the Z group of the group "—O—X—Z" refers to a monosaccharide, disaccharide or oligosaccharide that can be covalently attached to the compound of the Formula 1 via any atom of the saccharide moiety, for example, via the aglycone carbon atom and/or by way of a hydroxyl group. By way of example, a monosaccharide may be attached to O or Z by way of functionalization of a hydroxyl group of the monosaccharide and also attached to the glycosidic bond.

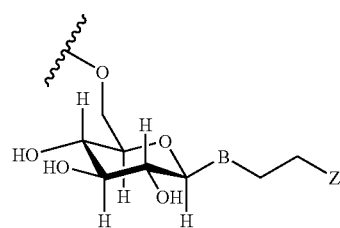

-continued

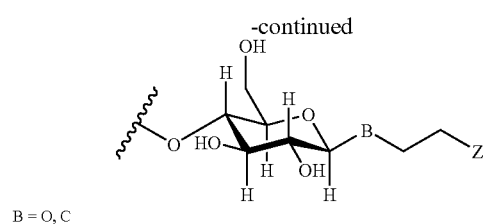

B = O, C

A "saccharide" may also refer to an oxidized, reduced or substituted saccharide diradical. The term includes amino-containing saccharide groups. Representative saccharides include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose, 2-O-(3-desmethyl-α-L-vancosaminyl)-β-D-glucopyranose, sucrose, lactose, or maltose; derivatives such as acetals, amines, acylated, sulfated and phosphorylated sugars; oligosaccharides having from 2 to 10 saccharide units.

Compounds of the Formula 1 may have optical centers and therefore may occur in different enantiomeric and diastereomeric configurations. The present invention includes all enantiomers, diastereomers, and other stereoisomers of such compounds of the Formula 1, as well as racemic compounds and racemic mixtures and other mixtures of stereoisomers thereof. Pharmaceutically acceptable salts of the compounds of Formula 1 include the acid addition and base salts thereof. Suitable acid addition salts are formed from acids which form non-toxic salts. Examples include, but are not limited to, the acetate, adipate, aspartate, benzoate, besylate, bicarbonate/carbonate, bisulphate/sulphate, borate, citrate, formate, fumarate, gluconate, glucuronate, hydrochloride/chloride, hydrobromide/bromide, hydroiodide/iodide, lactate, malate, maleate, malonate, mesylate, methylsulphate, naphthylate, oxalate, palmitate, phosphate/hydrogen phosphate/dihydrogen phosphate, pyroglutamate, salicylate, stearate, succinate, sulfonate, tartrate, tosylate and trifluoroacetate salts. Suitable base salts are formed from bases which form non-toxic salts. Examples include, but are not limited to, the aluminum, arginine, benzathine, calcium, choline, diethylamine, diolamine, glycine, lysine, magnesium, potassium, sodium, tromethamine and zinc salts. Hemisalts of acids and bases may also be formed, for example, hemisulphate and hemicalcium salts. For a review on suitable salts, see *Handbook of Pharmaceutical Salts: Properties, Selection, and Use* by Stahl and Wermuth (Wiley-VCH, 2002) and *Remington: The Science and Practice of Pharmacy*, A. Gennaro, ed., 20th edition, Lippincott, Williams & Wilkins, Philadelphia, Pa. Pharmaceutically acceptable salts of compounds of Formula 1 may be prepared by one or more of three methods: (i) by reacting the compound of Formula 1 with the desired acid or base; (ii) by removing an acid- or base-labile protecting group from a suitable precursor of the compound of Formula 1; or (iii) by converting one salt of the compound of Formula 1 to another salt by the reaction with an appropriate acid or base or by means of a suitable ion exchange column.

The design of the new nucleoside analogs, such as the thymidine analogs of the present application, comprises in part, specific modifications on the nucleoside scaffold in order to enhance membrane transport, phosphorylation rates, radiochemical yields and tumor to background signals in the PET image. In a particular aspect, the nucleoside analog is a thymidine analog. The choice of the linking unit between the nucleosides, such as thymidine, and the radioactive element is a factor considered in the analog's design and success as an imaging agent. It is important that these modifications do not interfere with transport, phosphorylation or accelerate unwanted metabolite formation.

Exemplified Compounds and Their In Vitro and In Vivo Data

TABLE 1

List of prepared thymidine analogs and summary data.

| Entry | Chemical Structure | Mol. Wt. | QPlogP o/w (Calc.) | In Vitro $P_i$ %$^a$ | In Vitro Cell Uptake$^b$ | In Vivo (rodents) Type of Clearance | In Vivo (rodents) Ratio |
|---|---|---|---|---|---|---|---|
| Thymidine | 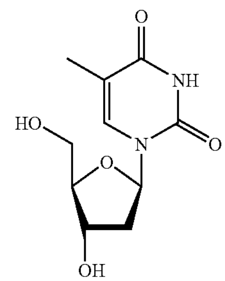 | 242.23 | −0.92 | 97 | (i) 0.537 (ii) 0.417 (iii) 0.107 (iv) 0.189 | Known on $^{11}$C Lung clearance ($^{11}CO_2$) | — |
| FLT | 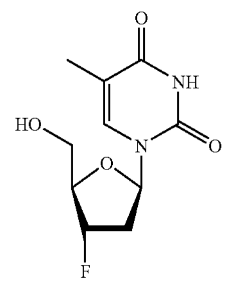 | 244.22 | 0.10 | 31 | (i) 0.108 (ii) 0.034 (iii) 0.115 (iv) 0.173 | Clear through renal system; localize within the tumor | 6~7 (T/M) (after 50 min) |
| FMAU | 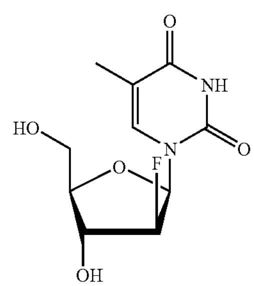 | 260.22 | −0.75 | 80 | (i) 0.012 (ii) 0.011 (iii) 0.015 | Hepatobiliary clearance$^c$ | 2.66 (T/B, lung Cancer) |
| FLT-Click-1 | 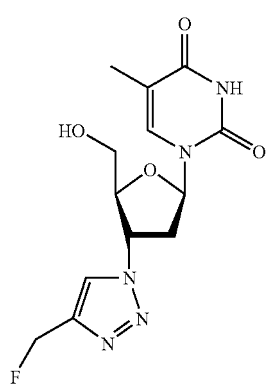 | 325.30 | 0.19 | 6.1 | — | Clear very rapidly from the blood; localize mainly in the bladder | — (T/B; p.i. 45 min) |

TABLE 1-continued

List of prepared thymidine analogs and summary data.

| Entry | Chemical Structure | Mol. Wt. | QPlogP o/w (Calc.) | In Vitro $P_i$ %[a] | Cell Uptake[b] | In Vivo (rodents) Type of Clearance | Ratio |
|---|---|---|---|---|---|---|---|
| FLT-Click-2 | 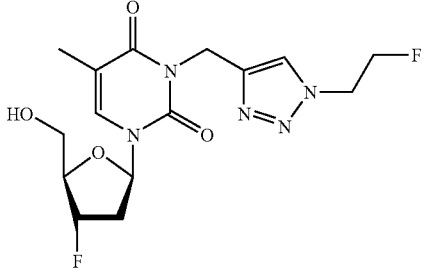 | 371.34 | 1.51 | 4.5 | (i) 0.003 (ii) 0.080 | Clear through the gut/ hepatobiliary system; localize moderately within the tumor ($\leq$1% ID/g) | 1.75 (T/B; p.i. 45 min) |
| FLT-Click-3 | 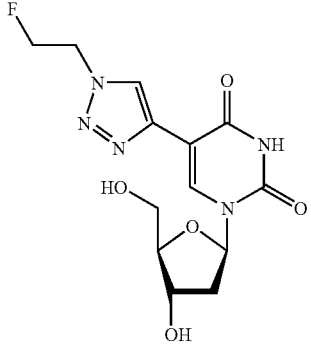 | 341.30 | −0.67 | 0 | — | Clear through the gut; but did not localize within the tumor | 1.1 (T/B; p.i. 45 min) |
| Ta-1 | 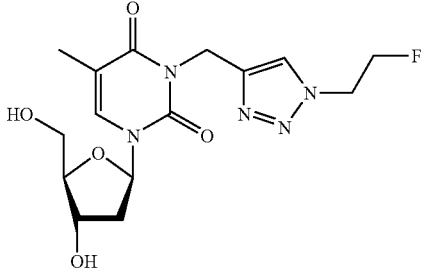 | 369.35 | 0.41 | 65.6 | (i) 0.045 (ii) 0.081 (iii) 0.042 (iv) 0.064 | Clear through the gut/ hepatobiliary system; localize mainly in the gut; a small percentage of the inject dose penetrate and localize within the tumor ($\leq$1% ID/g) | 2.1 (T/M; p.i. 50 min) |
| Ta-4 | 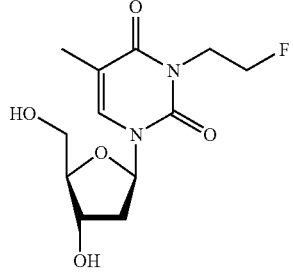 | 288.27 | 0.37 | 77.4 | (i) 0.172 (ii) 0.218 (iii) 0.142 | Less liver uptake than Ta-1; localize more strongly within the A431 based tumor; possess a clearance mechanism similar to FLT (2-3.5% ID/g) | 2.3 (T/M; p.i 50 min) |

TABLE 1-continued

List of prepared thymidine analogs and summary data.

| Entry | Chemical Structure | Mol. Wt. | QPlogP o/w (Calc.) | In Vitro $P_i$ %[a] | In Vitro Cell Uptake[b] | In Vivo (rodents) Type of Clearance | In Vivo (rodents) Ratio |
|---|---|---|---|---|---|---|---|
| Ta-10 | 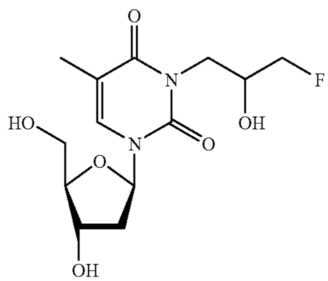 | 318.30 | −0.37 | 27.5 | (i) 0.023 (ii) 0.031 (iii) 0.017 | Clear through the gut/renal system; localize moderately within the tumor (≦1% ID/g) | 0.35 (T/M) |
| Ta-2 | 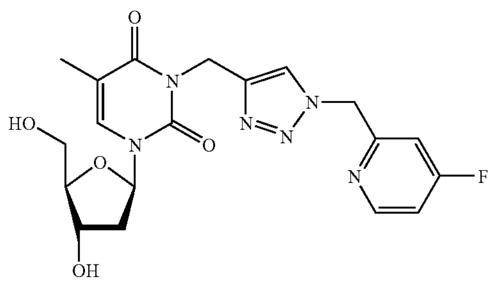 | 432.41 | 1.06 | 39.2 | (i) 0.019 (ii) 0.030 (iii) 0.071 (iv) 0.090 | — | — |
| Ta-3 | 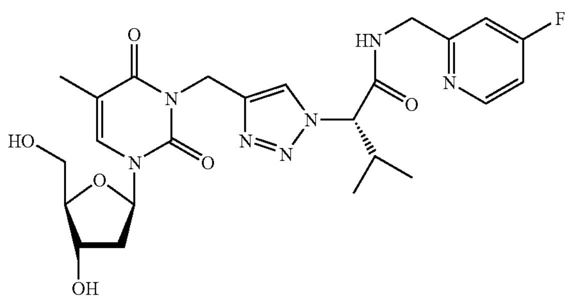 | 531.54 | 0.89 | 25.5 | (i) 0.004 (ii) 0.059 (iii) 0.093 (iv) 0.117 | Clear through the bowels; localize mainly in the gut | — |
| Ta-4D | 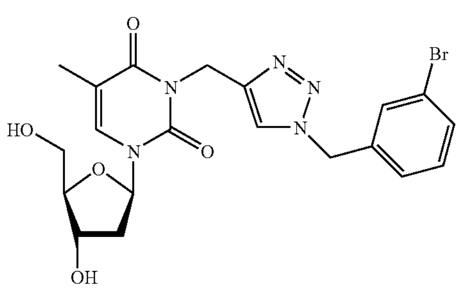 | 492.32 | 2.03 | 51.9 | — | — | — |
| Ta-4F | 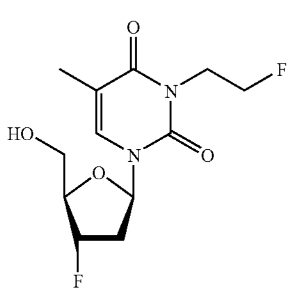 | 290.26 | 1.42 | 9.2 | (i) 0.075 (ii) 0.063 (iii) 0.067 | — | — |

TABLE 1-continued

List of prepared thymidine analogs and summary data.

| Entry | Chemical Structure | Mol. Wt. | QPlogP o/w (Calc.) | In Vitro | | In Vivo (rodents) | |
|---|---|---|---|---|---|---|---|
| | | | | $P_i$ %[a] | Cell Uptake[b] | Type of Clearance | Ratio |
| Ta-6233 | 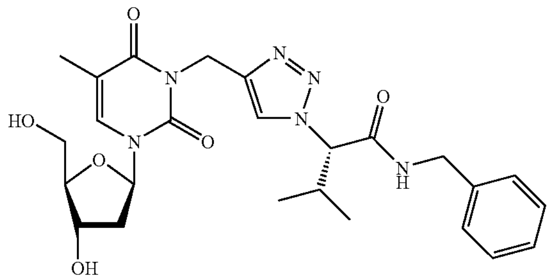 | 512.56 | 0.77 | 71.5 | — | — | — |
| Ta-5 | 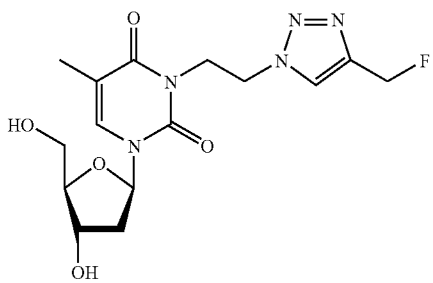 | 369.35 | 0.35 | 10.2 | (i) 0.068 (ii) 0.072 (iii) 0.051 | — | — |
| Ta-6 | 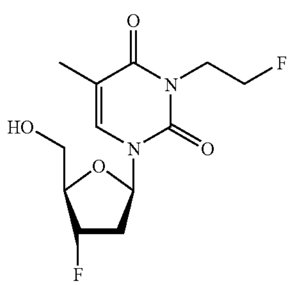 | 290.26 | 1.48 | 4.5 | (i) 0.023 (ii) 0.007 (iii) 0.004 | — | — |
| Ta-7 | 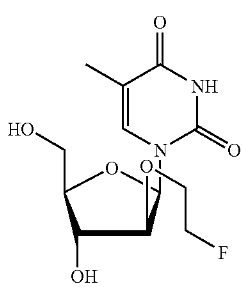 | 304.27 | −0.40 | 5.6 | (i) 0.027 (ii) 0.083 (iii) 0.004 | Clear through the gut/hepatobiliary system; localize mainly in the gut; a small percentage of the inject dose penetrate and localize within the tumor (≦1% ID/g) | 1.05 (T/M) |
| Ta-8 | 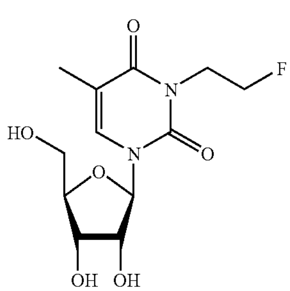 | 304.27 | −0.65 | 18.2 | (i) 0.052 (ii) 0.097 (iii) 0.018 | Clear through the renal system; localize moderately within the tumor (≦1% ID/g) | 0.99 (T/M) |

TABLE 1-continued

List of prepared thymidine analogs and summary data.

| Entry | Chemical Structure | Mol. Wt. | QPlogP o/w (Calc.) | $P_i$ %[a] | In Vitro Cell Uptake[b] | In Vivo (rodents) Type of Clearance | Ratio |
|---|---|---|---|---|---|---|---|
| Ta-9 | 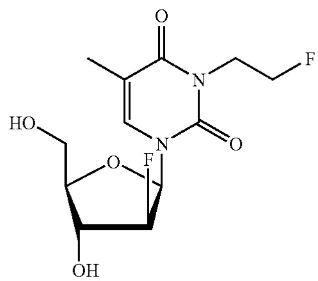 | 306.26 | 0.56 | 1.4 | (i) 0.027 (ii) 0.014 (iii) 0.009 | — | — |
| Ta-11 | 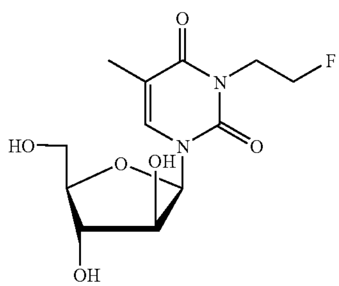 | 304.27 | −0.45 | 9.8 | (i) 0.03 (ii) 0.02 (iii) 0.006 | Clear through the renal system; localize moderately within the tumor (≦1% ID/g) | 0.52 (T/M) |
| Ta-12 | 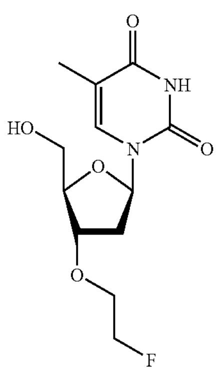 | 287.27 | ND | ND | ND | — | |
| Ta-14 | 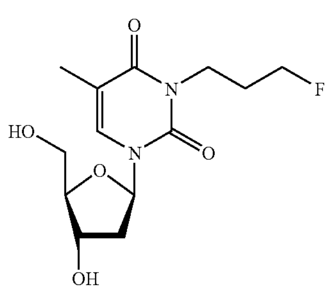 | 302.30 | ND | ND | ND | — | |

TABLE 1-continued

List of prepared thymidine analogs and summary data.

| Entry | Chemical Structure | Mol. Wt. | QPlogP o/w (Calc.) | In Vitro | | In Vivo (rodents) | |
|---|---|---|---|---|---|---|---|
| | | | | $P_i$ %[a] | Cell Uptake[b] | Type of Clearance | Ratio |
| Ta-15 | | 332.32 | ND | ND | ND | — | |
| Ta-16 | | 332.32 | ND | ND | ND | — | |
| Ta-17 | | 316.33 | ND | ND | ND | — | |
| Ta-18 | | 332.32 | ND | ND | ND | — | |

TABLE 1-continued

List of prepared thymidine analogs and summary data.

| Entry | Chemical Structure | Mol. Wt. | QPlogP o/w (Calc.) | In Vitro | | In Vivo (rodents) | |
|---|---|---|---|---|---|---|---|
| | | | | $P_i$ %[a] | Cell Uptake[b] | Type of Clearance | Ratio |
| Ta-19 | 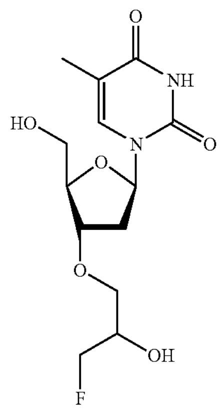 | 318.30 | ND | ND | ND | — | |
| Ta-20 | 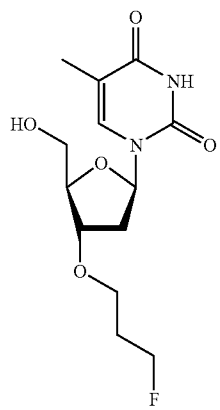 | 302.30 | ND | ND | ND | — | |
| Ta-21 | 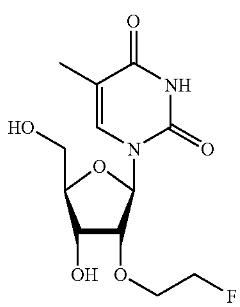 | 304.27 | ND | ND | ND | — | |

[a]Phosphorylation percentage.
[b]Cell lines: (i) A431; (ii) SK-N-MC; (iii) A172; (iv) Balb/3T12-3.
[c]Sun, H., Sloan, A., Mangner, T. J., et al. Eur. J. Nul. Med. Mol. Imag., 2005, 32, 15-22.

Figure 6:
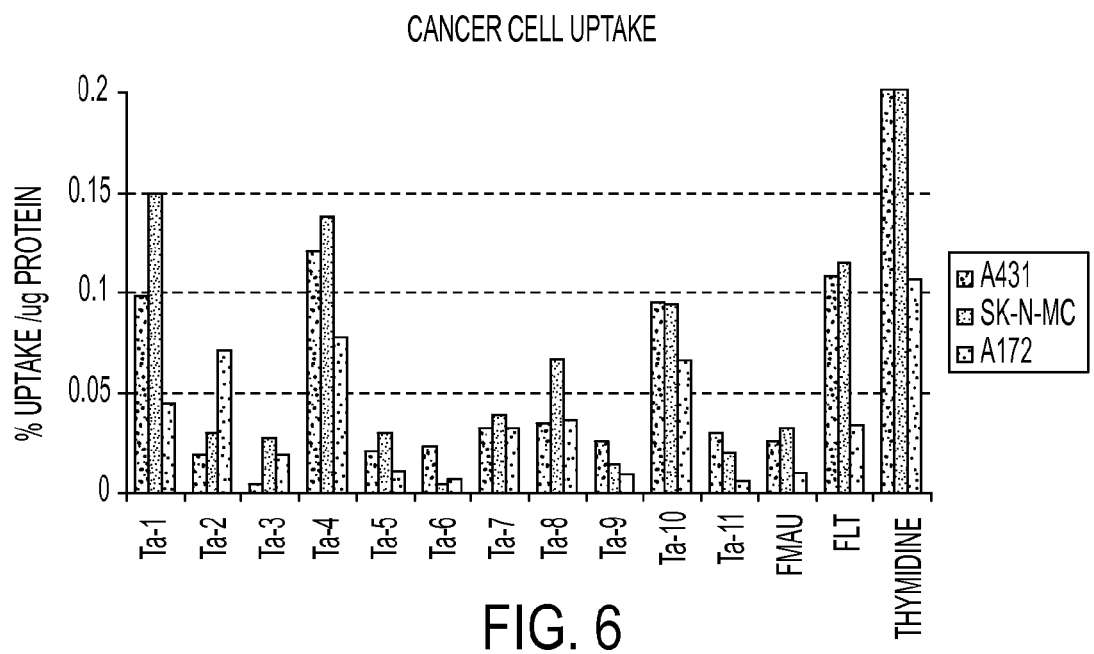
FIG. 6 shows the structure of cancer cell (A431, SK-N-MC, and A172) uptake studies of thymidine analogs. FMAU, FLT and thymidine are used as controls.

Preliminary cellular uptake analysis of a series of 3-N, 3'-O and 2'-O alkylated thymidine analogs in four cell lines, i.e. A431 cell line (human skin epidermoid carcinoma, high S phase), SK-N-MC cell line (human brain neuroepithelioma, high S phase), A172 cell line (human brain glioblastoma, low S phase) revealed uptake values greater than FLT thus demonstrating enhanced transport into these cell lines. High cell uptake values are one favorable factor for successful PET imaging (FIG. 6).

Figure 7:
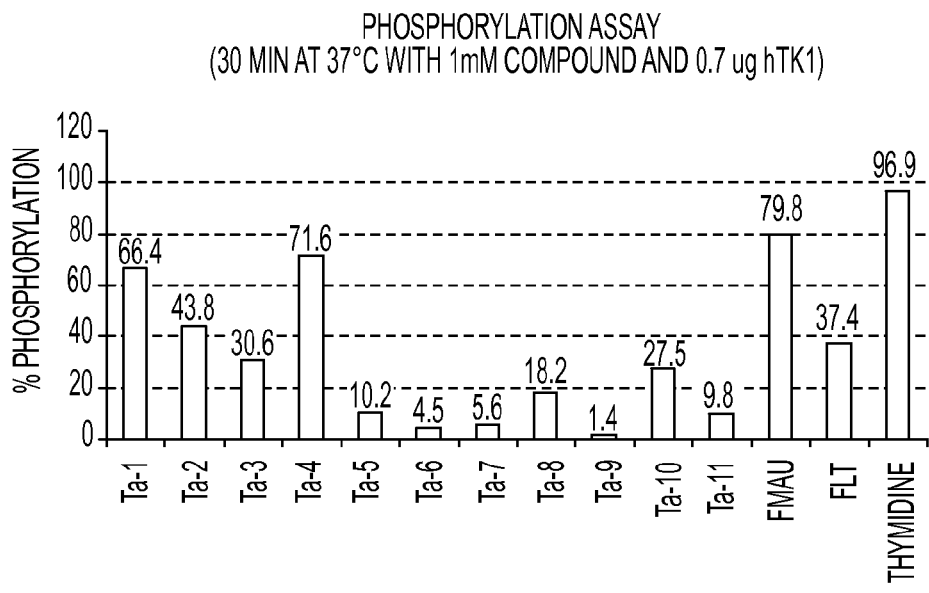
FIG. 7 shows the percent phosphorylation of thymidine analogs. Both thymidine and FLT were used as controls.

In a second series of analyses, the formation of hTK-1 kinase phosphorylated metabolites derived from FLT, thymidine, and thymidine analogs were monitored by HPLC analysis and mass spectrometric detection via electrospray ionization and selected ion mode (LC/MS-SIM). The thymidine analogs demonstrated greater phosphorylation levels relative to FLT and thymidine (FIG. 7). The rates of phosphorylation of these compounds by human thymidine kinase 1 (hTK1) when measured in vitro assays are approximately twice that of FLT and approximately 90% that of thymidine. High rates of phosphorylation are an important aspect for accumulation of the tracer inside cells thus increasing the signal in the PET image. Ta-4 and Ta-1 are favorably taken up and retained intracellularly by SK-N-MC, A172, and BalB/3T12-3 cells in vitro, with SK-N-MC cells displaying the highest uptake values. In addition, many prepared thymidine analogs possess 'drug-like' molecular weights and LogP values which when calculated (QPlogPo/w data (0.3~0.4)) reveal that their lipophilicity profiles are similar to FLT (QPlogPo/w=0.10) and thymidine (QPlogPo/w=−0.92).

Figure 8:
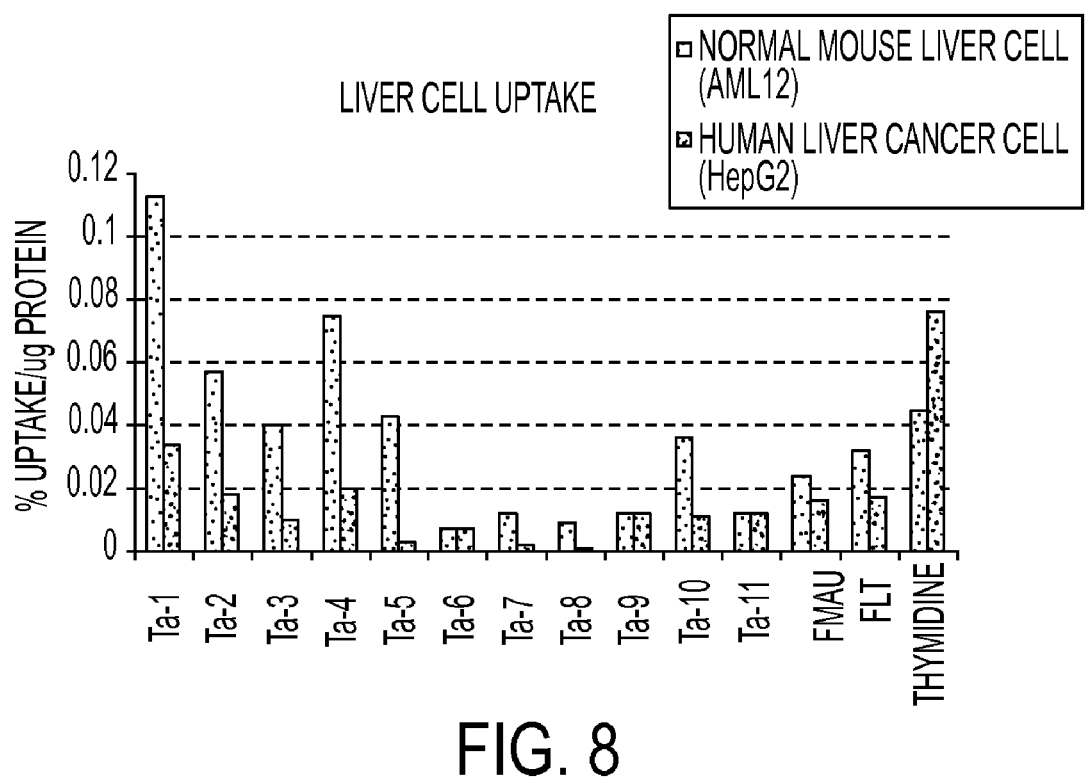
FIG. 8 shows the liver cell uptake studies of thymidine analogs

In the last series of in vitro experiments, the thymidine analogs were incubated with both normal mouse liver cells (AML12) and human liver cancer cells (HepG2) and their uptake of the analogs was measured via LC/MS-SIM (FIG. 8). The mouse liver cell uptake of a small number of thymidine analogs was higher than FLT and thymidine, and the levels of human liver cell uptake were similar to FLT and thymidine. Ideally, low levels of liver cell uptake help increase the tumor to background ratios in the PET image. Furthermore, we examined the metabolic profile of the leads (Ta-1, Ta-4, and Ta-10) in vitro using normal mouse liver cell line (AML12) and human liver cancer cell line (HepG2). The results demonstrated that the in vitro liver cell uptake of Ta-4 is less than Ta-1. The liver cell uptake of Ta-10 is similar to FLT and less than Ta-1 and Ta-4, indicating that Ta-10 may possess a clearance mechanism similar to FLT in vivo.

The incorporation of three different thymidine analogs (Ta-4, -10, -14) into DNA was compared against the DNA incorporation of FMAU (data not shown). Incorporation of FMAU into DNA was very high, yet the incorporation of the thymidine analogs was substantially lower. Despite the fact that all four compounds contain the requisite 3'-hydroxyl group necessary for DNA incorporation, only FMAU exhibits a high incorporation rate. This finding suggests that the mechanism of location for Ta-4, -10 and -14 is strongly dependent on 5'-phosphorylation and not necessarily DNA incorporation.

Figure 9:
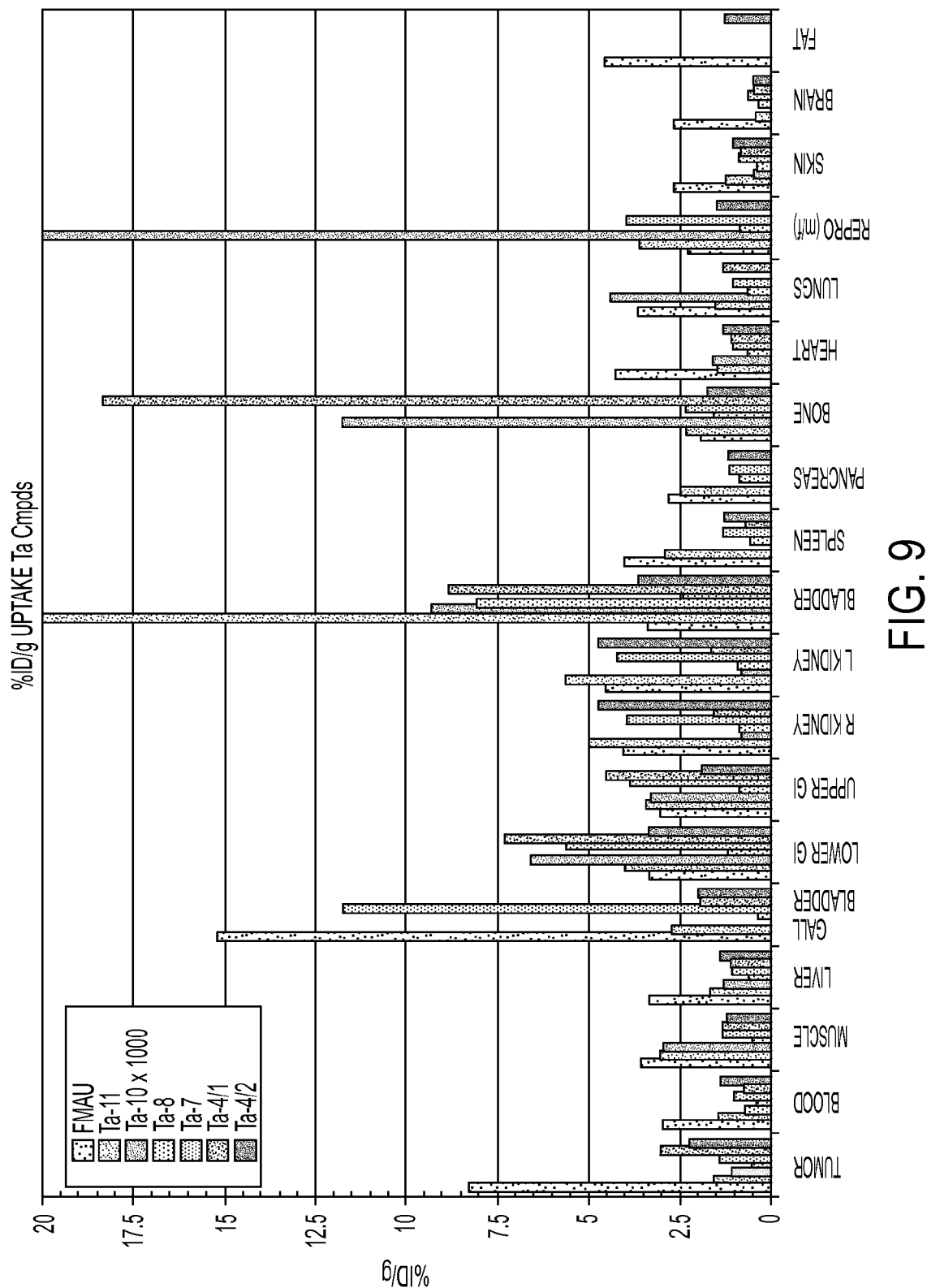
FIG. 9 shows the biodistribution data of Ta-4 in an A431 tumor bearing nude mouse.

The thymidine analogs also show favorable in vivo imaging characteristics as shown in the non-radioactive PK analysis. For example, analog Ta-4 rapidly clears from the blood, localizes to the tumor, has little hepatic uptake and clears mainly via the kidneys (FIG. 9). Other thymidine analogs also display favorable uptake and signal to background ratios.

Figure 10:
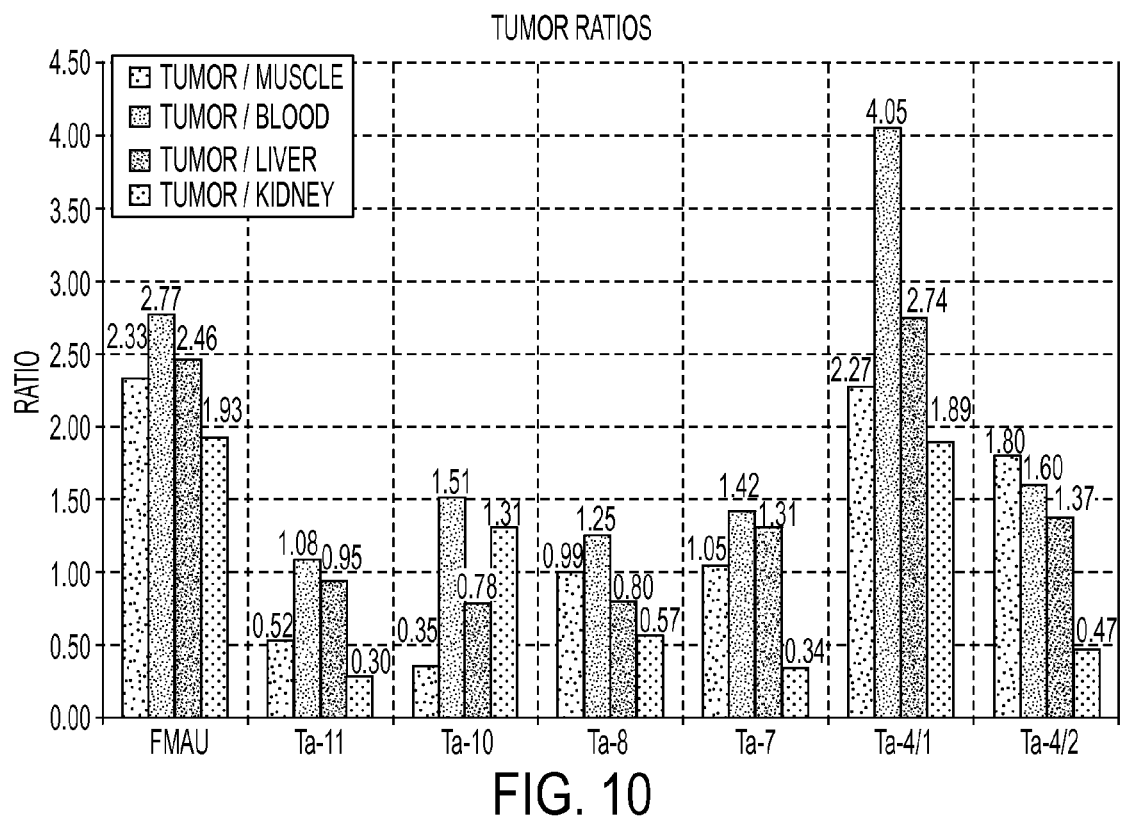
FIG. 10 shows the tumor to organ ratios of various thymidine analogs. FMAU was used as the control.
Figure 11:
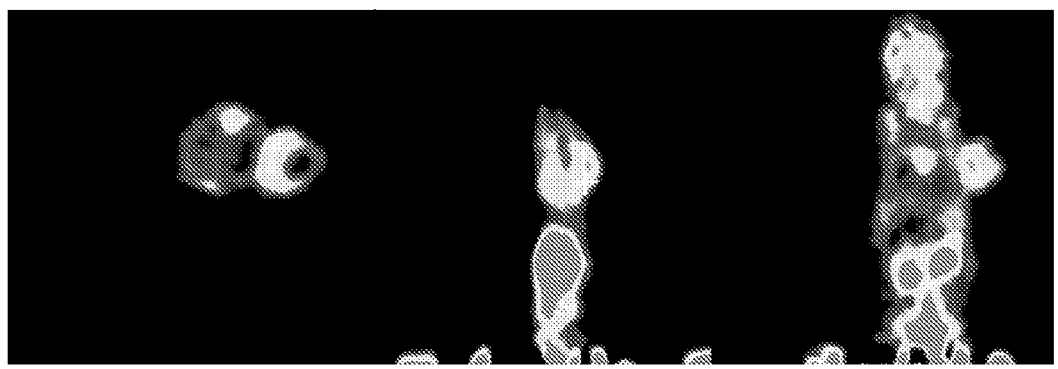
FIG. 11 shows PET Images of TA-4 in an A431 tumor bearing mouse (coronal, sagital, transverse) 60 min post injection. The crosshairs are placed on top of the tumor.
Figure 12:
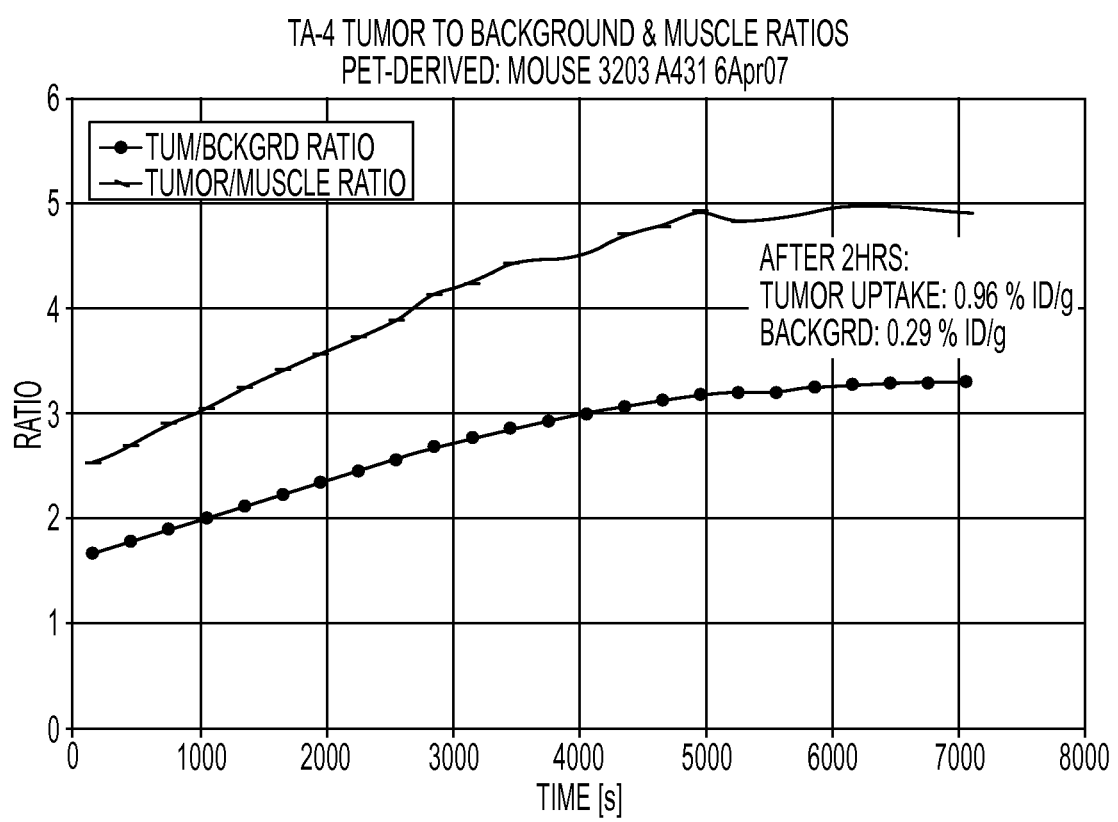
FIG. 12 shows tumor to background and muscle ratios for Ta-4 derived from PET imaging data.

The results of tumor ratios for various Ta analogs is shown in FIG. 10. The results from the Ta-3 in vivo imaging of A431 tumor bearing mice revealed large localization of the tracer in the gut and clearance through the bowels. The results from Ta-1 imaging in the same mice were more promising: despite rapid gut clearance, a small percentage of the inject dose penetrated and localized within the tumor. The results indicated that the transport and phosphorylating enzymes tolerate, to an extent, steric bulk in the 3-N position. However, the steric bulk at the 3-N position does not fully explain the clearance pathway observed in the mouse images. Ta-4 has less liver uptake than Ta-1, localizes more strongly within the A-431 based tumor and possesses a clearance mechanism similar to FLT (FIGS. 10, 11 and 12).

Uses of the Radiolabeled Thymidine Analogs:

The radiolabeled thymidine analogs can be used as imaging agents to image proliferation in a subject. In addition, the present invention relates to the use of radiolabeled thymidine analogs for detecting cell proliferation in vivo. In particular, the present methods for detecting cellular proliferation in vivo utilize PET, where the imaging tracer is a radiolabeled thymidine analog of the present invention. PET is useful for visualizing a subject's condition in relation to various tissues, especially bone and soft tissues, such as cartilage, synovium and organs. Specific organs and tissues including, but not limited to, the brain, heart, kidney, liver, spleen, colon, spinal cord, lymph nodes, or any combination thereof, of the subject. By using PET, a computer tomogram can be obtained of the desired organ tissue, enabling the localization and quantification.

The radiolabeled thymidine analogs of the present invention can be used to detect and/or quantitatively measure cell proliferation levels in a subject, including humans. The radiolabeled triazole compounds can also be used to measure and/or detect diseases, disorders and conditions, including, but not limited to, cancer of the breast, lung, prostate, bladder, cervix, and skin, gastrointestinal conditions, such as inflammatory bowel disease, gastritis, irritable bowel syndrome, autoimmune diseases in general, allograft rejection, asthma, bronchitis, tendonitis, bursitis, dermatitis, and central nervous system disorders, such as cortical dementias including Alzheimer's disease and central nervous system damage resulting from stroke, ischemia and trauma, arthritis, vascular disease, migraine headaches, rheumatic fever, diabetes, postoperative inflammation, such as that resulting from ophthalmic surgery, respiratory distress syndrome, and pulmonary inflammation, such as that resulting from viral and bacterial inflections as well as from cystic fibrosis.

Administration of the Radiolabeled Thymidine Analogs:

As described above, the radiolabeled thymidine analogs are useful for imaging a cellular proliferation subject. When administered to a subject, the radiolabeled thymidine analogs can be administered as a component of a composition that comprises a physiologically acceptable carrier or vehicle. The present compositions, which comprise a radiolabeled thymidine analog, can be administered by any convenient route, for example, by infusion, bolus injection, or by absorption through epithelial or mucocutaneous linings and can be administered together with another biologically active agent. Administration can be systemic or local. Methods of administration include, but are not limited to, intradermal, intramuscular, intraperitoneal, intravenous, subcutaneous, intranasal, sublingual, epidural, intracerebral, intravaginal, transdermal, rectal, or topical.

The radiolabeled thymidine analogs may also be administered locally. This can be achieved, for example, and not by way of limitation, by local infusion during surgery, by injection, by means of a catheter, by means of a suppository or enema, or by means of an implant, with said implant being of a porous, non-porous, or gelatinous material, including membranes, such as sialastic membranes or fibers. In addition, the radiolabeled thymidine analogs can be delivered in a controlled-release system or sustained-release system. The controlled-release system or sustained-release system can be placed in proximity to a target of the radiolabeled thymidine analogs, e.g., the spinal column, brain, heart, kidney or gastrointestinal tract, thus requiring only a fraction of the systemic dose.

The compositions can optionally comprise a suitable amount of a physiologically acceptable excipient so as to provide the form for proper administration to the subject. Such physiologically acceptable excipients can be liquids, such as water for injection, bactereostatic water for injection, or sterile water for injection. The physiologically acceptable excipients are sterile when administered to a subject. Water is a particularly useful excipient when the radiolabeled triazole compound is administered intravenously. Saline solutions can also be employed as liquid excipients, particularly for injectable solutions. The pharmaceutical excipients can be saline, gum acacia, starch, glucose, lactose, glycerol, ethanol and the like.

Moreover, the radiolabeled thymidine analogs can be formulated for intravenous administration. Typically, compositions for intravenous administration comprise sterile isotonic aqueous buffer. Where the radiolabeled thymidine analogs are administered by injection, an ampule of sterile water for injection or saline can be provided so that the ingredients can be mixed prior to administration. Where the radiolabeled thymidine analogs are to be administered by infusion, they can be dispensed, for example, with an infusion bottle containing sterile pharmaceutical grade water or saline.

The amount of the radiolabeled thymidine analog that is effective as an imaging agent to detect cellular proliferation in a subject can be determined using standard clinical and nuclear medicine techniques. In addition, in vitro or in vivo testing can optionally be employed to help identify optimal dosage ranges. The precise dose to be employed will also depend on the route of administration, the identity of the subject and the identity of the particular radionuclide being detected and should be decided according to the judgment of the practitioner and each subject's circumstances in view of published clinical studies. The radiolabeled triazole compounds will have a specific activity of >1100 Ci/mmol at the time of administration to insure a low injected mass and adequate counts for imaging.

The following procedures may be employed for the preparation of the compounds of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. Suitable protective groups for amino, hydroxy, and carboxy groups are described in Greene et al., *Protective Groups in Organic Synthesis*, Second Edition, John Wiley and Sons, New York, 1991. Standard organic chemical reactions can be achieved by using a number of different reagents, for examples, as described in Larock: *Comprehensive Organic Transformations*, VCH Publishers, New York, 1989.

EXAMPLES

General. The human Thymidine Kinase-1 was ordered from Biaffin GmbH & Co KG. The LC/MS analyses were performed on an Agilent 1100 series LC/MSD (SL) using a 30×2.1 mm Zorbax C8 column with a Phenomenex C18 pre-column. Compound detection was accomplished by electrospray mass spectroscopy in positive selected ion mode (LC/MS-SIM). The elution solvents, acetonitrile and water, contained 0.05% TFA. Nuclear magnetic resonance (NMR) spectra were obtained on a Bruker AMX 300 MHz spectrometer. $^{19}$F NMR spectra were recorded on a Bruker AMX 282.35 MHz spectrometer. The mass spectra were recorded on an Agilent 1100 series LC/MSD with electrospray mass spectroscopic detection. Flash column chromatography was performed either on Merck silica gel (40-63 µm) using the solvent system indicated or on a CombiFlash purification system on silica gel cartridges. The radiochemical and chemical purities were analyzed by RP-HPLC.

Synthesis of Precursors and Standards:

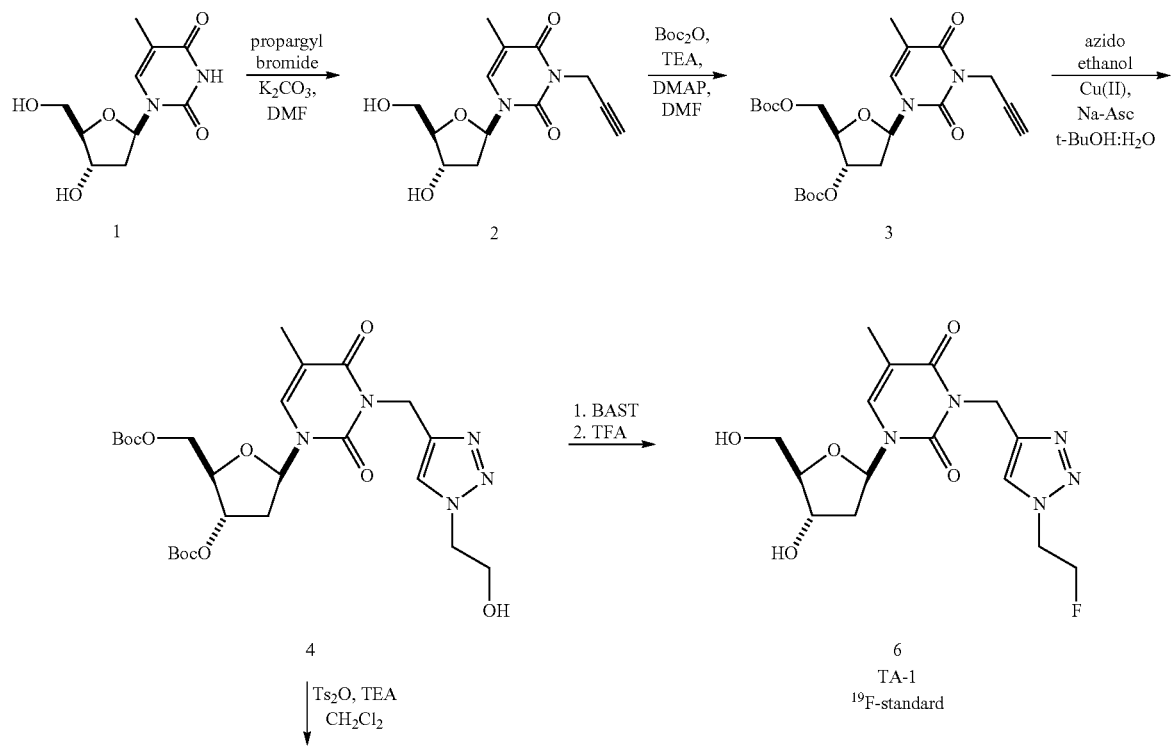

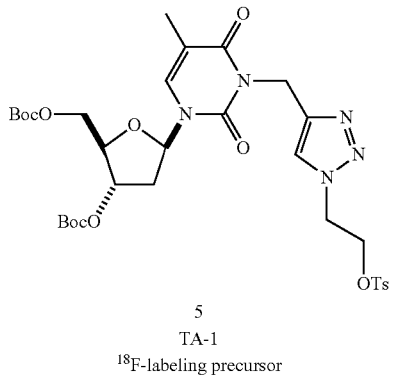

5
TA-1
[18]F-labeling precursor

Synthesis of 2: To a round bottom flask under Ar containing thymidine (4.84 g, 20 mmol) in DMF (20 mL) was added $K_2CO_3$ (3.31 g, 24 mmol) and propargyl bromide (2.86 g, 24 mmol). The reaction was stirred at RT for 2 days. The reaction was then poured onto brine (50 mL) and the product was extracted into EtOAc (3×50 mL). The organics were combined, dried ($MgSO_4$), filtered and concentrated to dryness to afford 2.48 g (44%) of clear, colorless oil.

LC/MS: Expected for $C_{13}H_6N_2O_5$: 280.11; found: 281.1 (M+H), 303.1 (M+Na).

$^1$H NMR ($CDCl_3$, 300 MHz) δ: 7.43 (s, 1H), 6.25 (t, J=6 Hz, 1H), 4.71 (s, 2H), 4.57-4.63 (m, 1H), 3.82-4.09 (m, 3H), 2.37-2.54 (m, 4H), 2.15 (t, J=1.2 Hz, 1H), 1.95 (s, 3H).

Synthesis of 3: To a round bottom flask under Ar containing N-propargyl thymidine (2.1 g, 7.5 mmol) in DCM (20 mL) was added TEA (3.14 mL, 22.5 mmol) and boc anhydride (4.09 g, 18.8 mmol). The reaction was stirred at RT for 6 hrs. A catalytic amount of DMAP (50 mg) was added to the reaction and after 6 hrs the reaction went to completion. The reaction was then poured onto brine (50 mL) and the product was extracted into EtOAc (3×50 mL). The organics were combined, dried ($MgSO_4$), filtered and concentrated to dryness. The material was purified over silica gel using 1:1 $Et_2O$:Hexanes as the eluent to afford 2.1 g (58%) of a white solid.

LC/MS: Expected for $C_{23}H_{32}N_2O_9$: 480.21: found: 503.2 (M+Na).

$^1$H NMR (($CDCl_3$, 300 MHz) δ: 7.45 (s, 1H), 6.43-6.50 (m, 1H), 5.12-5.18 (m, 1H), 4.71 (s, 2H), 4.28-4.52 (m, 3H), 2.15-2.57 (m. 3H), 1.95 (s, 3H), 1.5 (s, 18H).

Synthesis of 4: Alkyne (0.25 g, 0.56 mmol) and azido ethanol (0.05 g, 0.56 mmol) were combined in a vial and dissolved in t-BuOH (2.5 mL). To this mixture, copper sulfate (0.04M in water, 1.4 mL) and sodium ascorbate (0.1M in water. 1.2 mL) were added and stirred at room temperature. After 6 hrs, the reaction was worked up using water and ethyl acetate. The organic layer was dried over $MgSO_4$ and resulting solid was washed with ether. The solid (0.29 g, 95%) was pure and used as is for the next step.

LC/MS: Expected for $C_{25}H_{37}N_5O_{10}$: 567.25; found: 568.2 (M+H).

Synthesis of 5: The hydroxyl triazole (0.298 g, 0.53 mmol) and p-toluenesulfonic anhydride (0.21 g, 0.62 mmol) were dissolved in dichloromethane (15 mL). Triethylamine (0.15 mL, 1.05 mmol) was added dropwise and the reaction stirred at RT for 4 hrs. After 4 hrs, the reaction was quenched with water, extracted into ethyl acetate, dried and concentrated. Pure product was isolated after chromatography on silica gel using ethyl acetate:hexane mixture as eluent (yield not determined).

LC/MS: Expected for $C_{32}H_{43}N_5O_{12}S$: 721.26; found: 722.2 (M+H).

Synthesis of 6: To a round bottom flask containing 4 (1 equiv) in $CH_2Cl_2$ (20 mL) and was treated with bis(2-methoxyethyl)aminosulfur trifluoride (2 equiv) dropwise at −76° C. after addition the temperature was raised to RT. After stirring for 2 hrs, the reaction mixture was quenched with saturated $NaHCO_3$, the organic layer was consecutively washed with $H_2O$ (10 mL), brine (10 mL) and dried over $MgSO_4$. The solvent was removed under vacuum, and the product was isolated by chromatography on silica gel as white solid (yield not determined). To this at 0° C., TFA (neat, excess) was added and the reaction mixture was stirred for 3 hrs and TFA removed under vacuum to get the product 6 as white solid (yield not determined).

$^1$H NMR ($CDCl_3$, 300 MHz): δ 7.75 (s, 1H), 7.45 (s, 1H), 6.2-6.3 (m, 1H), 5.35 (s, 4H), 4.9-4.95 (m, 1H), 4.72-4.75 (m, 1H), 4.6-4.7 (m, 1H), 4.4-4.05 (m, 1H), 3.46-3.6 (m, 4H), 2.4-2.6 (m, 2H). 2.15 (s, 3H).

LC/MS (ESI) (m/z): Expected for $C_{15}H_{20}FN_5O_5$: 369.14; found: 370.2 (M+H).

TA-2
Scheme:

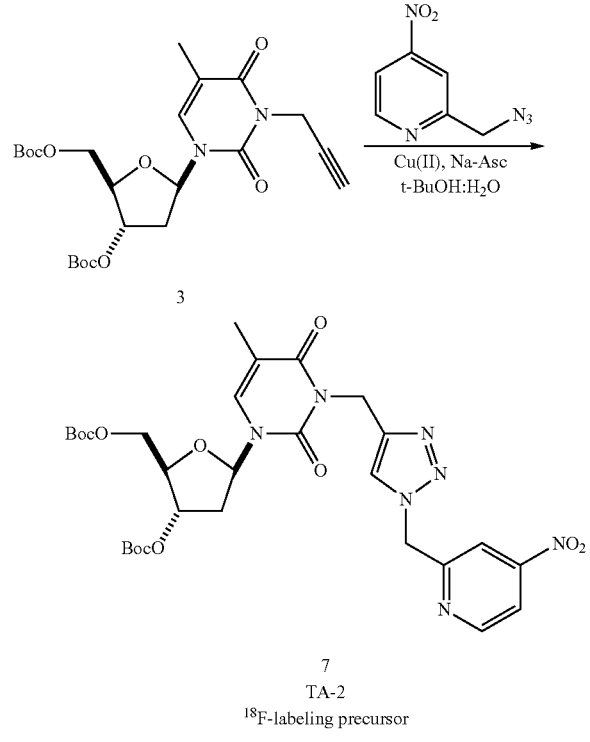

7
TA-2
[18]F-labeling precursor

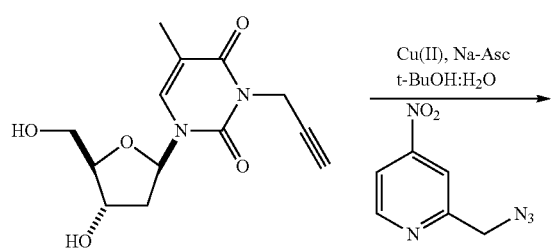

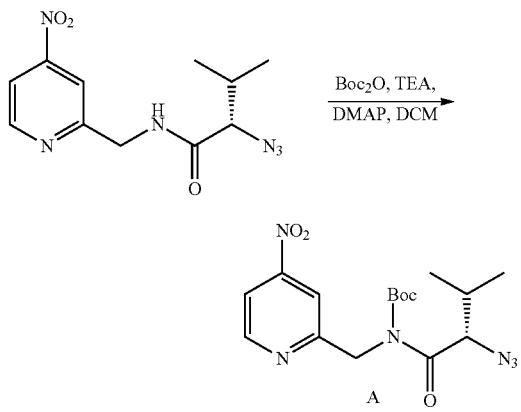

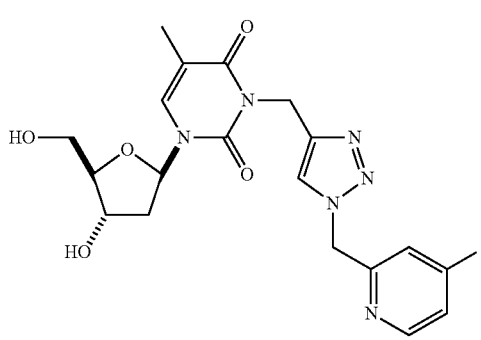

8
TA-2
$^{19}$F-standard

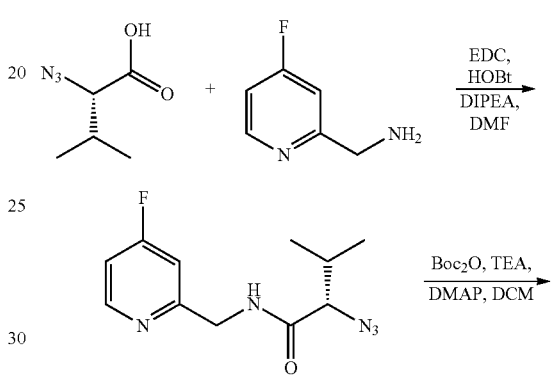

Synthesis of 7: A solution of Alkyne (1 equiv) and 2-(azidomethyl)-4-nitropyridine (1 equiv) in t-BuOH:H$_2$O (1:1, 2.5 mL) was treated with CuSO$_4$.5H$_2$O (0.01 equiv) and sodium ascorbate (0.1 equiv). After stirring the reaction mixture for 1 hr at room temperature, organic solvent was removed under vacuum, the residue dissolved in CH$_2$Cl$_2$ and consecutively washed with H$_2$O and brine and dried over MgSO$_4$, the solvent concentrated in vacuo, and 7 isolated as pure white solid (100%).

Synthesis of 8: A solution of alkyne 2 (13 mg, 0.046 mmoles) and 2-(azidomethyl)-4-fluoropyridine (7 mg, 0.046 mmoles) in t-BuOH:H$_2$O (1:1, 2.5 mL) was treated with CuSO$_4$.5H$_2$O (0.04M, 200 uL) and sodium ascorbate (0.1M, 200 uL). After stirring the reaction mixture for 1 hr at room temperature, the organic solvent was removed under vacuum, dissolved in CH$_2$Cl$_2$ (50 mL) and consecutively washed with H$_2$O (20 mL), brine (20 mL). The organics were dried over MgSO$_4$ and the solvent was concentrated in vacuo. The material was purified over silica gel using 5% MeOH:DCM to afford 2 mg (10% yield) of a white solid.

LC/MS (ESI) (m/z): Expected for C$_{19}$H$_{21}$FN$_6$O: 432.16; found: 455.2 (M+Na).

TA-3
Scheme:

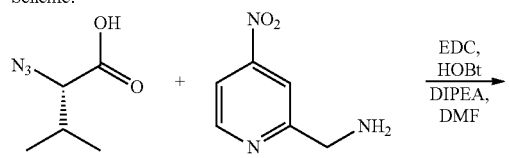

33
-continued

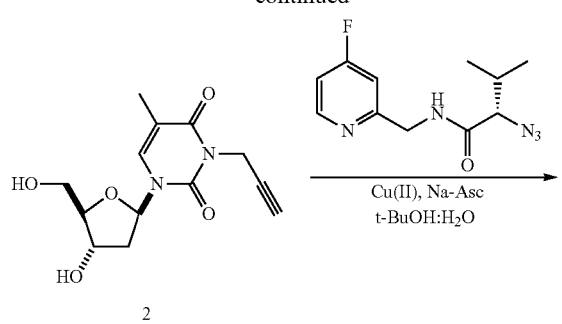

2

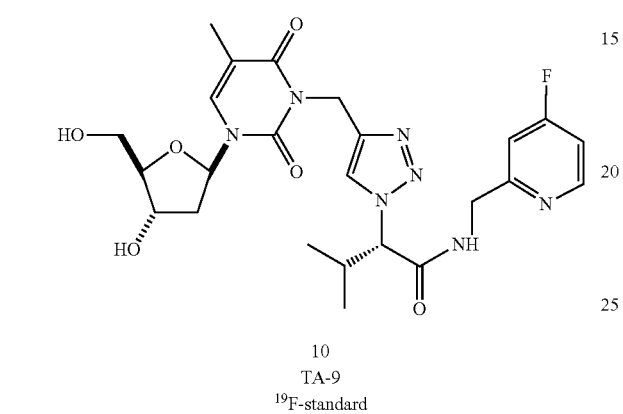

10
TA-9
[19]F-standard

Synthesis of A: To a round bottom flask containing (S)-2-azido-3-methylbutanoic acid (1 equiv) in DMF (5 mL) was treated with HOBt (1.2 equiv) and EDC (1.2 equiv) at room temperature. After stirring for 2 hrs, a solution of (4-nitropyridin-2-yl)methanamine (1.0 equiv) in DMF (2 mL) and DIPEA (1.2 equiv) was added to the reaction mixture and stirred for 2 hrs. The reaction was then poured into water (50 mL) and extracted with EtOAc (20×3 L).

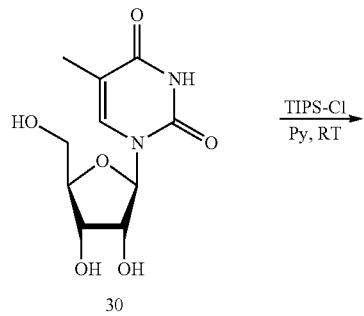

30

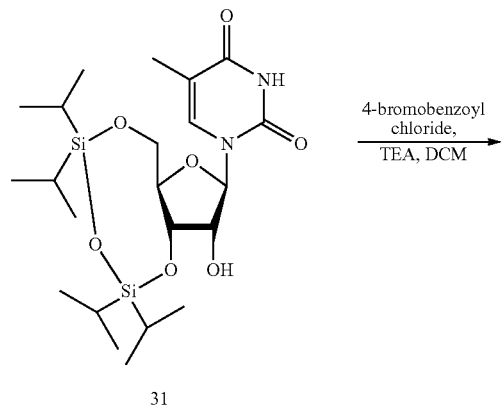

31

34
-continued

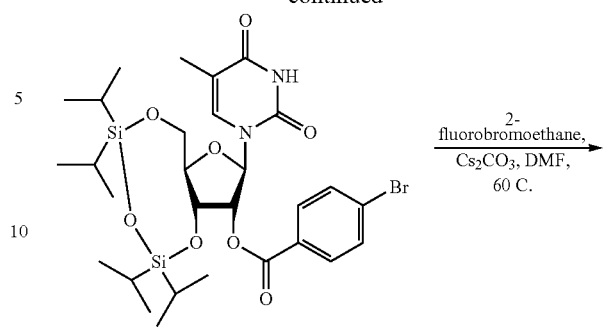

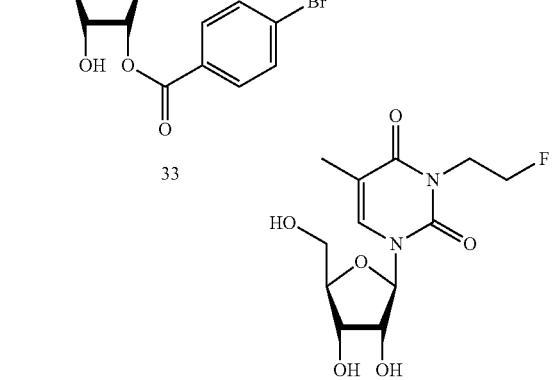

33

34
TA-8
[19]F-standard

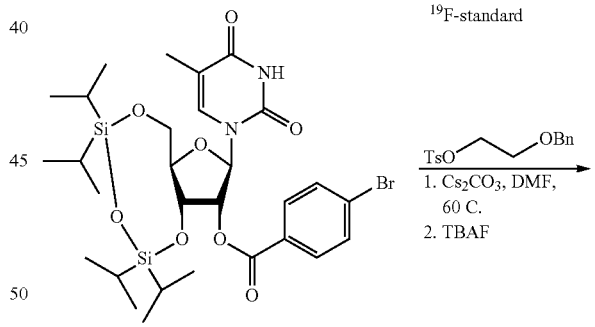

35

35
-continued

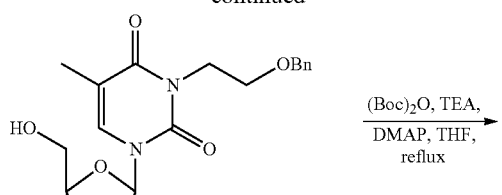
36

(Boc)₂O, TEA,
DMAP, THF,
reflux
→

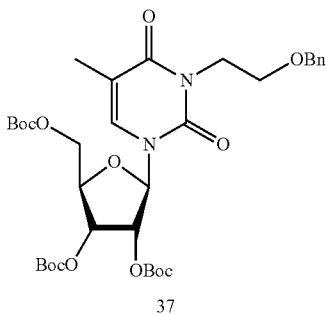
37

1. H₂, Pd/C,
   EtOH, EtOAc
2. Ts₂O, TEA,
   CH₂Cl₂
→

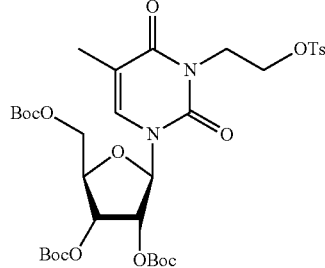
38
TA-8
¹⁸F-labeling precursor

The combined organics were washed with water (10 mL), brine (10 mL) and dried over MgSO₄. The solvent was removed in vacuo, and the product was isolated by chromatography on silica gel using EtOAc:Hexanes as eluent (yield not determined). The purified material was dissolved in DCM (10 mL), triethylamine (1.2 equiv) followed by the addition of a catalytic amount of DMAP and Boc₂O (1.2 equiv). The reaction was stirred overnight at RT. The reaction was concentrated and purified by flash chromatography over silica gel to afford the product A as a white solid (yield not determined).

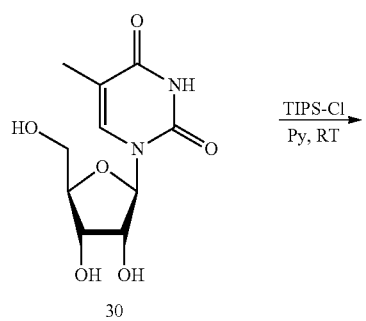
30

TIPS-Cl
—————→
Py, RT

36
-continued

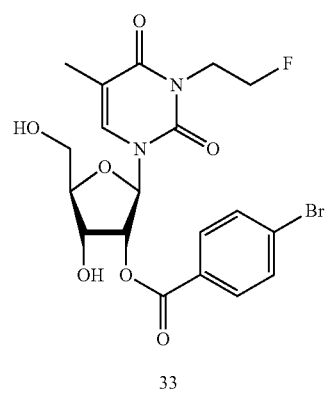
31

4-bromobenzoyl
chloride,
——————→
TEA, DCM

32

2-fluorobromoethane,
Cs₂CO₃, DMF,
60 C.
→

33

MeOH, NH₄OH
→

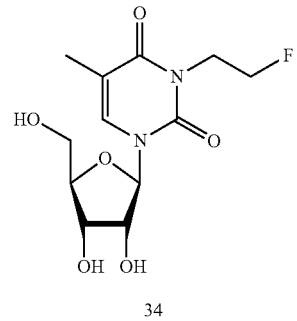
34
TA-8
¹⁹F-standard

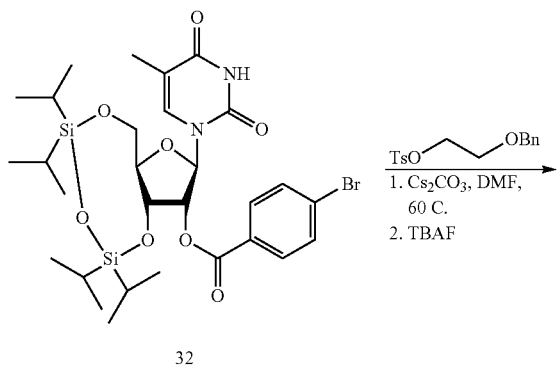

32

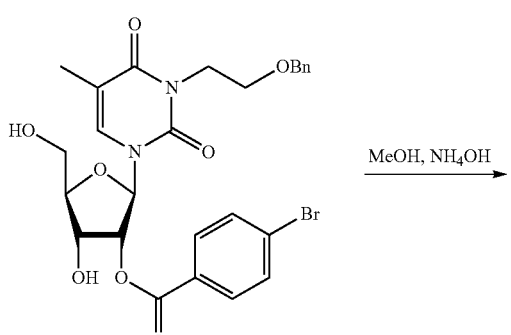

35

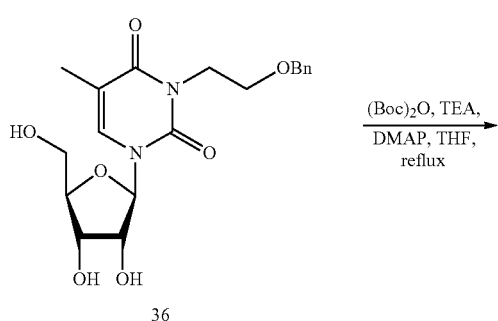

36

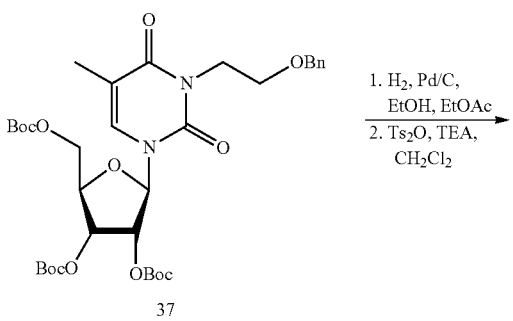

37

TsO⌒OBn
1. Cs₂CO₃, DMF, 60 C.
2. TBAF

MeOH, NH₄OH (Boc)₂O, TEA,
DMAP, THF,
reflux

1. H₂, Pd/C, EtOH, EtOAc
2. Ts₂O, TEA, CH₂Cl₂

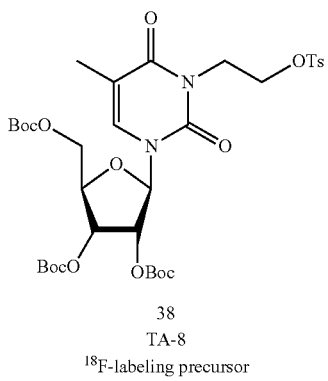

38
TA-8
¹⁸F-labeling precursor

Synthesis of B: To a round bottom flask containing (S)-2-azido-3-methylbutanoic acid (1 equiv) in DMF (5 mL) was treated with HOBt (1.2 equiv) and EDC (1.2 equiv) at room temperature. After stirring for 2 hrs, a solution of (4-fluoro-pyridin-2-yl)methanamine (1.0 equiv) in DMF (2 mL) and DIPEA (1.2 equiv) was added to the reaction mixture and stirred for 2 hrs. The reaction was then poured into water (50 mL) and extracted with EtOAc (20×3 mL). The combined organics were washed with water (10 mL), brine (10 mL) and dried over MgSO₄. The solvent was removed in vacuo, and the product was isolated by chromatography on silica gel using EtOAc:Hexanes as eluent (yield not determined). The purified material was dissolved in DCM (10 mL), triethylamine (1.2 equiv) followed by the addition of a catalytic amount of DMAP and Boc₂O (1.2 equiv). The reaction was stirred overnight at RT. The reaction was concentrated and purified by flash chromatography over silica gel to afford the product A as a white solid (yield not determined).

Synthesis of 9: Alkyne 3 (0.12 g, 0.25 mmol) and the azide (0.10 g, 0.25 mmol) were dissolved in t-BuOH (1.2 mL). To this mixture, copper sulfate (0.04 M in water, 0.63 mL) and sodium ascorbate (0.1 M in water, 0.5 mL) were added and the reaction stirred at room temperature. After 18 hrs, the reaction was worked up using water and ethyl acetate. The organic layer was dried over MgSO₄. The material was purified over silica gel using hexanes:ethyl acetate as the eluent to afford a yellow-colored solid (yield not determined).

¹H NMR (Acetone d6) (δ ppm) 8.82 (d, 1H), 8.07 (d, 1H,), 8.00 (m, 2H), 7.61 (d, 1H), 6.74 (d, 1H), 6.37 (dd, 1H), 5.21 (m, 5H), 4.36 (m, 3H), 2.84 (s, 3H), 2.62 (m, 1H), 2.44 (m, 2H), 1.47 (s, 18H), 1.4 (w, 9H), 1.05 (d, 3H), 0.78 (d, 3H).

LC/MS: Expected for $C_{39}H_{54}N_8O_{14}$: 858.38; found: 859.3 (M+H).

Synthesis of 3: A solution of alkyne 2 (1 equiv) and B (1 equiv) in t-BuOH:H₂O (1:1, 2.5 mL) was treated with CuSO₄·5H₂O (0.01 equiv) and sodium ascorbate (0.1 equiv). After stirring the reaction mixture for 1 hr at room temperature, the organic solvent was removed under vacuum. The residue was dissolved in CH₂Cl₂ (50 mL) and consecutively washed with H₂O (20 mL), brine (20 mL) and dried over MgSO$_4$. The solvent was concentrated in vacuo, and 3 was isolated as pure white solid (100%).

$^1$H NMR (CDCl$_3$, 300 MHz): δ 7.8 (s, 1H), 7.45 (s, 1H), 7.2-7.1 (m, 2H), 6.8-6.95 (m, 2H), 6.21 (t, 1H, J=6.0 Hz), 5.20 (s, 2H), 4.72 (d, 1H, J=9.9 Hz), 4.36 (d, 2H, J=6.0 Hz), 3.95-3.97 (m, 1H), 3.84-3.86 (m, 2H), 3.49 (s, 3H), 2.55-2.52 (m, 1H), 2.32 (t, 2H, J=6.0 Hz), 2.17 (s, 3H), 1.0 (d, 3H, J=6.6 Hz), 0.74 (d, 3H, J=6.6 Hz).

TA-4
Scheme:

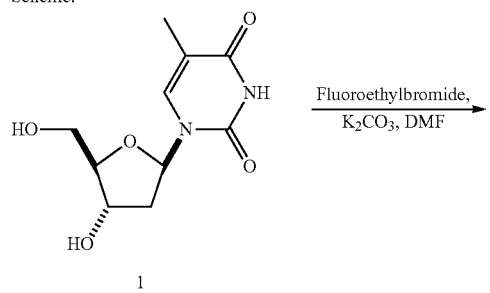

1

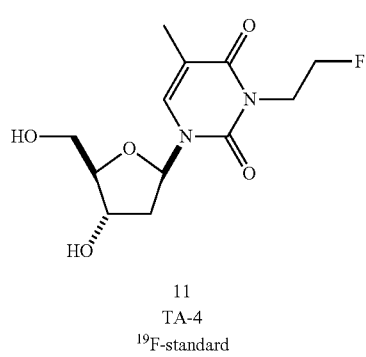

11
TA-4
$^{19}$F-standard

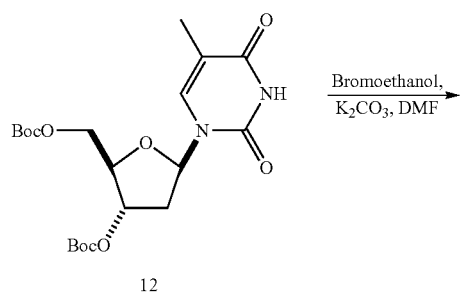

12

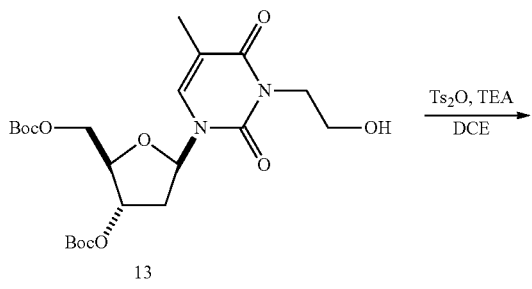

13

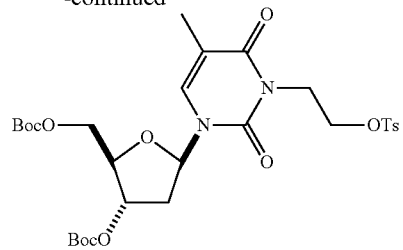

14
TA-4
$^{18}$F-labeling precursor

Synthesis of 11: To a round bottom flask containing thymidine (242 mg, 1 mmol) in DMF (10 mL) and K$_2$CO$_3$ (200 mg) was added fluoroethylbromide (152 mg, 1.2 mmol). The reaction was stirred at RT overnight. The reaction was then poured onto water (60 mL) and extracted into EtOAc (3×30 mL). The combined organics were washed with water (5×20 mL), dried over MgSO$_4$, filtered and concentrated to dryness to afford 180 mg (63%) of a white solid. The material was used without further purification.

$^1$H NMR (CD$_3$OD, 400 MHz): δ 7.85 (s, 1H), 6.31 (t, 1H, J=6.8 Hz), 4.65 (t, 1H, J=5.2 Hz), 4.53 (t, 1H, J=5.2 Hz), 4.39-4.41 (m, 1H), 4.29 (t, 1H, J=5.2 Hz), 4.23 (t, 1H, J=5.2 Hz), 3.91 (dd, 1H, J=3.6, 3.2 Hz), 3.80 (dd, 1H, J=11.6, 3.2 Hz), 3.73 (dd, 1H, J=11.6, 3.2 Hz), 2.27 (ddd, 1H, J=6.8, 3.6 and 2.4 Hz), 2.21-2.23 (m, 1H), 1.90 (s, 3H).

LC/MS (ESI) (m/z): Expected for C$_{12}$H$_{17}$FN$_2$O$_5$: 288.11; found: 289.2 (M+H).

Synthesis of 13: To a round bottom flask containing 3',5'-di-O-boc thymidine (320 mg, 2.54 mmol), DMF (10 mL) and K$_2$CO$_3$ (500 mg) was added 2-bromoethanol (476 mg, 3.8 mmol). The reaction was stirred at RT overnight. The reaction was poured into water (50 mL) and extracted into EtOAc (3×20 mL). The combined organics were washed with water (5×20 mL), dried over MgSO$_4$, filtered and concentrated to dryness. The crude material was used for next step.

LC/MS (ESI) (m/z): Expected for C$_{22}$H$_{34}$N$_2$O$_{10}$: 486.22; found: 487 (M+H)

Synthesis of 14: To a round bottom flask containing 3-N-(2-hydroxyethyl)-3'-5'-di-O-boc thymidine (276 mg, 0.57 mmol), 1,2-dichloroethane (10 mL) and triethylamine (158 uL, 1.14 mmol) was added para-toluene sulfonic anhydride (278 mg, 0.85 mmol). The reaction stirred at RT overnight. The reaction was diluted with DCM (50 mL), washed with water (20 mL), dried over MgSO$_4$, filtered and concentrated to dryness. The crude material was purified on silica gel using a gradient of hexanes and ethyl acetate to afford 175 mg (48%) of a white solid.

$^1$H NMR (CDCl$_3$, 300 MHz): δ 7.75 (d, 2H, J=6.0 Hz), 7.42 (s, 1H), 7.30 (d, 2H, J=6.0 Hz), 6.41 (q, 1H, J=5.7, 2.7 Hz), 5.14 (q, 1H, J=1.8, 2.7 Hz), 4.40 (d, 1H, J=3.6 Hz), 4.27-4.34 (m, 4H), 4.20-4.27 (m, 2H), 2.46-2.48 (m, 1H), 2.43 (s, 3H), 2.23-2.24 (m, 1H), 1.90 (s, 3H), 1.51 (s, 18H).

LC/MS (ESI) (m/z): Expected for C$_{29}$H$_{40}$N$_2$O$_{12}$S: 640.23; found: 641 (M+H).

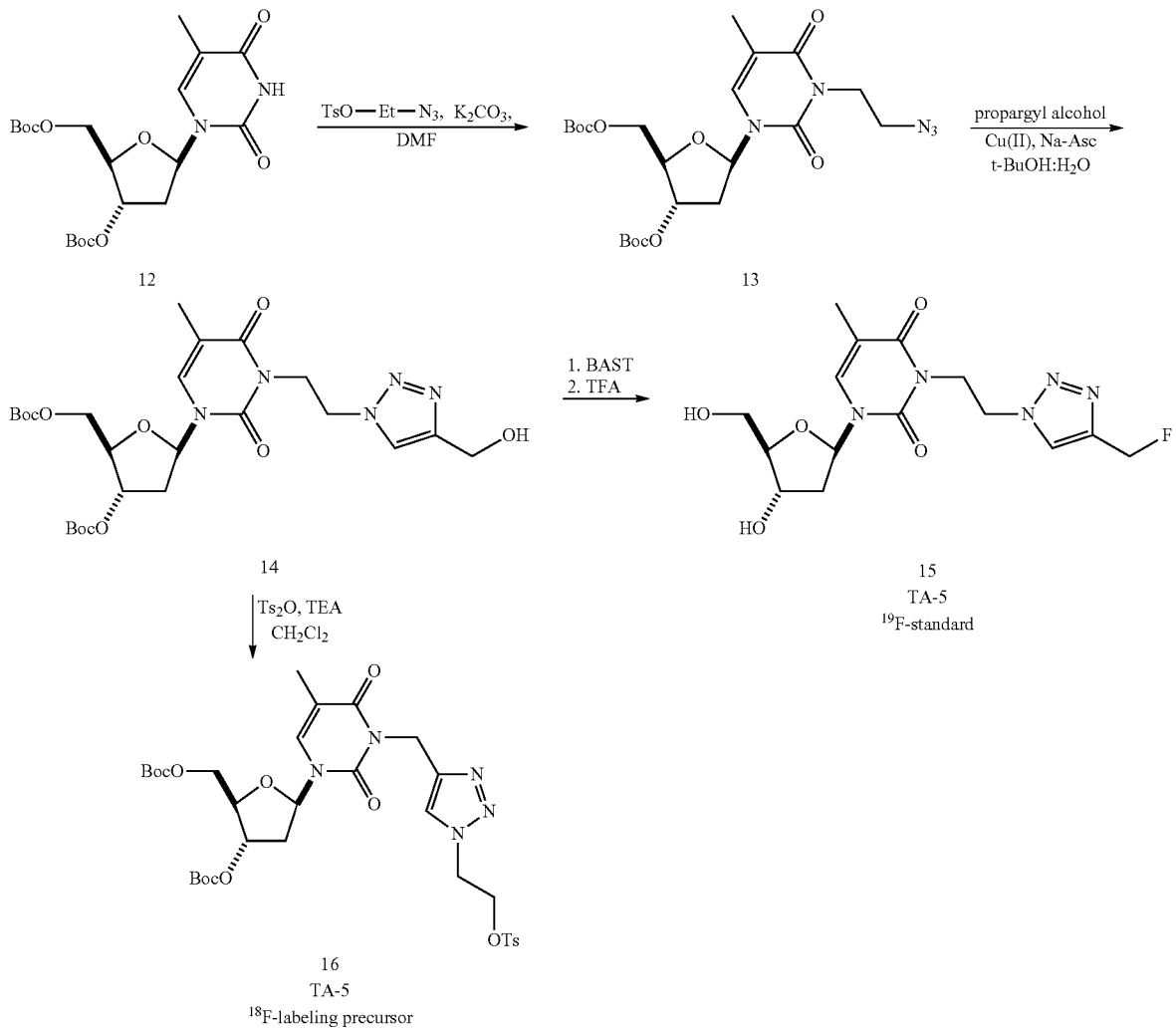

TA-5 Scheme:

12

13

14

15
TA-5
¹⁹F-standard

16
TA-5
¹⁸F-labeling precursor

Synthesis of 13: To a round bottom flask containing 12 (221 mg, 0.5 mmoles), DMF (5 mL) and K$_2$CO$_3$ (500 mg, 3.61 mmoles) was added tosylethylazide (181 mg, 0.75 mmoles) and the reaction was stirred at 50° C. for 3 hrs. The reaction mixture was then poured into water (50 mL) and extracted with EtOAc (50×3 mL). The combined organics were washed with water (20 mL), brine (20 mL) and dried over MgSO$_4$. Purification of the residue by flash chromatography over silica gel afforded 13 as a yellow oil (100% yield).
$^1$H NMR (CDCl$_3$, 300 MHz) δ: 7.47 (s, 1H), 6.43-6.50 (m, 1H), 5.12-5.18 (m, 1H), 4.15-4.40 (m, 5H), 3.45-3.55 (m, 3H), 2.23-2.24 (m, 1H), 1.96 (s, 3H), 1.51 (s, 18H).

Synthesis of 14: A solution of azide (256 mg, 0.5 mmoles) and propargyl alcohol (56 mg, 1 mmoles) in t-BuOH:H$_2$O (1:1, 2.5 mL) was treated with CuSO$_4$.5H$_2$O (0.04M, 200 uL) and sodium ascorbate (0.1M, 200 uL). After stirring the reaction mixture for 1 hr at room temperature, the reaction was deemed incomplete. To the reaction was added sodium ascorbate (0.1M, 200 uL). After 3 hrs, the organic solvent was removed under vacuum, the residue dissolved in CH$_2$Cl$_2$ (50 mL) and consecutively washed with H$_2$O (20 mL), brine (20 mL) and dried over MgSO$_4$. The solvent concentrated in vacuo and the material was purified over silica gel using EtOAc:Hex as the eluent to afford 283 mg of 14 (99% yield) as white solid.

$^1$H NMR (CDCl$_3$, 300 MHz) δ: 7.57 (s, 1H), 7.47 (s, 1H), 6.28-6.33 (m, 1H), 5.08-5.13 (m, 1H), 4.25-4.80 (m, 1H), 2.23-2.24 (m, 1H), 1.96 (s, 3H), 1.51 (s, 18H).
LC/MS (ESI) (m/z): Expected for C$_{25}$H$_{37}$N$_5$O$_{10}$: 567.25; found: 568.2 (M+H), 590.2 (M+Na).

Synthesis of 16: To a round bottom flask containing 14 (1 equiv) in DCM (20 mL) was treated with triethylamine (2 equiv) and p-toluene sulfonic anhydride (1.5 equiv). The reaction mixture was stirred for 2 hrs, silica added to the reaction mixture, solvent evaporated and purified by chromatography on silica gel to give the compound 16 as white solid (yield not determined).

Synthesis of 15: To a round bottom flask containing 14 (283 mg, 0.5 mmoles) in CH$_2$Cl$_2$ (10 mL) and added bis(2-methoxyethyl)aminosulfur trifluoride (275 uL, 1.25 mmoles) dropwise at −76° C. over 10 min. After addition, the temperature was raised to RT. After stirring for 2 hrs, the reaction mixture was quenched with saturated NaHCO$_3$ (10 mL), the organic layer was consecutively washed with H$_2$O (10 mL), brine (10 mL) and dried over MgSO$_4$. The solvent removed under vacuum, and the product was isolated by chromatography on silica gel as white solid (yield not determined). To the residue, at 0° C., was added TFA (2 mL) and the reaction mixture was stirred for 3 hrs. The TFA was removed under vacuum and the residue was purified using 10% MeOH:DCM as the eluent to afford 54.3 mg (60% yield) of a white solid.

$^1$H NMR (DMSO-d6, 400 MHz) δ: 8.13 (s, 1H), 7.79 (s, 1H), 6.11 (t, 1H, J=6.0 Hz), 5.49 (s, 1H), 5.33 (s, 1H), 5.25 (d, 1H, J=3.0 Hz), 5.07 (t, 1H, J=6.0 Hz), 4.61 (t, 2H, J=5.2 Hz), 4.23 (d, 2H, J=5.2 Hz), 3.77 (d, 1H, J=3.2 Hz), 3.65-3.4 (m, 3H), 2.07-2.11 (m, 2H), 1.79 (s, 3H).

Ta-6
Scheme:

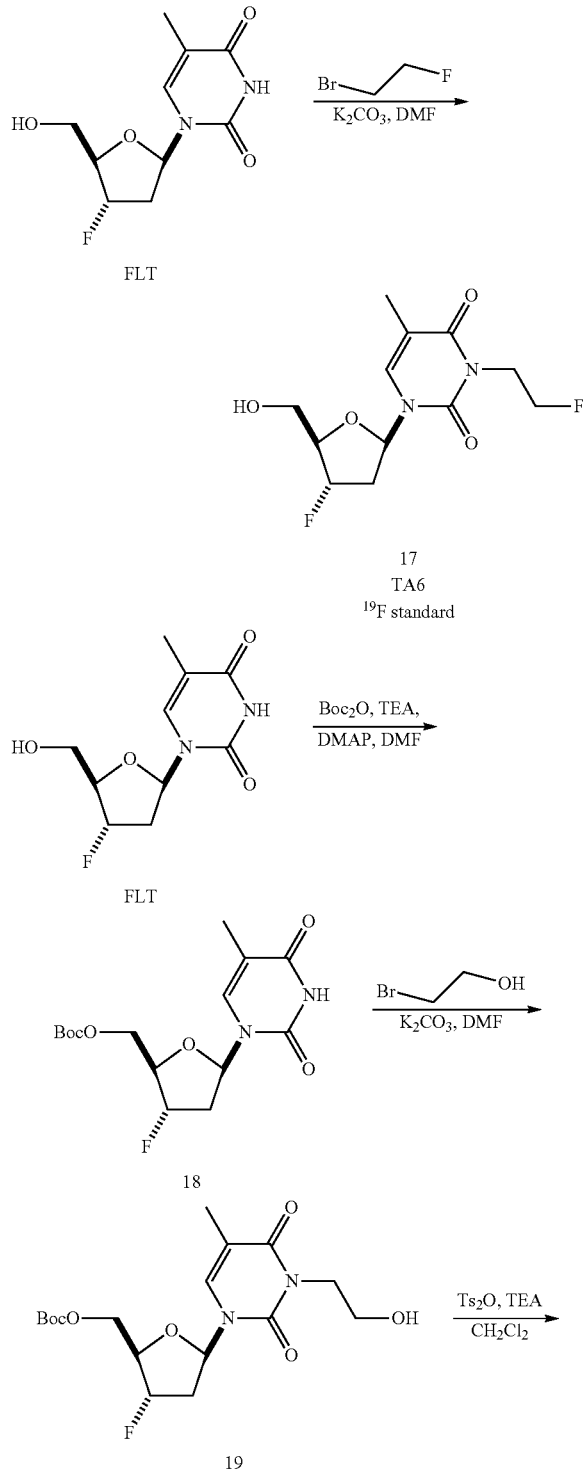

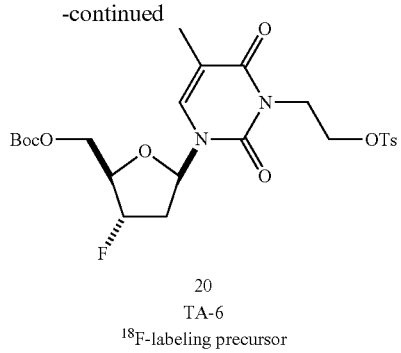

20
TA-6
$^{18}$F-labeling precursor

Synthesis of 17: To a round bottom flask under Ar containing FLT (244 mg, 1.0 mmol) in DMF (10 mL) was added K$_2$CO$_3$ (200 mg, 1.45 mmol) and 2-fluorobromoethane (152 mg, 1.2 mmol). The reaction was stirred at RT overnight. The reaction was then poured onto brine (50 mL) and the product was extracted into EtOAc (3×50 mL). The organics were combined, dried (MgSO$_4$), filtered and concentrated to dryness to afford 200 mg (69%) of clear, colorless oil.

$^1$H NMR (CDCl$_3$, 300 MHz) δ: 7.38 (s, 1H), 6.13-6.20 (m, 1H), 5.45-5.22 (m, 1H), 4.25-4.55 (m, 5H), 3.82-3.95 (m, 2H), 2.80-2.85 (m, 1H), 2.45-2.62 (m, 2H), 1.95 (s, 3H).

LC/MS: Expected for C$_{12}$H$_{16}$FN$_2$O$_4$: 290.11; found: 291.1 (M+H).

Synthesis of 18: To a round bottom flask containing FLT (1 equiv) in DMF (20 mL), triethylamine (1.2 equiv), catalytic amount of DMAP and Boc$_2$O (1.2 equiv) were added and stirred overnight at RT. The reaction was then poured into water (60 mL) and extracted with EtOAc (3×30 mL). The combined organics were washed with water (20 mL), brine (20 mL) and dried over MgSO$_4$. Purification of the residue by silica gel flash chromatography gave the product 18 as a foamy white solid (57%).

$^1$H NMR (CDCl$_3$, 300 MHz) δ: 8.25 (s, 1H), 7.44 (d, 1H, J=0.9 Hz), 6.46 (q, 1H, J=5.4, 9 Hz), 5.25 (dd, 1H, J=5.1, 53.4 Hz), 4.13-4.49 (m, 3H), 2.55-2.78 (m, 1H), 2.05-2.35 (m, 1H), 1.94 (d, 3H, J=0.9 Hz), 1.50 (s, 9H).

LC/MS: Expected for C$_{15}$H$_{21}$FN$_2$O$_6$: 344.14; found: 367.3 (M+Na).

Synthesis of 19: To a round bottom flask containing 3 (1 equiv) in DMF (10 mL), K$_2$CO$_3$ (2 equiv) and 2-bromoethanol (1.5 equiv) were added and stirred for 3 hrs at 50° C. The reaction mixture was then poured into water (50 mL) and extracted with EtOAc (3×30 mL). The combined organics were washed with water (20 mL), brine (20 mL) and dried over MgSO$_4$. Purification of the residue by silica gel flash chromatography gave the product 19 as a foamy white solid (yield not determined).

$^1$H NMR (CDCl$_3$, 300 MHz) δ: 7.45 (d, 1H, J=0.9 Hz), 6.46 (q, 1H, J=5.7, 9 Hz), 5.25 (dd, 1H, J=5.1, 53.4 Hz), 4.23-4.50 (m, 5H), 3.85-3.88 (m, 2H), 2.57-2.78 (m, 1H), 2.05-2.35 (m, 1H), 1.96 (d, 3H, J=0.9 Hz), 1.50 (s, 9H).

LC/MS: Expected for C$_{17}$H$_{25}$FN$_2$O$_7$: 388.16; found: 389.1, (M+H), 411.1 (M+Na).

Synthesis of 20: To a round bottom flask containing 19 (1 equiv) in DCM (20 mL) was treated with triethyl amine (2 equiv) and p-toluene sulfonic anhydride (1.5 equiv). The reaction mixture was stirred for 2 hrs, silica added to the reaction mixture, solvent evaporated and purified by chromatography on silica gel to give the compound 20 as white solid (yield not determined).

$^1$H NMR (CDCl$_3$, 300 MHz): δ 7.75 (d, 2H, J=8.1 Hz), 7.38 (s, 1H), 7.32 (d, 2H, J=8.1 Hz), 6.44 (dd, 1H, J=5.7, 9.0 Hz), 5.15-5.34 (m, 1H), 4.21-4.50 (m, 7H), 2.56-2.65 (m, 1H), 2.43 (s, 3H), 2.01-2.22 (m, 1H), 1.91 (s, 3H), 1.57 (s, 9H).

LC/MS (ESI) (m/z): Expected for $C_{24}H_{31}FN_2O_9S$: 542.17; found: 565.1 (M+Na)

TA-7
Scheme:

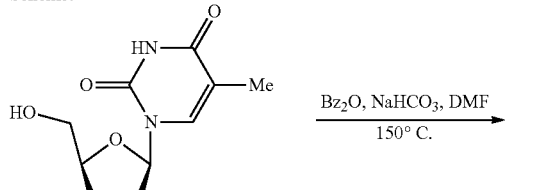
21

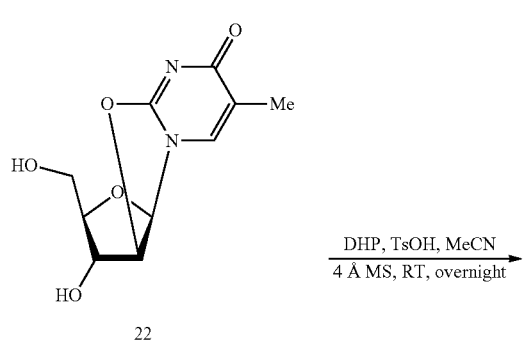
22

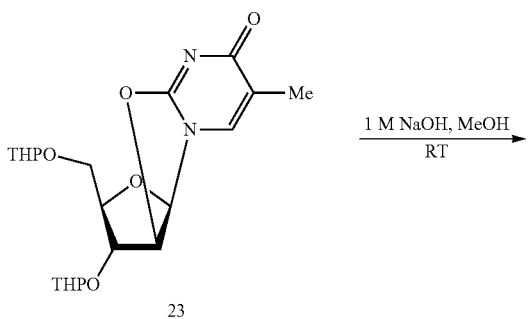
23

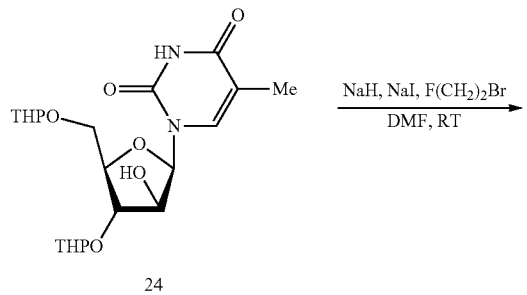
24

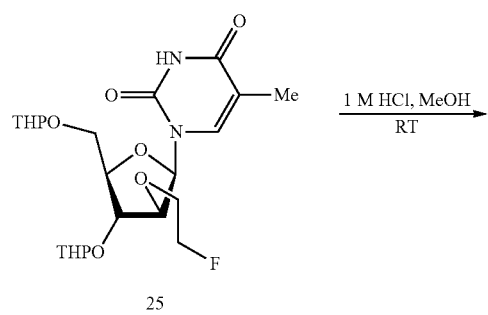
25

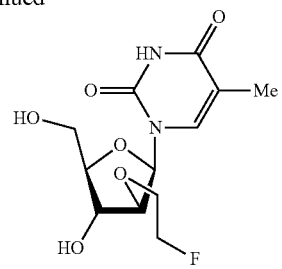
26
TA-7
$^{19}$F-standard

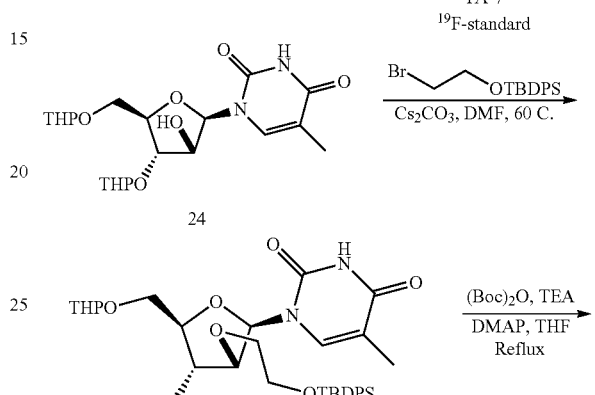

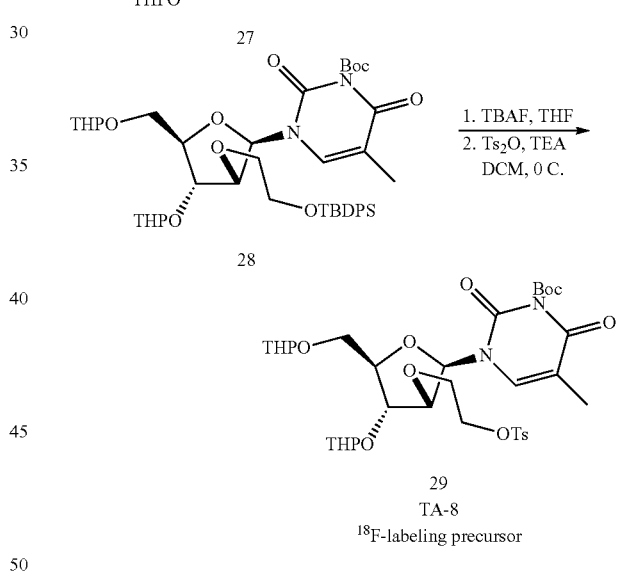
29
TA-8
$^{18}$F-labeling precursor

Synthesis of 22: See: *J. Med. Chem.* 1979, 22, 1273-1277. To a round bottom flask containing 21 (10 g, 38.6 mmol) in DMF 20 mL, was added $(PhO)_2CO$ (12.4 g, 58.05 mmol) and $NaHCO_3$ (0.195 g, 2.32 mmol) and the reaction stirred at 150° C. until $CO_2$ evolution stopped. The reaction mixture was then poured slowly into $Et_2O$ (200 mL). The ether layer was decanted and the residue was washed twice with ether (50 mL). The solid dissolved in hot EtOAc:MeOH:EtOH (4:1:1) mixture, filter and keep cool overnight. A solid separated out, which was filtered and dried to afford 4.36 g (47% yield) of a shiny brown solid.

Synthesis of 23: See: *J. Med. Chem.* 1979, 22, 1273-1277. To a round bottom flask containing 22 (3 g, 12.38 mmol) in MeCN (30 mL) was added 4 A° MS and the reaction stirred for 5 min. To this mixture was added DHP (3.37 mL, 37.15 mmol) followed by a catalytic amount of TsOH. The reaction was stirred at RT overnight. Silica gel was then added to the reaction mixture, the solvent was evaporated and the residue was purified by chromatography on silica gel to give 2.46 g (48% yield) of a yellow oil.

Synthesis of 24: See: *J. Med. Chem.* 1979, 22, 1273-1277. To a round bottom flask containing 23 (2.46 g, 6.03 mmol) in MeOH (12 mL) was added 1M NaOH (5 mL) in MeOH and the reaction was stirred for 6 hrs. After the reaction was deemed complete, silica gel was added. The solvent was evaporated and the residue was purified by chromatography on silica gel to give 2.49 g (97% yield) of a white solid.

Synthesis of 25: To a round bottom flask containing 24 (0.125 g, 0.29 mmol) and NaI (0.087 g, 0.58 mmol) in DMF (1.5 mL), was added NaH (0.035 g, 0.87 mmol) and the reaction was stirred for 10 min. 2-Fluorobromoethane (0.055 g, 0.44 mmol) was added and the reaction stirred at RT overnight. The reaction mixture was then poured into water (20 mL) and extracted with EtOAc (10×3 mL). The combined organics were washed with water (10 mL), brine (10 mL) and dried over MgSO$_4$. Purification of the residue by flash chromatography over silica gel using EtOAc:Hex as the eluent afforded 42 mg (30% yield) of a yellow oil.

$^1$H NMR (CDCl$_3$, 300 MHz): δ 7.45-7.62 (m, 1H), 6.10-6.33 (m, 1H), 3.52-4.85 (m, 15H), 1.95 (br, 3H), 1.5-1.9 (m, 16H).

Synthesis of 26: To a round bottom flask containing 25 (0.042 g, 0.0879 mmol) in MeOH (0.5 mL) was added 1M HCl (0.44 mL) and stirred for 2 hrs. After the reaction is done silica added solvent evaporated and purified by chromatography on silica gel using MeOH:DCM afforded compound 26 (10.8 mg, 40%) as yellow oil.

$^1$H NMR (CD$_3$OD, 300 MHz): δ 7.73 (m, 1H), 6.13 (m, 1H), 4.61-4.67 (m, 1H), 4.46-4.51 (m, 1H), 4.27-4.32 (m, 1H), 4.2-4.24 (m, 1H), 4.14-4.17 (m, 1H), 4.03-4.06 (m, 1H), 3.83-3.92 (m, 1H), 3.78-3.82 (m, 2H), 3.27-3.3 (m, 4H), 1.89-1.9 (m, 3H).

Synthesis of 27: To a round bottom flask containing 24 (1.5 g, 2.83 mmol), in DMF (10 mL), Cs$_2$CO$_3$ (2.03 g, 6.22 mmol) and (2-bromoethoxy) (tert-butoxy)diphenylsilane (2.6 g, 6.78 mmol) were added and stirred for 7 hrs at 60° C. The reaction mixture was then poured into water (100 mL) and extracted with EtOAc (50×3 mL). The combined organics were washed with water (30 mL), brine (30 mL) and dried over MgSO$_4$. Solvent evaporated and used for the next step.

Synthesis of 28: To a round bottom flask containing 7 (0.5 g, 0.69 mmol) in THF (5 mL), triethylamine (0.19 mL, 0.726 mmol), catalytic amount of DMAP and Boc$_2$O (0.3 g, 1.38 mmol) were added and refluxed for 2 hrs. The reaction mixture was concentrated to dryness and used for next step without further purification.

Synthesis of 29: To a round bottom flask containing 28 (0.34 g, 0.412 mmol) in THF (5.8 mL), 1 M TBAF in THF (1.65 mL) was added and stirred for 3 hrs. The reaction mixture was concentrated on silica and purified by silica gel flash chromatography gave the product as a white solid (178 mg, 76%). The white solid (0.178 g, 0.312 mmol) was dissolved in DCM (2 mL), was treated with triethylamine (0.35 mL, 0.624 mmol) and p-toluene sulfonic anhydride (0.122 g, 0.375 mmol). The reaction mixture was stirred for 2 hrs, silica added to the reaction mixture, solvent evaporated and purified by chromatography on silica gel using EtOAc:Hex as the eluent to give the compound 29 (220 mg, 97%) as white solid.

LC/MS (ESI) (m/z): Expected for C$_{34}$H$_{48}$N$_2$O$_{13}$S: 724.29; found: 747.3 (M+Na).

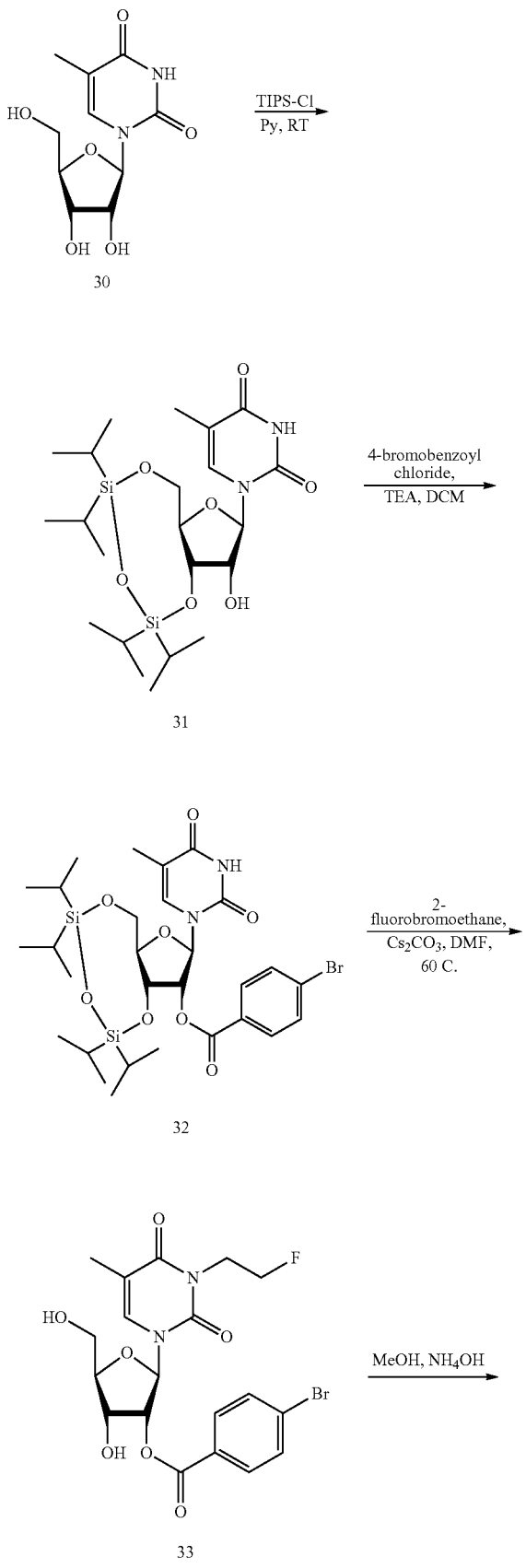

TA-8 Scheme:

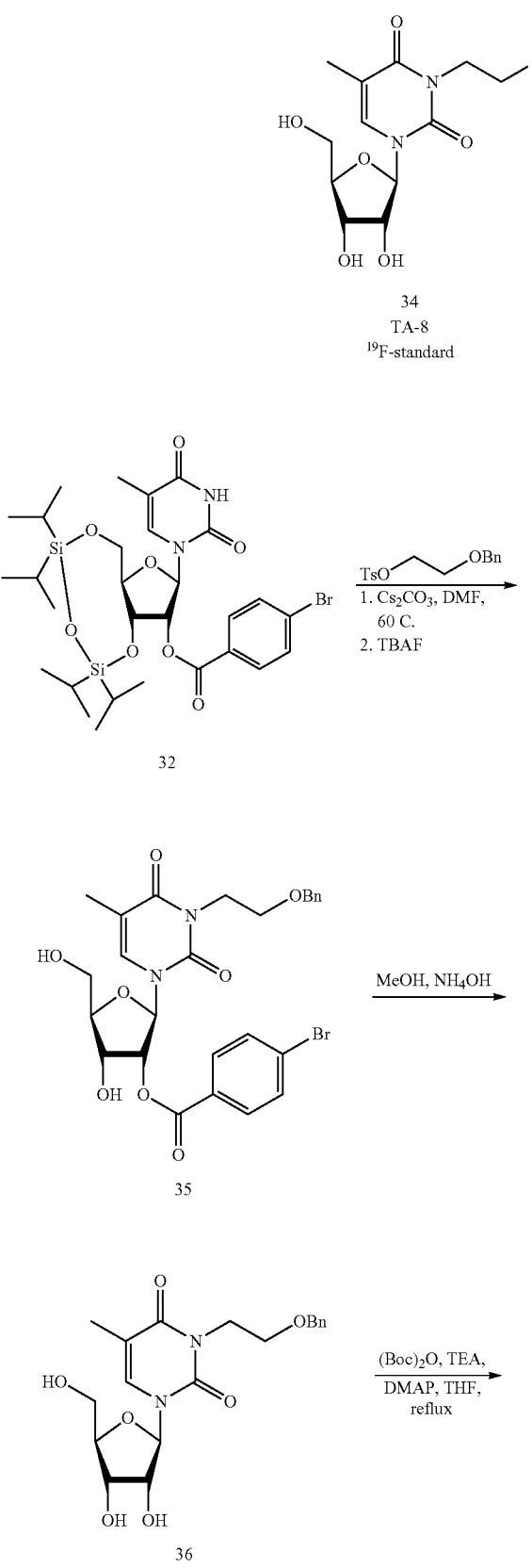

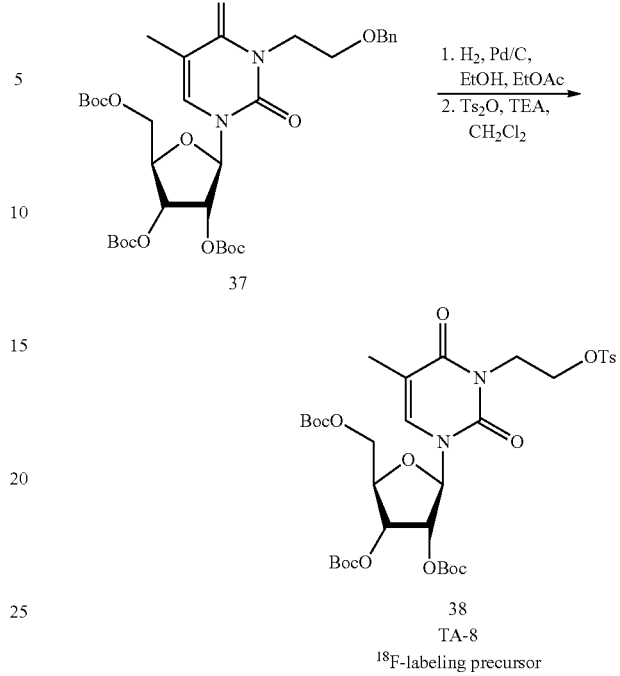

Synthesis of 31: See JACS, 1983, 105, 4059-4065. To a round bottom flask containing 30 (2 g, 7.75 mmol) in pyridine (20 mL) treated with TIPS-Cl (2.97 mL, 9.29 mmol) at room temperature. After stirring for 1 hr, the reaction mixture was diluted with DCM (100 mL), washed with water (30 mL), 1M HCl (30 mL), water (30 mL), sat NaHCO$_3$ (30 mL), brine (30 mL) and dried over MgSO$_4$. The solvent removed in vacuo, and the compound 31 (2.39 g, 62%) was isolated by chromatography on silica gel as sticky oil.

Synthesis of 32: To a round bottom flask under Ar containing di-silylated thymidine (500 mg, 1.0 mmol) in DCM (10 mL) at 0° C. was added TEA (0.18 ml, 1.3 mmol) and 4-bromobenzoyl chloride (263 mg, 1.2 mmol). The reaction was stirred at RT overnight. The reaction was concentrated to dryness. The crude reaction mixture was purified on a Combiflash system using EtOAc:Hex as the eluent to afford 420 mg (61%) of a clear, colorless oil.

$^1$H NMR ((CDCl$_3$, 300 MHz) δ: 7.75 (d, J=4.5 Hz, 2H), 7.62 (d, J=4.5 Hz, 2H), 7.52 (s, 1H), 5.72 (s, 1H), 4.37-4.45 (m, 1H), 4.18-4.25 (m, 2H), 3.95-4.15 (m, 2H), 3.41 (br s, 1H), 1.95 (s, 3H), 0.8-1.17 (m, 28H).

LC/MS: Expected for C$_{29}$H$_{43}$BrN$_2$O$_8$Si$_2$: 682.17; found: 683.2, 685.2 (M+H).

Synthesis of 33: To a round bottom flask under Ar containing di-silylated benzoylated thymidine (100 mg, 0.146 mmol) in DMF (5 mL) at 60° C. was added Cs$_2$CO$_3$ (143 mg, 0.44 mmol), NaI (2 mg) and 2-fluorobromoethane (28 mg, 0.22 mmol). The reaction was stirred at 60° C. for 5 hrs. The reaction was concentrated to dryness. The crude reaction mixture was purified on a Combiflash system using EtOAc:Hex as the eluent to afford 29 mg (41%) of a clear, colorless oil.

$^1$H NMR ((CDCl$_3$, 300 MHz) δ: 7.85 (d, J=4.5 Hz, 2H), 7.60 (d, J=4.5 Hz, 2H), 7.32 (s, 1H), 5.70 (d, J=1.2 Hz, 1H), 4.67-4.83 (m, 2H), 4.42-4.56 (m, 3H), 4.2-4.4 (m, 5H), 3.22 (br s, 1H), 1.65 (s, 3H).

LC/MS: Expected for C$_{19}$H$_{20}$BrFN$_2$O$_7$: 486.04: found: 487.00, 489.00 (M+H).

Synthesis of 34: To a round bottom flask containing the thymidine derivative (29 mg) and MeOH (5 mL) at 0° C. was added NH$_4$OH (conc., 1 mL). The reaction was then warmed to RT and stirred for 4 hrs. The reaction was concentrated to dryness and filtered through a plug of silica using EtOAc as the eluent to afford 1.8 mg (18%) of clear, colorless oil.

$^1$H NMR ((CDCl$_3$, 300 MHz) δ: 7.45 (s, 1H), 5.62 (d, J=1.2 Hz, 1H), 4.72-4.76 (m, 1H), 4.55-4.58 (m, 1H), 4.2-4.5 (m, 5H), 3.95-4.05 (m, 1H), 3.75-3.86 (m, 2H), 2.95 (br s, 1H), 2.33 (br s, 1H), 1.95 (s, 3H).

LC/MS: Expected for C$_{12}$H$_{17}$FN$_2$O$_6$: 304.11; found: 305.1 (M+H), 327.1 (M+Na).

Synthesis of 35: To a round bottom flask under Ar containing di-silylated benzoylated thymidine (1.1 gm, 1.61 mmol) in DMF (16 mL), Cs$_2$CO$_3$ (0.65 g, 1.93 mmol) and 2-(benzyloxy)ethyl 4-methylbenzenesulfonate (0.59 g, 1.93 mmol) were added. The reaction was stirred at 60° C. for 4 hrs. The reaction mixture was then poured into water (80 mL) and extracted with EtOAc (50×3 mL). The combined organics were washed with water (30 mL), brine (30 mL) and dried over MgSO$_4$. Crude mixture (1.2 g) was used for next step. Crude product (1.2 g) was dissolved in THF (26 mL) and treated with 1M TBAF in THF (3 mL) at RT and stirred for 1 hr. The reaction was concentrated to dryness and the crude reaction mixture was purified on a Biotage system using MeOH:DCM as the eluent to afford 6 (0.5 g, 59%) as white solid.

LC/MS: Expected for C$_{26}$H$_{27}$BrN$_2$O$_8$: 574.1; found: 576.1 (M+2H), 577.1 (M+3H), 597.1 (M+Na).

Synthesis of 36: To a round bottom flask containing 35 (0.25 g, 0.434 mmol) in MeOH (4.5 mL), was added NH$_4$OH (4 mL). The reaction was stirred for 5 hrs. The reaction was concentrated to dryness and purified on Biotage using MeOH:DCM as eluent to afford 36 (0.162 g, 95%) as white solid.

$^1$H NMR ((CDCl$_3$, 300 MHz) δ: 7.5 (s, 1H), 7.25-7.4 (m, 5H), 5.75 (d, J=1.2 Hz, 1H), 4.55 (s, 2H), 3.72-4.35 (m, 9H), 3.45 (s, 2H), 1.95 (s, 3H).

LC/MS: Expected for C$_{19}$H$_{24}$N$_2$O$_7$: 392.16; found: 393.1 (M+H), 415.1 (M+Na).

Synthesis of 37: To a round bottom flask containing 36 (0.45 g, 1.15 mmol) in THF (10 mL), triethylamine (0.96 mL, 6.88 mmol), catalytic amount of DMAP and Boc$_2$O (1.5 g, 6.88 mmol) were added and refluxed for 2 hrs. The reaction was concentrated to dryness and the crude reaction mixture was purified on a Biotage system using EtOAc:Hex as the eluent to afford 37 (250 mg, 32%) as a white solid.

$^1$H NMR ((CDCl$_3$, 300 MHz) δ: 7.25-7.45 (m, 6H), 6.12 (d, J=1.2 Hz, 1H), 5.21-5.3 (m, 2H), 4.6 (s, 2H), 4.35-4.55 (m, 3H), 4.2-4.31 (m, 2H), 3.71-3.82 (m, 2H), 1.97 (s, 3H), 1.50-1.51 (m, 27H).

LC/MS: Expected for C$_{34}$H$_{48}$N$_2$O$_{13}$: 692.32; found: 715.3 (M+Na).

Synthesis of 38: A solution of 37 (0.25 g) in EtOAc:EtOH (5:3, 8 mL) was added to the hydrogenation flask. To this Pd/C (25 mg) was added and hydrogenated at 50 psi for 4 hrs. The reaction mixture was filtered through celite, washed with EtOH and was concentrated to dryness to get the debenzoylated product as a white solid (0.21 g, 97%). This solid was dissolved in DCM (2 mL) and treated with triethylamine (0.11 mL, 0.7 mmol) and p-toluene sulfonic anhydride (0.15 g, 0.42 mmol). The reaction mixture was stirred for 2 hrs, silica added to the reaction mixture, solvent evaporated and purified by chromatography on silica gel to give compound 38 (200 mg, 76%) as white solid.

$^1$H NMR ((CDCl$_3$, 400 MHz) δ: 7.74-7.76 (m, 2H), 7.29-7.36 (m, 3H), 6.05-6.06 (m, 1H), 5.16-5.21 (m, 2H), 4.35-4.41 (m, 3H), 4.25-4.28 (m, 2H), 4.19-4.21 (m, 2H), 2.42 (s, 3H), 1.90 (d, J=1.2 Hz, 3H), 1.50 (s, 9H), 1.49 (s, 9H), 1.47 (s, 9H).

LC/MS: Expected for C$_{34}$H$_{48}$N$_2$O$_{15}$S: 756.28; found: 779.2 (M+Na).

TA-9 Scheme:

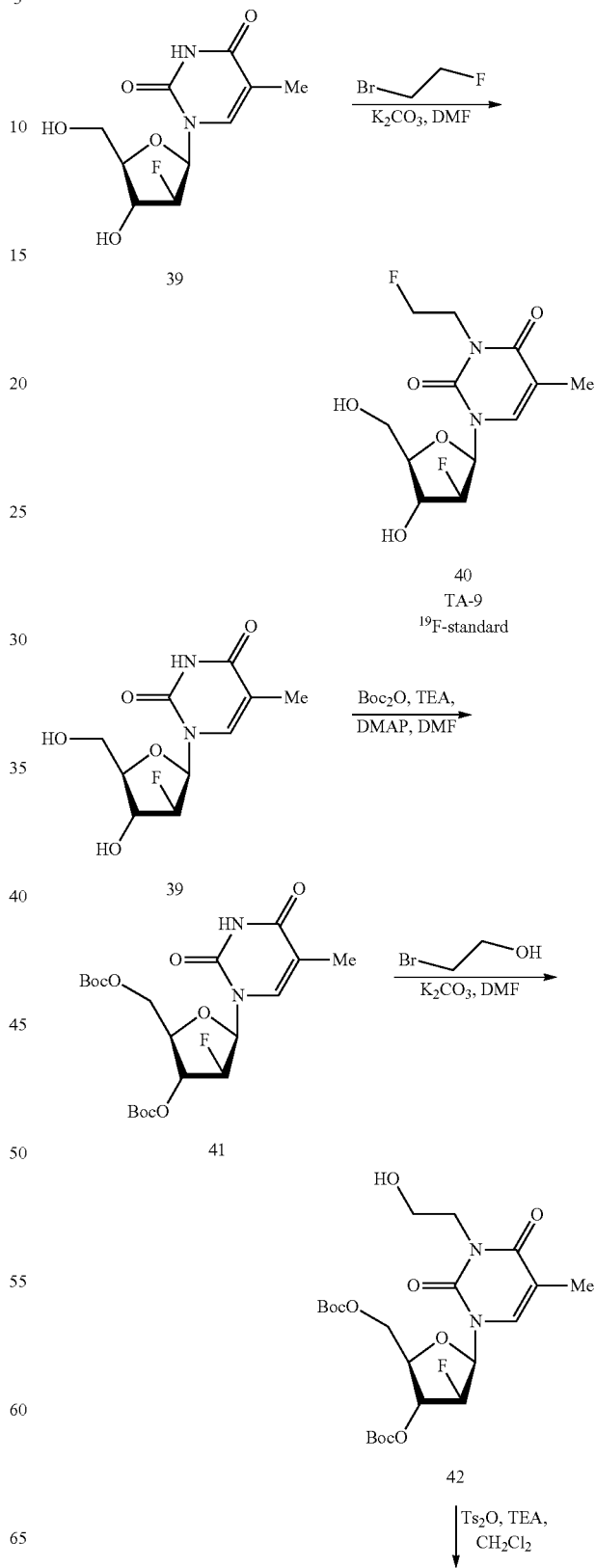

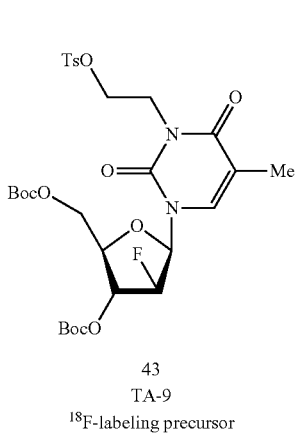

43
TA-9
[18]F-labeling precursor

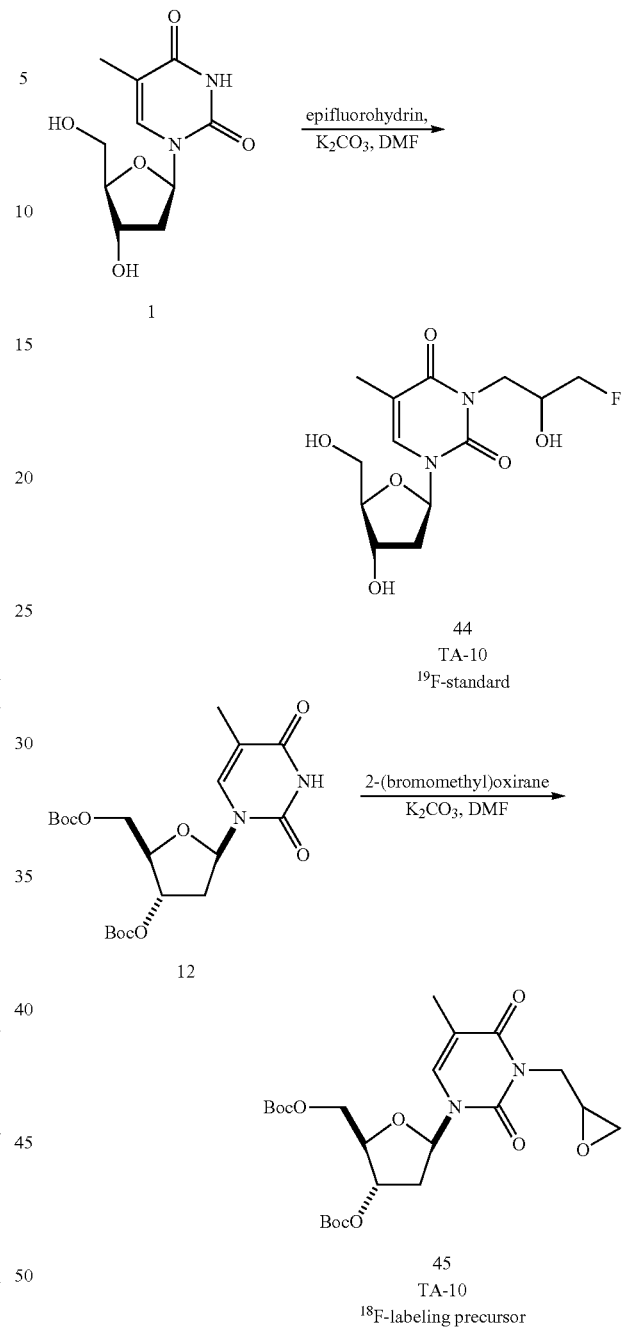

44
TA-10
[19]F-standard

45
TA-10
[18]F-labeling precursor

Synthesis of 40: To a round bottom flask containing 39 (1 equiv) in DMF (10 mL), $K_2CO_3$ (2 equiv) and fluoroethylbromide (1.2 equiv) were added. The reaction mixture was stirred at RT overnight and was then poured into water (50 mL) and extracted with EtOAc (20×3 mL). The combined organics were washed with water (20 mL), brine (20 mL) and dried over $MgSO_4$. Purification of the residue by silica gel flash chromatography gave the product 40 as a foamy white solid (yield not determined).

$^1$H NMR ($CD_3OD$, 300 MHz): δ 7.35-7.36 (m, 1H), 6.27 (dd, 1H, J=18.6, 3.6 Hz), 4.99-5.17 (m, 1H), 4.73 (t, 1H, J=5.1 Hz), 4.57 (t, 1H, J=5.1 Hz), 4.49 (br s, 1H), 4.42 (br s, 1H), 4.36 (t, 1H, J=5.1 Hz), 4.28 (t, 1H, J=5.1 Hz), 3.88-3.93 (m, 3H), 3.24 (br s. 1H), 1.94 (d, 3H, J=1.2 Hz).

Synthesis of 41: To a round bottom flask containing 39 (1 equiv) in DMF (10 mL), triethylamine (3 equiv), catalytic amount of DMAP and $Boc_2O$ (2.2 equiv) were added and stirred overnight at RT. The reaction was then poured into water (50 mL) and extracted with EtOAc (30×3 mL). The combined organics were washed with water (20 mL), brine (20 mL) and dried over $MgSO_4$. The product 41 was used for the next step without purification.

Synthesis of 42: To a round bottom flask containing 41 (1 equiv) in DMF (10 mL), $K_2CO_3$ (2 equiv) and bromo ethanol (1.3 equiv) were added and stirred for 3 hrs at 50° C. The reaction mixture was then poured into water (50 mL) and extracted with EtOAc (30×3 mL). The combined organics were washed with water (20 mL), brine (20 mL) and dried over $MgSO_4$. The product 42 was used for the next step without purification.

Synthesis of 43: To a round bottom flask containing 42 (1 equiv) in DCM (10 mL) was treated with triethylamine (2 equiv) and p-toluene sulfonic anhydride (1.2 equiv). The reaction mixture was stirred for 2 hrs, silica added to the reaction mixture, solvent evaporated and purified by chromatography on silica gel to give the compound 43 (55%) as white solid.

$^1$H NMR ($CDCl_3$, 300 MHz) δ: 7.70-7.79 (m, 2H), 7.32-7.39 (m, 3H), 6.15-6.28 (m, 1H), 5.14-5.35 (m, 2H), 4.31-4.65 (m, 7H), 2.61 (s, 3H), 2.1 (s, 3H), 1.65-1.85 (m, 18H).

LC/MS: Expected for $C_{29}H_{39}FN_2O_{12}S$: 658.22; found: 681.2 (M+Na).

Synthesis of 44: To a round bottom flask under Ar containing thymidine (242 mg, 1.0 mmol) in DMF (10 mL) was added $K_2CO_3$ (200 mg, 1.45 mmol) and epifluorohydrin (91.2 mg, 1.2 mmol). The reaction was stirred at RT overnight. The reaction was then poured onto brine (50 mL) and the product was extracted into EtOAc (3×30 mL). The organics were combined, dried over $MgSO_4$, filtered and concentrated to dryness to afford 150 mg (47%) of clear, colorless oil.

$^1$H NMR ($CDCl_3$, 300 MHz) δ: 7.45 (s, 1H), 6.19-6.25 (m, 1H), 3.81-4.69 (m, 11H), 3.5 (br s, 1H), 2.30-2.50 (m, 2H), 1.95 (s, 3H).

LC/MS: Expected for $C_{13}H_{19}FN_2O_6$: 318.12; found: 319.2 (M+H), 357.2 (M+K).

Synthesis of 45: To a round bottom flask containing 12 (1 equiv) in DMF (10 mL), K$_2$CO$_3$ (2 equiv) and 2-(bromomethyl)oxirane (1.2 equiv) were added and stirred for 3 hrs at 50° C. The reaction mixture was then poured into water (50 mL) and extracted with EtOAc (30×3 mL). The combined organics were washed with water (20 mL), brine (20 mL) and dried over MgSO$_4$. Purification of the residue by silica gel flash chromatography gave the product 45 as a white solid (yield not determined).

$^1$H NMR (CDCl$_3$, 300 MHz) δ: 7.47 (d, 1H, J=1.2 Hz). 6.46 (q, 1H, J=5.7, 8.4 Hz), 5.13-5.16 (m, 1H), 4.24-4.40 (m, 4H), 4.00-4.06 (m, 1H), 3.49 (s, 8H), 3.24-3.26 (m, 1H), 2.77 (t, 1H, J=9.0 Hz), 2.70 (q, 1H, J=2.7, 5.1 Hz), 2.51 (2dd, 1H, J=2.1, 6.0 Hz), 2.28 (q, 1H, J=6.6, 8.4 Hz), 1.96 (d, 3H, J=0.9 Hz), 1.5 (s, 18H).

TA-11
Scheme:

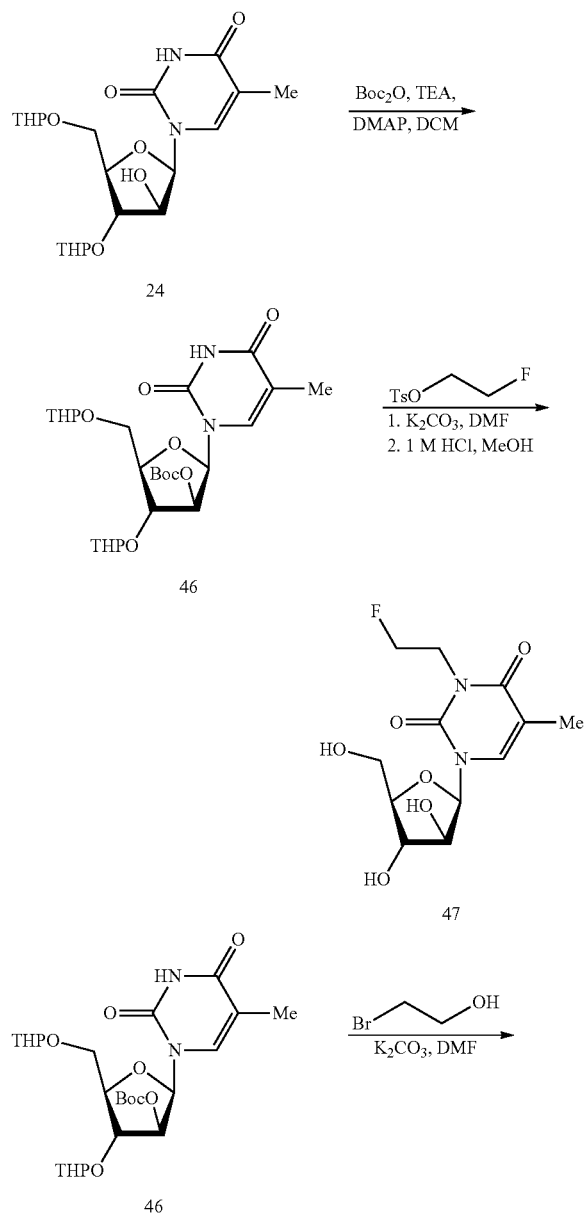

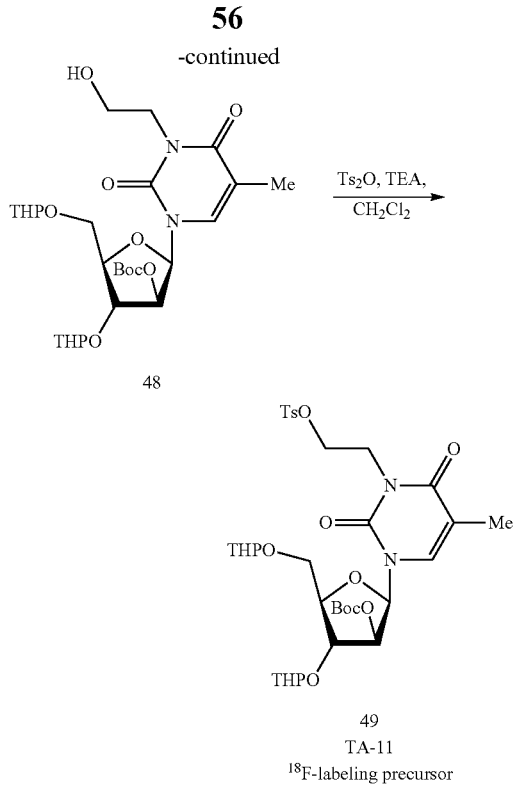

49
TA-11
$^{18}$F-labeling precursor

Synthesis of 46: To a round bottom flask containing 24 (1 equiv) in DCM (10 mL), triethylamine (2 equiv), catalytic amount of DMAP and Boc$_2$O (1.2 equiv) were added and stirred overnight at RT. The reaction was concentrated and used for next step.

Synthesis of 47: To a round bottom flask containing 46 (crude from previous step) in DMF (10 mL), K$_2$CO$_3$ (2 equiv) and 2-fluoroethyl 4-methylbenzenesulfonate (1.5 equiv) were added and stirred for 3 hrs at 50° C. The reaction mixture was then poured into water (50 mL) and extracted with EtOAc (30×3 mL). The combined organics were washed with water (20 mL), brine (20 mL) and dried over MgSO$_4$. Purification of the residue by silica gel flash chromatography gave the product as a white solid. This was dissolved in MeOH (3 mL), 1M HCl (1 mL) was added and stirred for 2 hrs. After the reaction is done silica added solvent evaporated and purified by chromatography on silica gel using MeOH:DCM as the eluent to give compound 47 as white solid (yield not determined).

$^1$H NMR (CD$_3$OD, 300 MHz) δ: 7.76 (d, 1H, J=1.2 Hz), 6.14 (d, 1H, J=4.5 Hz), 4.66 (t, 1H, J=5.4 Hz), 4.51 (t, 1H, J=5.1 Hz), 4.29-4.49 (m, 1H), 4.21-4.25 (m. 1H), 4.05-4.18 (m, 3H). 3.77-3.91 (m, 3H), 3.56-3.63 (m, 2H), 1.86 (s, 3H).

LC/MS: Expected for C$_{12}$H$_{17}$FN$_2$O$_6$: 304.11; found: 305.1 (M+H), 327.1 (M+Na).

Synthesis of 48: To a round bottom flask containing 46 (1 equiv) in DMF (10 mL), K$_2$CO$_3$ (2 equiv) and bromo ethanol (1.2 equiv) were added and stirred for 3 hrs at 50° C. The reaction mixture was then poured into water (50 mL) and extracted with EtOAc (20×3 mL). The combined organics were washed with water (20 mL), brine (20 mL) and dried over MgSO$_4$. The reaction was concentrated and used for next step.

Synthesis of 49: To a round bottom flask containing 48 (crude from previous step) in DCM (20 mL) was treated with triethylamine (1.2 equiv) and p-toluene sulfonic anhydride (1.2 equiv). The reaction mixture was stirred for 2 hrs, silica added to the reaction mixture, solvent evaporated and purified by chromatography on silica gel using EtOAc:Hex as the eluent to give compound 49 as white solid (yield was not determined).

¹H NMR (CDCl₃, 300 MHz) δ: 7.76 (d. 2H, J=8.4 Hz), 7.29-7.36 (m, 3H), 6.22-6.27 (m, 1H), 5.05-5.08 (m, 1H), 4.84 (br s, 1H), 4.70-4.74 (m, 2H), 3.47-4.41 (m, 13H), 2.42 (s, 3H), 1.87-1.88 (m, 3H), 1.63-1.83 (m, 6H), 1.33 (s, 9H), 1.19-1.33 (m, 4H).

LC/MS: Expected for $C_{34}H_{48}N_2O_{13}S$: 724.29, found: 725.3 (M+H), 747.3 (M+Na).

TA-12
Scheme:

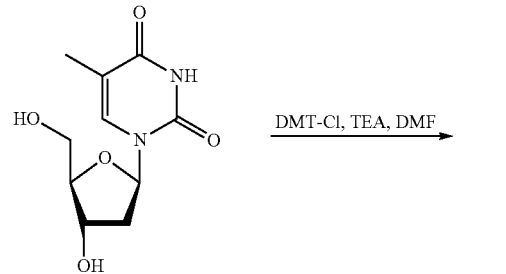

1

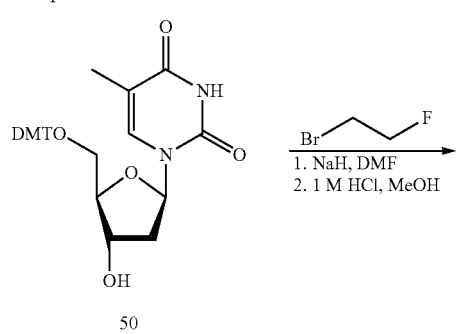

50

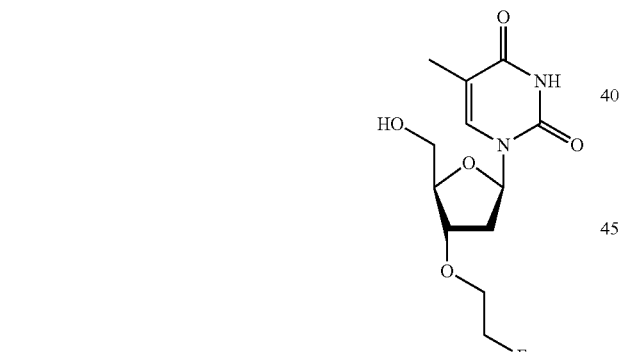

51
TA-12
¹⁹F-standard

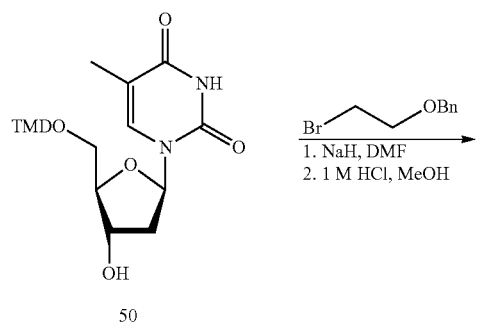

50

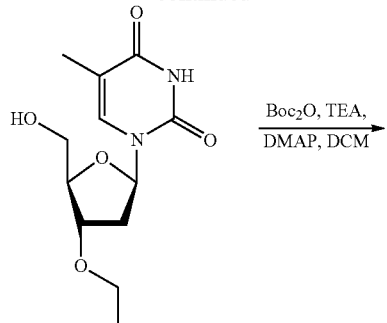

52

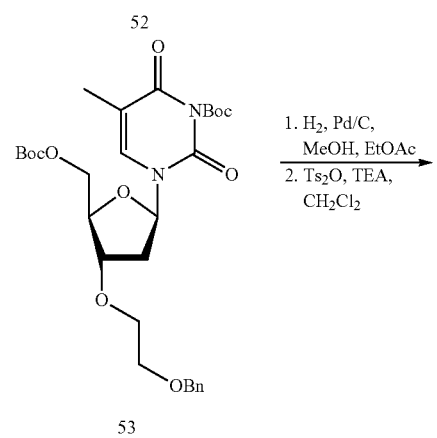

53

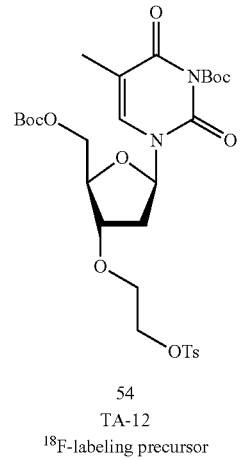

54
TA-12
¹⁸F-labeling precursor

Synthesis of 50: To a round bottom flask containing 1 (1 equiv) in DMF (20 mL), triethylamine (1.2 equiv) and DMT-Cl (1.2 equiv) were added and stirred for 2 hrs at RT. The reaction was then poured into water (100 mL) and extracted with EtOAc (50×3 mL). The combined organics were washed with water (30 mL), brine (30 mL) and dried over MgSO₄. Residue concentrated and used for the next step without further purification.

Synthesis of 51: To a round bottom flask containing 50 (205 mg 0.37 mmol) in DMF (4 mL), NaH (50 mg, 1.11 mmol) was added, stirred for 10 min. To this, F(CH₂)₂Br (70 mg, 0.55 mmol) was added and stirred for overnight at RT. The reaction mixture was then poured into water (50 mL) and extracted with EtOAc (20×3 mL). The combined organics were washed with water (10 mL), brine (10 mL) and dried over MgSO₄. Purification of the residue by silica gel flash chromatography gave the product (81.1 mg, 37%) as yellow oil. This was dissolved in MeOH (5 mL), 1M HCl (2 mL) was added and stirred for 2 hrs. After the reaction is done silica added solvent evaporated and purified by chromatography on silica gel to give the compound 51 (35.8 mg, 92%) as yellow oil.

$^1$H NMR (CDCl$_3$, 400 MHz) δ: 7.48 (d, 1H, J=1.6), 6.10 (q, 1H, J=6.0, 7.6 Hz), 4.54 (t, 1H, J=4.4 Hz), 4.42 (t, 1H, J=4.0 Hz), 4.15-4.18 (m, 1H), 4.01-4.03 (m, 1H), 3.79 (dd, 1H, J=3.2, 12.0 Hz), 3.58-3.78 (m, 3H), 2.98 (br s, 2H), 2.29-2.35 (m, 1H), 2.13-2.20 (m, 1H), 1.82 (d, 3H, J=0.4 Hz).

LC/MS: Expected for C$_{12}$H$_{17}$FN$_2$O$_5$: 288.11; found: 289.2 (M+H).

Synthesis of 52: To a round bottom flask containing 50 (4 g, 7.35 mmol) in DMF (75 mL), NaH (1.76 g, 44.1 mmol) was added and stirred for 10 min. To this, BnO(CH$_2$)$_2$Br (5.8 mL, 34.75 mmol) was added and stirred for 3 hrs at RT. The reaction mixture was then poured into water (500 mL) and extracted with EtOAc (100×3 mL). The combined organics were washed with water (50 mL), brine (50 mL) and dried over MgSO$_4$. Purification of the residue by silica gel flash chromatography gave the product (2.9 g, 58%) as yellow oil. This was dissolved in MeOH (50 mL), 1M HCl (10 mL) was added and stirred for 2 hrs. After the reaction was done, solvent evaporated to dryness and repeatedly washed with Et$_2$O:Hexanes (1:1) to give the compound 52 (100%).

Synthesis of 53: To a round bottom flask containing 51 (1.61 g, 4.27 mmol) in DCM (50 mL), triethylamine (2.5 mL, 17 mmol), catalytic amount of DMAP and Boc$_2$O (2.05 g, 9.39 mmol) were added and stirred overnight at RT. The reaction was concentrated and purified on Biotage using EtOAc:Hexanes as eluent gave the product 53 (1.6 g, 65%) as a foamy white solid.

$^1$H NMR (CDCl$_3$, 400 MHz) δ: 7.41 (d, 1H, J=1.2 Hz), 7.19-7.30 (m, 5H). 6.22 (t, 1H, J=6.8 Hz), 4.48 (s, 2H), 4.20-4.21 (m, 2H), 4.16 (q, 1H, 3.2, 6.4 Hz), 4.01-4.09 (m, 1H), 3.52-3.61 (m, 4H), 2.36-2.42 (m, 1H), 2.01-2.06 (m, 1H), 1.87 (d, 3H, J=1.2 Hz), 1.53 (s, 9H), 1.42 (s, 9H).

Synthesis of 54: A solution of 52 (1.6 g, 2.78 mmol) in EtOAc:MeOH (3:1, 50 mL) was added to the hydrogenation flask. To this Pd/C (0.32 g, 20%) was added and hydrogenated at 50 psi for 2 hrs. The reaction mixture was filtered through celite, washed with MeOH and was concentrated to dryness to get the debenzoylated product (800 mg, 60%) as a white solid. This solid was dissolved in DCM (20 mL) and treated with triethylamine (0.69 mL, 4.938 mmol) and p-toluene sulfonic anhydride (1.07 g, 3.292 mmol). The reaction mixture was stirred for 2 hrs, silica added to the reaction mixture, solvent evaporated and purified by chromatography on silica gel to give the compound 54 (1 g, 95%) as white solid.

$^1$H NMR (CDCl$_3$, 400 MHz) δ: 7.76-7.78 (m, 2H), 7.33-7.39 (m, 3H), 6.14-6.18 (m, 1H). 4.21 (br s, 2H), 4.03-4.15 (m, 5H), 2.43 (s, 3H), 2.7-2.45 (m, 1H), 1.99-2.02 (m, 2H), 1.92 (s, 3H), 1.58 (s, 9H), 1.47 (s, 9H).

Synthesis of [$^{18}$F]TA-1:

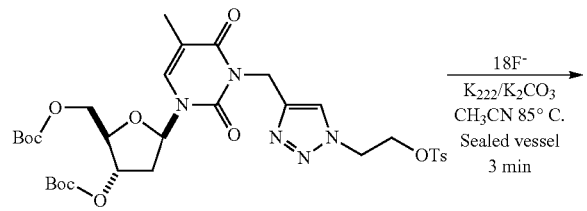

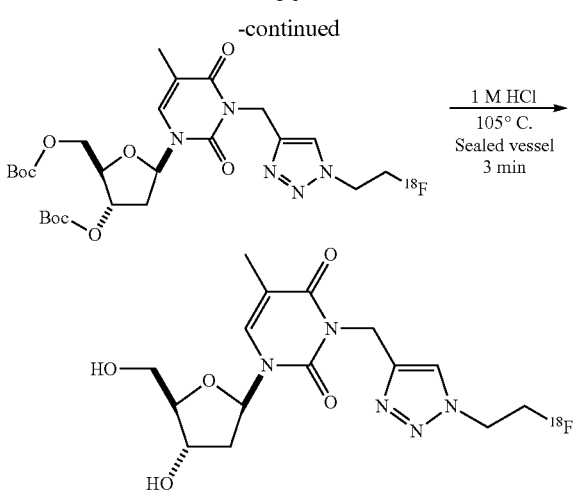

Oxygen-18 water (>97% enriched) was irradiated using 11 MeV protons (RDS-111 Eclipse, Siemens Molecular Imaging) to generate [$^{18}$F]fluoride ion in the usual way. At the end of the bombardment, the [$^{18}$O]water containing [$^{18}$F]fluoride ion was transferred from the tantalum target to an automated nucleophilic fluorination module (explora RN, Siemens Biomarker Solutions). Under computer control, the [$^{18}$O] water/[$^{18}$F]fluoride ion solution was transferred to a small anion exchange resin column (Chromafix 45-PS-HCO3, Machery-Nagel) which had previously been rinsed with water (5 mL), aqueous potassium bicarbonate (0.5 M, 5 mL), and water (5 mL). The [$^{18}$O]water (1.8 mL) was recovered for subsequent purification and reuse. The trapped [18F]fluoride ion was eluted into the reaction vessel with a solution of potassium carbonate (3.0 mg) in water (0.4 mL). A solution of Kryptofix 222 (K222, 20 mg) in acetonitrile (1.0 mL) was added, and the mixture was heated (70 to 95° C.) under vacuum and a stream of argon to evaporate the acetonitrile and water. After cooling, to the residue of "dry" reactive [$^{18}$F]fluoride ion, K222, and potassium carbonate, was added a solution of 2-(4-((3-((2R,4S,5R)-4-(tert-butoxycarbonyloxy)-5-((tert-butoxycarbonyloxy)methyl)tetrahydrofuran-2-yl)-5-methyl-2,6-dioxo-2,3-dihydropyrimidin-1(6H)-yl)methyl)-1H-1,2,3-triazol-1-yl)ethyl 4-methylbenzenesulfonate (25.2 mg, 34.6 µmol) in acetonitrile (0.9 mL). The reaction mixture was heated to 55° C. in a sealed vessel (P$_{max}$=2.3 bar) for 5 minutes with stirring (magnetic). The mixture was cooled to 55° C. and most of the acetonitrile was evaporated under vacuum and a stream of argon as before.

To the crude protected [$^{18}$F]fluorinated intermediate was added aqueous hydrochloric acid (1.0 M, 1.0 mL), and the mixture was heated to 105° C. for 3 minutes. After cooling to 35° C., aqueous sodium acetate (2.0 M, 0.5 mL) was added with stirring. The reaction mixture was transferred to a sample loop (1.5 mL), and injected onto a semi-prep HPLC column (Macherey-Nagel Nucleodur C18 Pyramid 7µ, 250× 10 mm, 10% ethanol, 90% water mobile phase, 6.0 mL/min). The product TA-1 eluted at 19-20.5 minutes as monitored by flow-through radiation detection and UV (254 nm). The HPLC eluate containing the product (10-12 mL) was passed through a 0.22 µm sterile filter into a sterile vial.

A typical production run starting with 1.4 Ci of [$^{18}$F]fluoride ion gave 422 mCi (582 mCi at EOB, 42.3% yield) of isolated product after 50 minutes of synthesis and HPLC purification.

The collected product was analyzed by HPLC (Phenomenex Gemini 5μ C18, 150×4.6 mm, 10% ethanol, 90% water mobile phase, 1.0 mL/min). As monitored by radioactivity and UV (254 nm) detection, this product had a retention time of 9.17 minutes and a radiochemical purity of >99.0%.

Synthesis of [$^{18}$F]TA-3:

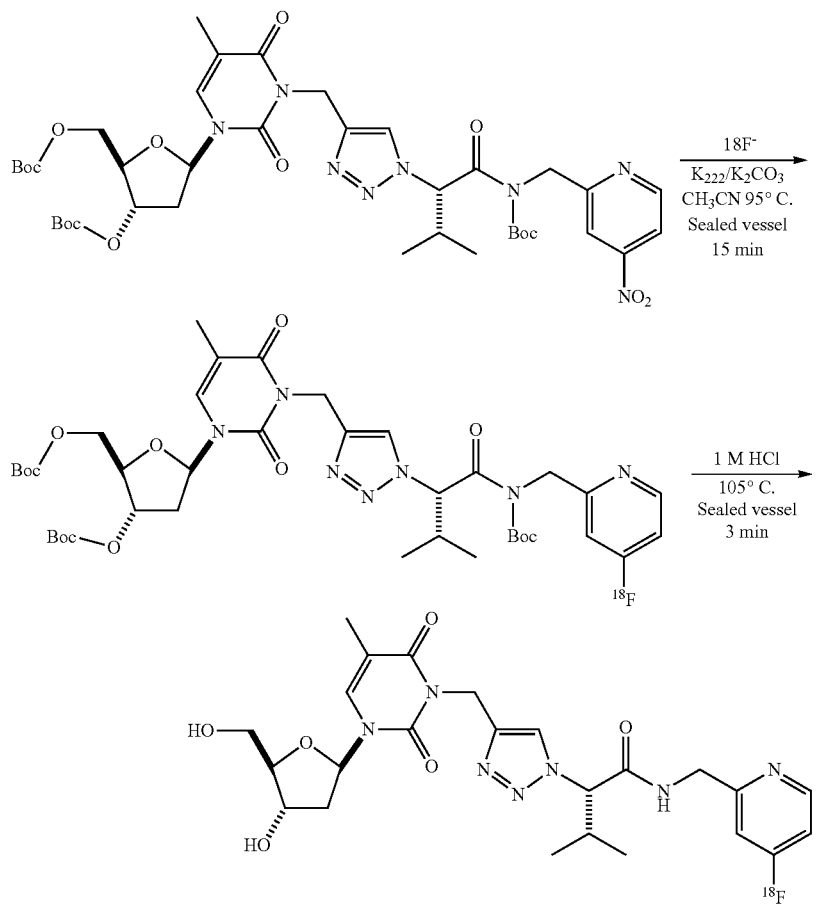

Oxygen-18 water (>97% enriched) was irradiated using 11 MeV protons (RDS-111 Eclipse, Siemens Molecular Imaging) to generate [$^{18}$F]fluoride ion in the usual way. At the end of the bombardment, the [$^{18}$O]water containing [$^{18}$F]fluoride ion was transferred from the tantalum target to an automated nucleophilic fluorination module (explora RN, Siemens Biomarker Solutions). Under computer control, the [$^{18}$O] water/[$^{18}$F]fluoride ion solution was transferred to a small anion exchange resin column (Chromafix 45-PS-HCO3, Machery-Nagel) which had previously been rinsed with water (5 mL), aqueous potassium bicarbonate (0.5 M, 5 mL), and water (5 mL). The [$^{18}$O]water (1.8 mL) was recovered for subsequent purification and reuse. The trapped [$^{18}$F]fluoride ion was eluted into the reaction vessel with a solution of potassium carbonate (3.0 mg) in water (0.4 mL). A solution of Kryptofix 222 (K222, 20 mg) in acetonitrile (1.0 mL) was added, and the mixture was heated (70 to 95° C.) under vacuum and a stream of argon to evaporate the acetonitrile and water. After cooling, to the residue of "dry" reactive [$^{18}$F]fluoride ion, K222, and potassium carbonate, was added a solution of tert-butyl(S)-2-(4-(2-(3-((2R,4S,5R)-4-(tert-butoxycarbonyloxy)-5-(((tert-butoxycarbonyloxy)methyl)tetrahydrofuran-2-yl)-5-methyl-2,6-dioxo-2,3-dihydropyrimidin-1(6H)-yl)ethyl)-1H-1,2,3-triazol-1-yl)-3-methylbutanoyl((4-nitropyridin-2-yl)methyl)carbamate (20.0 mg, 23.3 μmol) in acetonitrile (0.9 mL). The reaction mixture was heated to 95° C. in a sealed vessel ($P_{max}$=2.3 bar) for 15 minutes with stirring (magnetic). The mixture was cooled to 55° C. and most of the acetonitrile was evaporated under vacuum and a stream of argon as before.

To the crude protected [$^{18}$F]fluorinated intermediate was added aqueous hydrochloric acid (1.0 M, 1.0 mL), and the mixture was heated to 105° C. for 3 minutes. After cooling to 35° C., aqueous sodium acetate (2.0 M, 0.5 mL) was added with stirring. The reaction mixture was transferred to a sample loop (1.5 mL), and injected onto a semi-prep HPLC column (Macherey-Nagel Nucleodur C18 Pyramid 7μ, 250×10 mm, 10% ethanol, 90% water mobile phase, 6.0 mL/min). The product TA-3 eluted at 14.5-15.5 minutes as monitored by flow-through radiation detection and UV (254 nm). The HPLC eluate containing the product (10-12 mL) was passed through a 0.22 μm sterile filter into a sterile vial.

A typical production run starting with 1.2 Ci of [$^{18}$F]fluoride ion gave 8.84 mCi (13.2 mCi at EOB, 1.1% yield) of isolated product after 60 minutes of synthesis and HPLC purification.

The collected product was analyzed by HPLC (Phenomenex Gemini 5μ, C18, 150×4.6 mm, 10% ethanol, 90% water mobile phase, 1.0 mL/min). As monitored by radioactivity and UV (254 nm) detection, this product had a retention time of 12.2 minutes and a radiochemical purity of >99.0%.

Synthesis of [$^{18}$F]Ta-4:

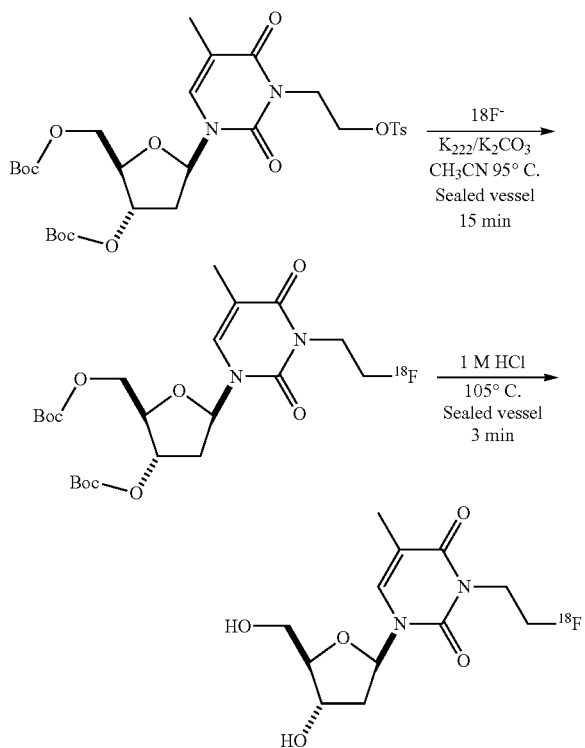

Oxygen-18 water (>97% enriched) was irradiated using 11 MeV protons (RDS-111 Eclipse, Siemens Molecular Imaging) to generate [$^{18}$F]fluoride ion in the usual way. At the end of the bombardment, the [$^{18}$O]water containing [$^{18}$F]fluoride ion was transferred from the tantalum target to an automated nucleophilic fluorination module (explora RN, Siemens Biomarker Solutions). Under computer control, the [$^{18}$O]water/[$^{18}$F]fluoride ion solution was transferred to a small anion exchange resin column (Chromafix 45-PS-HCO3, Machery-Nagel) which had previously been rinsed with water (5 mL), aqueous potassium bicarbonate (0.5 M, 5 mL), and water (5 mL). The [$^{18}$O]water (1.8 mL) was recovered for subsequent purification and reuse. The trapped [$^{18}$F]fluoride ion was eluted into the reaction vessel with a solution of potassium carbonate (3.0 mg) in water (0.4 mL). A solution of Kryptofix 222 (K222, 20 mg) in acetonitrile (1.0 mL) was added, and the mixture was heated (70 to 95° C.) under vacuum and a stream of argon to evaporate the acetonitrile and water. After cooling, to the residue of "dry" reactive [$^{18}$F]fluoride ion, K222, and potassium carbonate, was added a solution of 3-N-(2'-(p-toluenesulfonyloxy)ethyl)-3'-O-Boc-5'-O-Boc-thymidine (19.7 mg, 30.7 µmol) in acetonitrile (0.9 mL). The reaction mixture was heated to 95° C. in a sealed vessel ($P_{max}$=2.3 bar) for 15 minutes with stirring (magnetic). The mixture was cooled to 55° C. and most of the acetonitrile was evaporated under vacuum and a stream of argon as before.

To the crude protected [$^{18}$F]fluorinated intermediate was added aqueous hydrochloric acid (1.0 M, 1.0 mL), and the mixture was heated to 105° C. for 3 minutes. After cooling to 35° C., aqueous sodium acetate (2.0 M, 0.5 mL) was added with stirring. The reaction mixture was transferred to a sample loop (1.5 mL), and injected onto a semi-prep HPLC column (Macherey-Nagel Nucleodur C18 Pyramid 7µ, 250× 10 mm, 8% ethanol, 92% 21 mM phosphate buffer (pH 8.0) mobile phase, 6.0 mL/min). The product 3-N-(2'-[$^{18}$F]fluoroethyl)-thymidine (3, [$^{18}$F]NFET) eluted at 13-14 minutes as monitored by flow-through radiation detection and UV (254 nm). The HPLC eluate containing the product (10-12 mL) was passed through a 0.22 µm sterile filter into a sterile vial.

A typical production run starting with 1.09 Ci of [$^{18}$F] fluoride ion gave 28.8 mCi (40.7 mCi at EOB, 3.74% yield) of isolated product after 55 minutes of synthesis and HPLC purification.

The collected product was analyzed by HPLC (Phenomenex Gemini 5µ, C18, 150×4.6 mm, 10% ethanol, 90% water mobile phase, 1.0 mL/min). As monitored by radioactivity and UV (267 nm) detection, this product had a retention time of 8.4 minutes and a radiochemical purity of >99.0%.

Synthesis of [$^{18}$F]TA-7:

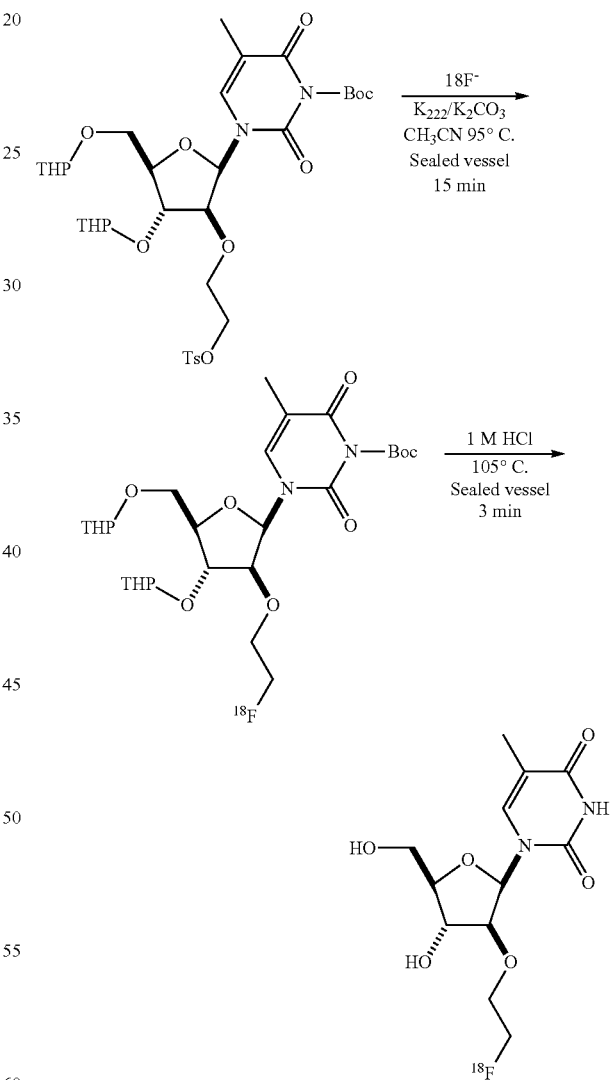

Oxygen-18 water (>97% enriched) was irradiated using 11 MeV protons (RDS-111 Eclipse. Siemens Molecular Imaging) to generate [$^{18}$F]fluoride ion in the usual way. At the end of the bombardment, the [$^{18}$O]water containing [$^{18}$F]fluoride ion was transferred from the tantalum target to an automated nucleophilic fluorination module (explora RN, Siemens Biomarker Solutions). Under computer control, the [$^{18}$O] water/[$^{18}$F]fluoride ion solution was transferred to a small anion exchange resin column (Chromafix 45-PS-HCO3, Machery-Nagel) which had previously been rinsed with water (5 mL), aqueous potassium bicarbonate (0.5 M, 5 mL), and water (5 mL). The [$^{18}$O]water (1.8 mL) was recovered for subsequent purification and reuse. The trapped [$^{18}$F]fluoride ion was eluted into the reaction vessel with a solution of potassium carbonate (3.0 mg) in water (0.4 mL). A solution of Kryptofix 222 (K222, 20 mg) in acetonitrile (1.0 mL) was added, and the mixture was heated (70 to 95° C.) under vacuum and a stream of argon to evaporate the acetonitrile and water. After cooling, to the residue of "dry" reactive [$^{18}$F]fluoride ion, K222, and potassium carbonate, was added a solution of tert-butyl 5-methyl-2,6-dioxo-3-((2R,3S,4R,5R)-4-(tetrahydro-2H-pyran-2-yloxy)-5-((tetrahydro-2H-pyran-2-yloxy)methyl)-3-(2-(tosyloxy)ethoxy)tetrahydrofuran-2-yl)-2,3-dihydropyrimidine-1(6H)-carboxylate (19.3 mg, 26.6 μmol) in acetonitrile (0.9 mL). The reaction mixture was heated to 95° C. in a sealed vessel ($P_{max}$=2.3 bar) for 15 minutes with stirring (magnetic). The mixture was cooled to 55° C. and most of the acetonitrile was evaporated under vacuum and a stream of argon as before.

To the crude protected [$^{18}$F]fluorinated intermediate was added aqueous hydrochloric acid (1.0 M, 1.0 mL), and the mixture was heated to 105° C. for 3 minutes. After cooling to 35° C., aqueous sodium acetate (2.0 M, 0.5 mL) was added with stirring. The reaction mixture was transferred to a sample loop (1.5 mL), and injected onto a semi-prep HPLC column (Macherey-Nagel Nucleodur C18 Pyramid 7μ, 250× 10 mm, 10% ethanol, 90% water mobile phase, 6.0 mL/min). The product TA-7 eluted at 12-14 minutes as monitored by flow-through radiation detection and UV (254 nm). The HPLC eluate containing the product (10-12 mL) was passed through a 0.22 μm sterile filter into a sterile vial.

A typical production run starting with 1.1 Ci of [$^{18}$F]fluoride ion gave 211 mCi (285 mCi at EOB, 25% yield) of isolated product after 50 minutes of synthesis and HPLC purification.

The collected product was analyzed by HPLC (Phenomenex Gemini 5μ C18, 150×4.6 mm, 10% ethanol, 90% water mobile phase, 1.0 mL/min). As monitored by radioactivity and UV (254 nm) detection, this product had a retention time of 7.3 minutes and a radiochemical purity of >99.0%.

Synthesis of [$^{18}$F]TA-8:

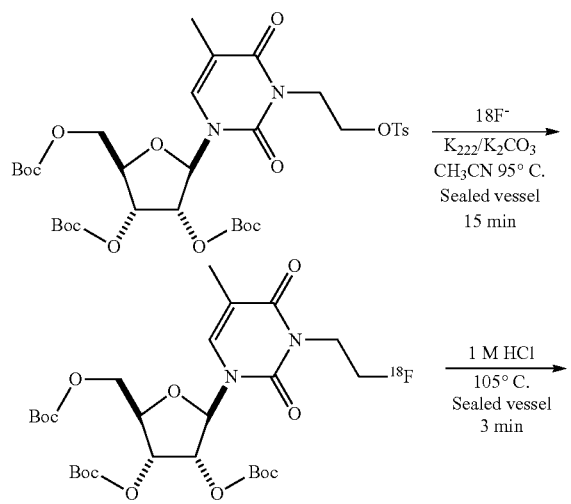

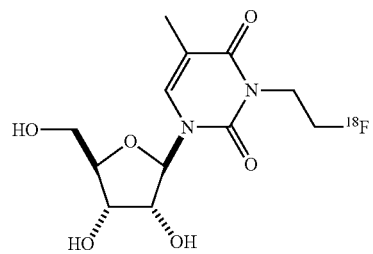

Oxygen-18 water (>97% enriched) was irradiated using 11 MeV protons (RDS-111 Eclipse, Siemens Molecular Imaging) to generate [$^{18}$F]fluoride ion in the usual way. At the end of the bombardment, the [$^{18}$O]water containing [$^{18}$F]fluoride ion was transferred from the tantalum target to an automated nucleophilic fluorination module (explora RN, Siemens Biomarker Solutions). Under computer control, the [$^{18}$O] water/[$^{18}$F]fluoride ion solution was transferred to a small anion exchange resin column (Chromafix 45-PS-HCO3, Machery-Nagel) which had previously been rinsed with water (5 mL), aqueous potassium bicarbonate (0.5 M, 5 mL), and water (5 mL). The [$^{18}$O]water (1.8 mL) was recovered for subsequent purification and reuse. The trapped [$^{18}$F]fluoride ion was eluted into the reaction vessel with a solution of potassium carbonate (3.0 mg) in water (0.4 mL). A solution of Kryptofix 222 (K222, 20 mg) in acetonitrile (1.0 mL) was added, and the mixture was heated (70 to 95° C.) under vacuum and a stream of argon to evaporate the acetonitrile and water. After cooling, to the residue of "dry" reactive [$^{18}$F]fluoride ion, K222, and potassium carbonate, was added a solution of 2-(3-((2R,3R,4R,5R)-3,4-bis(tert-butoxycarbonyloxy)-5-((tert-butoxycarbonyloxy)methyl)tetrahydrofuran-2-yl)-5-methyl-2,6-dioxo-2,3-dihydropyrimidin-1(6H)-yl)ethyl 4-methylbenzenesulfonate (20.2 mg, 26.7 μmol) in acetonitrile (0.9 mL). The reaction mixture was heated to 95° C. in a sealed vessel ($P_{max}$=2.3 bar) for 15 minutes with stirring (magnetic). The mixture was cooled to 55° C. and most of the acetonitrile was evaporated under vacuum and a stream of argon as before.

To the crude protected [$^{18}$F]fluorinated intermediate was added aqueous hydrochloric acid (1.0 M, 1.0 mL), and the mixture was heated to 105° C. for 3 minutes. After cooling to 35° C., aqueous sodium acetate (2.0 M, 0.5 mL) was added with stirring. The reaction mixture was transferred to a sample loop (1.5 mL), and injected onto a semi-prep HPLC column (Macherey-Nagel Nucleodur C18 Pyramid 7μ, 250× 10 mm, 10% ethanol, 90% water mobile phase, 6.0 mL/min). The product TA-8 eluted at 9.5-11 minutes as monitored by flow-through radiation detection and UV (254 nm). The HPLC eluate containing the product (10-12 mL) was passed through a 0.22 μm sterile filter into a sterile vial.

A typical production run starting with 1.1 Ci of [$^{18}$F]fluoride ion gave 80 mCi (95 mCi at EOB, 8.5% yield) of isolated product after 50 minutes of synthesis and HPLC purification.

The collected product was analyzed by HPLC (Phenomenex Gemini 5μ C18, 150×4.6 mm, 10% ethanol, 90% water mobile phase, 1.0 mL/min). As monitored by radioactivity and UV (254 nm) detection, this product had a retention time of 5.8 minutes and a radiochemical purity of >99.0%.

Synthesis of [$^{18}$F]TA-10:

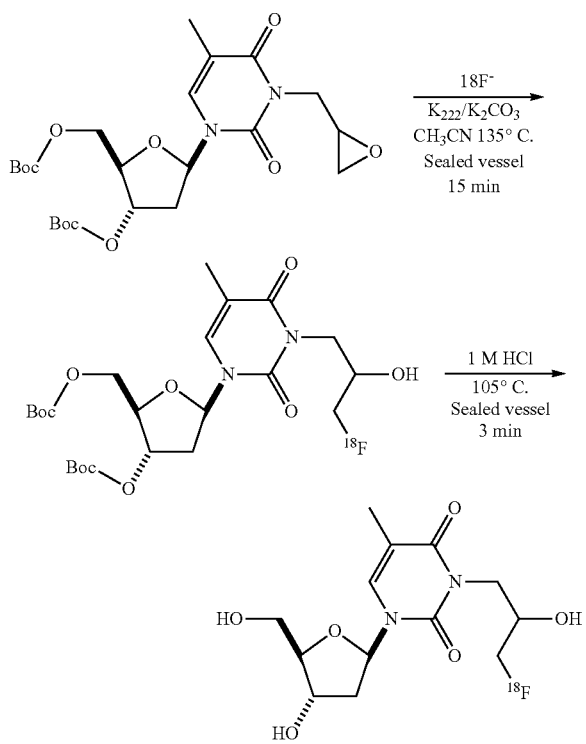

Alternate route:

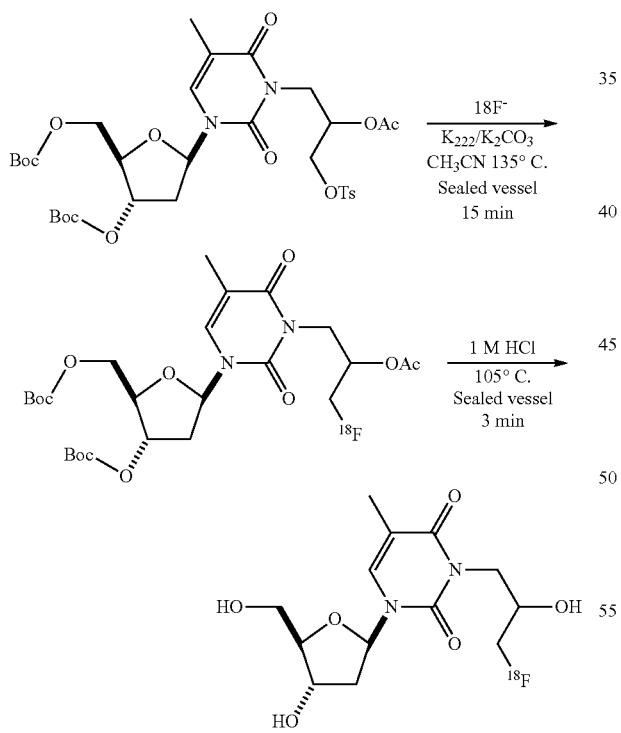

Oxygen-18 water (>97% enriched) was irradiated using 11 MeV protons (RDS-111 Eclipse, Siemens Molecular Imaging) to generate [$^{18}$F]fluoride ion in the usual way. At the end of the bombardment, the [$^{18}$O]water containing [$^{18}$F]fluoride ion was transferred from the tantalum target to an automated nucleophilic fluorination module (explora RN, Siemens Biomarker Solutions). Under computer control, the [$^{18}$O] water/[$^{18}$F]fluoride ion solution was transferred to a small anion exchange resin column (Chromafix 45-PS-HCO3, Machery-Nagel) which had previously been rinsed with water (5 mL), aqueous potassium bicarbonate (0.5 M, 5 mL), and water (5 mL). The [$^{18}$O]water (1.8 mL) was recovered for subsequent purification and reuse. The trapped [$^{18}$F]fluoride ion was eluted into the reaction vessel with a solution of potassium carbonate (3.0 mg) in water (0.4 mL). A solution of Kryptofix 222 (K222, 20 mg) in acetonitrile (1.0 mL) was added, and the mixture was heated (70 to 95° C.) under vacuum and a stream of argon to evaporate the acetonitrile and water. After cooling, to the residue of "dry" reactive [$^{18}$F]fluoride ion, K222, and potassium carbonate, was added a solution of the epoxide starting material (14.6 mg, 31.9 μmol) in acetonitrile (0.9 mL). The reaction mixture was heated to 135° C. in a sealed vessel ($P_{max}$=2.3 bar) for 15 minutes with stirring (magnetic). The mixture was cooled to 55° C. and most of the acetonitrile was evaporated under vacuum and a stream of argon as before.

To the crude protected [$^{18}$F]fluorinated intermediate was added aqueous hydrochloric acid (1.0 M, 1.0 mL), and the mixture was heated to 105° C. for 3 minutes. After cooling to 35° C., aqueous sodium acetate (2.0 M, 0.5 mL) was added with stirring. The reaction mixture was transferred to a sample loop (1.5 mL), and injected onto a semi-prep HPLC column (Macherey-Nagel Nucleodur C18 Pyramid 7μ, 250× 10 mm, 10% ethanol, 90% water mobile phase, 6.0 mL/min). The product TA-10 eluted at 10.5-11.5 minutes as monitored by flow-through radiation detection and UV (254 nm). The HPLC eluate containing the product (10-12 mL) was passed through a 0.22 μm sterile filter into a sterile vial.

A typical production run starting with 0.46 Ci of [$^{18}$F] fluoride ion gave 3.97 mCi (5.3 mCi at EOB, 1.1% yield) of isolated product after 50 minutes of synthesis and HPLC purification.

The collected product was analyzed by HPLC (Phenomenex Gemini 5μ C18, 150×4.6 mm, 10% ethanol, 90% water mobile phase, 1.0 mL/min). As monitored by radioactivity and UV (254 nm) detection, this product had a retention time of 5.8 minutes and a radiochemical purity of >99.0%.

Synthesis of [$^{18}$F]TA-11:

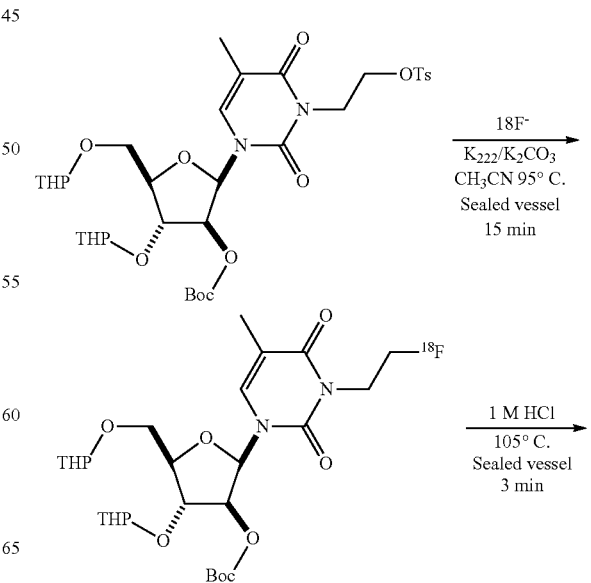

-continued

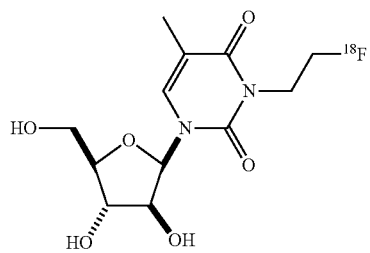

Oxygen-18 water (>97% enriched) was irradiated using 11 MeV protons (RDS-111 Eclipse, Siemens Molecular Imaging) to generate [$^{18}$F]fluoride ion in the usual way. At the end of the bombardment, the [$^{18}$O]water containing [$^{18}$F]fluoride ion was transferred from the tantalum target to an automated nucleophilic fluorination module (explora RN, Siemens Biomarker Solutions). Under computer control, the [$^{18}$O] water/[$^{18}$F]fluoride ion solution was transferred to a small anion exchange resin column (Chromafix 45-PS-HCO3, Machery-Nagel) which had previously been rinsed with water (5 mL), aqueous potassium bicarbonate (0.5 M, 5 mL), and water (5 mL). The [$^{18}$O]water (1.8 mL) was recovered for subsequent purification and reuse. The trapped [$^{18}$F]fluoride ion was eluted into the reaction vessel with a solution of potassium carbonate (3.0 mg) in water (0.4 mL). A solution of Kryptofix 222 (K222, 20 mg) in acetonitrile (1.0 mL) was added, and the mixture was heated (70 to 95° C.) under vacuum and a stream of argon to evaporate the acetonitrile and water. After cooling, to the residue of "dry" reactive [$^{18}$F]fluoride ion, K222, and potassium carbonate, was added a solution of 22-(3-((2R,3S,4R,5R)-3-(ter-butoxycarbonyloxy)-4-(tetrahydro-2H-pyran-2-yloxy)-5-((tetrahydro-2H-pyran-2-yloxy)methyl)tetrahydrofuran-2-yl)-5-methyl-2,6-dioxo-2,3-dihydropyrimidin-1(6H)-yl)ethyl 4-methylbenzenesulfonate (19.2 mg, 26.5 μmol) in acetonitrile (0.9 mL). The reaction mixture was heated to 95° C. in a sealed vessel ($P_{max}$=2.3 bar) for 15 minutes with stirring (magnetic). The mixture was cooled to 55° C. and most of the acetonitrile was evaporated under vacuum and a stream of argon as before.

To the crude protected [$^{18}$F]fluorinated intermediate was added aqueous hydrochloric acid (1.0 M, 1.0 mL), and the mixture was heated to 105° C. for 3 minutes. After cooling to 35° C., aqueous sodium acetate (2.0 M, 0.5 mL) was added with stirring. The reaction mixture was transferred to a sample loop (1.5 mL), and injected onto a semi-prep HPLC column (Macherey-Nagel Nucleodur C18 Pyramid 7μ, 250× 10 mm. 10% ethanol, 90% water mobile phase, 6.0 mL/min). The product TA-11 eluted at 12.5-13.5 minutes as monitored by flow-through radiation detection and UV (254 nm). The HPLC eluate containing the product (10-12 mL) was passed through a 0.22 μm sterile filter into a sterile vial.

A typical production run starting with 0.93 Ci of [$^{18}$F] fluoride ion gave 103 mCi (137 mCi at EOB. 14.8% yield) of isolated product after 5μ minutes of synthesis and HPLC purification.

The collected product was analyzed by HPLC (Phenomenex Gemini 5μ C18, 150×4.6 mm, 10% ethanol, 90% water mobile phase 1.0 mL/min). As monitored by radioactivity and UV (254 nm) detection, this product had a retention time of 7.4 minutes and a radiochemical purity of >99.0%.

Synthesis of [$^{18}$F]TA-12:

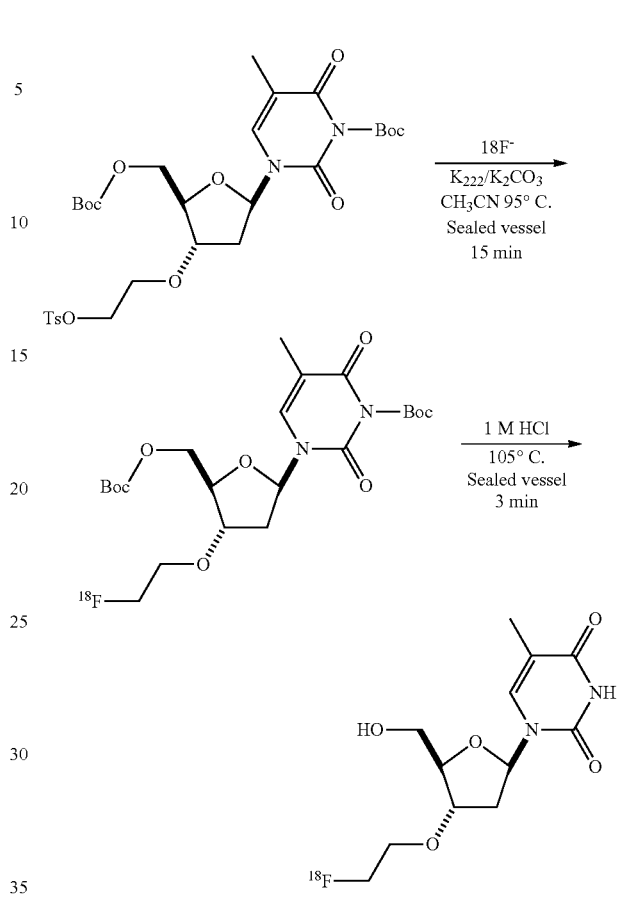

Oxygen-18 water (>97% enriched) was irradiated using 11 MeV protons (RDS-111 Eclipse, Siemens Molecular Imaging) to generate [$^{18}$F]fluoride ion in the usual way. At the end of the bombardment, the [$^{18}$O]water containing [$^{18}$F]fluoride ion was transferred from the tantalum target to an automated nucleophilic fluorination module (explora RN, Siemens Biomarker Solutions). Under computer control, the [$^{18}$O] water/[$^{18}$F]fluoride ion solution was transferred to a small anion exchange resin column (Chromafix 45-PS-HCO3, Machery-Nagel) which had previously been rinsed with water (5 mL), aqueous potassium bicarbonate (0.5 M, 5 mL), and water (5 mL). The [$^{18}$O]water (1.8 mL) was recovered for subsequent purification and reuse. The trapped [$^{18}$F]fluoride ion was eluted into the reaction vessel with a solution of potassium carbonate (3.0 mg) in water (0.4 mL). A solution of Kryptofix 222 (K222, 20 mg) in acetonitrile (1.0 mL) was added, and the mixture was heated (70 to 95° C.) under vacuum and a stream of argon to evaporate the acetonitrile and water. After cooling to the residue of "dry" reactive [$^{18}$F]fluoride ion, K222, and potassium carbonate, was added a solution of tert-butyl 3-((2R,4S,5R)-5-((tert-butoxycarbonyloxy)methyl)-4-(2-(tosyloxy)ethoxy)tetrahydrofuran-2-yl)-5-methyl-2,6-dioxo-2,3-dihydropyrimidine-1(6H)-carboxylate (26.2 mg, 40.9 μmol) in acetonitrile (0.9 mL). The reaction mixture was heated to 95° C. in a sealed vessel ($P_{max}$=2.3 bar) for 15 minutes with stirring (magnetic). The mixture was cooled to 55° C. and most of the acetonitrile was evaporated under vacuum and a stream of argon as before.

To the crude protected [$^{18}$F]fluorinated intermediate was added aqueous hydrochloric acid (1.0 M, 1.0 mL), and the mixture was heated to 105° C. for 3 minutes. After cooling to 35° C., aqueous sodium acetate (2.0 M, 0.5 mL) was added with stirring. The reaction mixture was transferred to a sample loop (1.5 mL), and injected onto a semi-prep HPLC column (Macherey-Nagel Nucleodur C18 Pyramid 7μ, 250× 10 mm, 10% ethanol, 90% water mobile phase, 6.0 mL/min). The product TA-12 eluted at 8.5-10 minutes as monitored by flow-through radiation detection and UV (254 nm). The HPLC eluate containing the product (10-12 mL) was passed through a 0.22 μm sterile filter into a sterile vial.

A typical production run starting with 1.35 Ci of [$^{18}$F] fluoride ion gave 580 mCi (770 mCi at EOB, 57% yield) of isolated product after 45 minutes of synthesis and HPLC purification.

The collected product was analyzed by HPLC (Phenomenex Gemini 5μ C18, 150×4.6 mm, 10% ethanol, 90% water mobile phase, 1.0 mL/min). As monitored by radioactivity and UV (254 nm i) detection, this product had a retention time of 8.4 minutes and a radiochemical purity of >99.0%.

Synthesis of [$^{18}$F]TA-14:

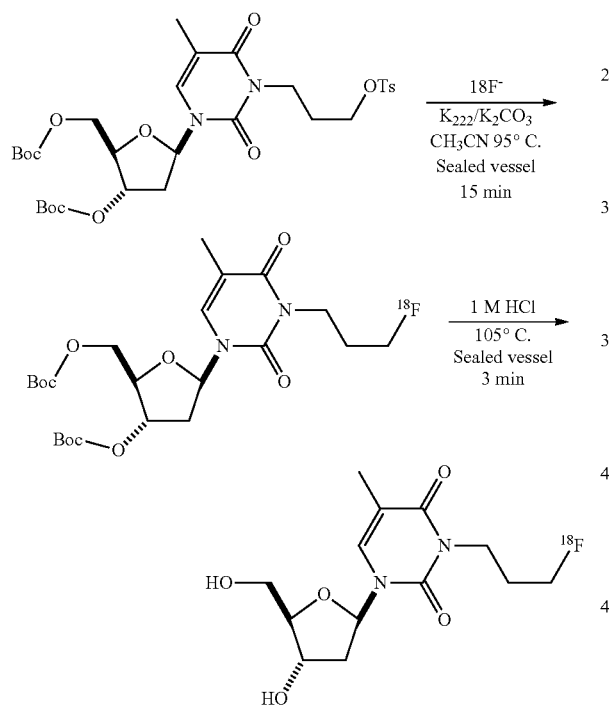

Oxygen-18 water (>97% enriched) was irradiated using 11 MeV protons (RDS-111 Eclipse, Siemens Molecular Imaging) to generate [$^{18}$F]fluoride ion in the usual way. At the end of the bombardment, the [$^{18}$O]water containing [$^{18}$F]fluoride ion was transferred from the tantalum target to an automated nucleophilic fluorination module (explora RN, Siemens Biomarker Solutions). Under computer control, the [$^{18}$O] water/[$^{18}$F]fluoride ion solution was transferred to a small anion exchange resin column (Chromafix 45-PS-HCO3. Machery-Nagel) which had previously been rinsed with water (5 mL), aqueous potassium bicarbonate (0.5 M, 5 mL), and water (5 mL). The [$^{18}$O]water (1.8 mL) was recovered for subsequent purification and reuse. The trapped [$^{18}$F]fluoride ion was eluted into the reaction vessel with a solution of potassium carbonate (3.0 mg) in water (0.4 mL). A solution of Kryptofix 222 (K222, 20 mg) in acetonitrile (1.0 mL) was added, and the mixture was heated (70 to 95° C.) under vacuum and a stream of argon to evaporate the acetonitrile and water. After cooling, to the residue of "dry" reactive [$^{18}$F]fluoride ion, K222, and potassium carbonate, was added a solution 3-(3-(((2R,4S,5R)-4-(tert-butoxycarbonyloxy)-5-((tert-butoxycarbonyloxy)methyl)tetrahydrofuran-2-yl)-5-methyl-2,6-dioxo-2,3-dihydropyrimidin-1(6H)-yl)propyl 4-methylbenzenesulfonate (23.3 mg, 35.6 μmol) in acetonitrile (0.9 mL). The reaction mixture was heated to 95° C. in a sealed vessel ($P_{max}$=2.3 bar) for 15 minutes with stirring (magnetic). The mixture was cooled to 55° C. and most of the acetonitrile was evaporated under vacuum and a stream of argon as before.

To the crude protected [$^{18}$F]fluorinated intermediate was added aqueous hydrochloric acid (1.0 M, 1.0 mL), and the mixture was heated to 105° C. for 3 minutes. After cooling to 35° C., aqueous sodium acetate (2.0 M, 0.5 mL) was added with stirring. The reaction mixture was transferred to a sample loop (1.5 mL), and injected onto a semi-prep HPLC column (Macherey-Nagel Nucleodur C18 Pyramid 7μ, 250× 10 mm, 10% ethanol, 90% water mobile phase, 6.0 mL/min). The product TA-14 eluted at 15-16 minutes as monitored by flow-through radiation detection and UV (254 nm). The HPLC eluate containing the product (10-12 mL) was passed through a 0.22 μm sterile filter into a sterile vial.

A typical production run starting with 0.72 Ci of [$^{18}$F] fluoride ion gave 191 mCi (293 mCi at EOB. 38% yield) of isolated product after 70 minutes of synthesis and HPLC purification.

The collected product was analyzed by HPLC (Phenomenex Gemini 5μ C18, 150×4.6 mm, 10% ethanol, 90% water mobile phase, 1.0 mL/min). As monitored by radioactivity and UV (254 nm) detection, this product had a retention time of 16.9 minutes and a radiochemical purity of >99.0%.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope. The entire disclosures of all documents cited throughout this application are incorporated herein by reference.

What is claimed is:

1. A compound of the Formula 1:

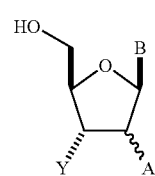

wherein:

B = 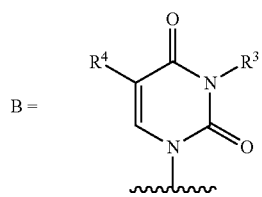

A is hydroxy, or —O—X-halo-, provided that when A is —O—X-halo-, then Y is —O—$R^1$, and provided that when Y is hydroxy then $R^3$ is not —$CH_2CH_2$—$^{18}F$, wherein halo is optionally replaced by Z;

wherein each X is a bond, or is independently a linker selected from the group consisting of:
a) $C_{1-10}$alkylenyl wherein at least one of the $C_1$alkylenyl in the $C_{1-10}$alkylenyl group is optionally replaced by —O—, —S—, —N($R^{10}$)—, —C(O)—, —C(S)—, —C(O)O—, —C(S)O—, —N($R^{10}$)C(O)—, —N($R^{10}$)C(S)—, —S(O)N($R^{10}$)— and —N($R^{10}$)S(O)$_2$; $C_{6-14}$arylenyl, $C_{1-3}$alkylenyl-arylenyl, $C_{1-3}$alkylenyl-aryl-$C_{1-3}$alkylenyl-aryl, $C_{3-6}$cycloalkylenyl, $C_{3-12}$cycloalkyl$C_{1-5}$alkylenyl, $C_{6-10}$aryl$C_{1-4}$alkylenyl, heteroarylenyl, —($CH_2CH_2O$)$_{1-6}C_{1-3}$alkylenyl, $C_{1-3}$alkylenyl($OCH_2CH_2$)$_{1-6}O$—, $C_{1-5}$alkylenyloxy, —$CH_2CH_2O$—, —$CH_2CH_2$—($OCH_2CH_2$)$_{1-6}O$—, $C_{1-3}$alkylenyl-arylenyl-$C_{1-3}$alkylenyl, $C_{3-6}$cycloalkylenyloxy, $C_{3-12}$cycloalkylenyl$C_{1-5}$alkylenyloxy, $C_{1-3}$alkylenyl-heteroaryl-$C_{1-3}$alkylenyl-heteroaryl, heteroarylenyl$C_{2-5}$alkylenyloxy, $C_{6-14}$arylenyloxy, $C_{6-10}$arylenyl$C_{1-4}$alkylenyloxy and heteroarylenyloxy;
wherein each $C_{6-14}$arylenyl, $C_{1-3}$alkylenyl-arylenyl, $C_{1-3}$alkylenyl-aryl-$C_{1-3}$alkylenyl-aryl, $C_{3-6}$cycloalkylenyl, $C_{3-12}$cycloalkyl$C_{1-5}$alkylenyl, $C_{6-10}$aryl$C_{1-4}$alkylenyl, heteroarylenyl, —($CH_2CH_2O$)$_{1-6}C_{1-3}$alkylenyl, $C_{1-3}$alkylenyl($OCH_2CH_2$)$_{1-6}O$—, $C_{1-5}$alkylenyloxy, $C_{1-3}$alkylenyl-arylenyl-$C_{1-3}$alkylenyl, $C_{3-6}$cycloalkylenyloxy, $C_{3-12}$cycloalkylenyl$C_{1-5}$alkylenyloxy, $C_{1-3}$alkylenyl-heteroaryl-$C_{1-3}$alkylenyl-heteroaryl, heteroarylenyl$C_{2-5}$alkylenyloxy, $C_{6-14}$arylenyloxy, $C_{6-10}$arylenyl$C_{1-4}$alkylenyloxy and heteroarylenyloxy is optionally substituted with one or two amino, halo, cyano, hydroxy, oxo, thio and azido group;
b) —NH—(R)CHCOO— where R is an amino acid side chain; a peptide, a monosaccharide, disaccharide or oligosaccharide; or
c) a combination of at least one of the groups in a) and one of the groups in b);

Y is selected from the group consisting of hydroxy, halo, halo-$C_{1-4}$alkyl-aryl, halo-$C_{1-4}$alkyl-heteroaryl, halo-$C_{1-4}$alkoxy, perhalo$C_{1-4}$-alkoxy, $C_{3-6}$cycloalkoxy, $C_{3-12}$cycloalkyl$C_{1-5}$alkoxy, aryl, $C_{6-14}$aryloxy, $C_{6-10}$aryl$C_{1-4}$alkoxy, heteroaryl, heteroaryl$C_{1-4}$alkyl and heteroaryloxy, wherein halo is optionally replaced by Z; or Y is —X—Z;

each Z is independently a radionuclide selected from the group consisting of $^{11}C$, $^{18}F$, $^{123}I$, $^{124}I$, $^{125}I$, $^{131}I$ and $^{77}Br$;

$R^1$ is H or is selected from the group consisting of halo-$C_{1-4}$alkyl, perhalo$C_{1-4}$alkyl, $C_{1-5}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl and heteroaryl, wherein halo is optionally replaced by Z;

$R^3$ is H or is selected from the group consisting of halo-$C_{1-4}$alkyl, perhalo$C_{1-4}$alkyl, $C_{1-5}$alkyl $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, heteroaryl$C_{1-3}$alkyl-heteroaryl$C_{1-3}$alkyl-, ($C_{1-6}$alkyl)$_2$NC(O)CH($C_{1-5}$alkyl)-, halo-$C_{1-6}$alkylN$R^{11}$C(O)CH($C_{1-5}$alkyl)-, halo-$C_{1-6}$alkylOC(O)CH($C_{1-5}$alkyl)-, wherein halo is optionally replaced by Z; or $R^3$ is —X—Z;

$R^4$ is H or is selected from the group consisting of $CH_3$—, $C_{2-5}$alkyl, aryl, heteroaryl, halo-$C_{1-4}$alkyl, halo-$C_{1-4}$alkyl-heteroaryl-, halo-$C_{1-4}$alkyl-heteroaryl$C_{1-4}$alkyl, halo-$C_{1-4}$alkyl-aryl- and halo-$C_{1-4}$alkyl-aryl$C_{1-4}$alkyl, wherein halo is optionally replaced by Z;

each $R^{10}$ is independently H or $C_{1-6}$alkyl; and
each $R^{11}$ is independently H or $C_{1-6}$alkyl;
or a pharmaceutically acceptable salt thereof.

2. The compound of claim 1, wherein:
Y is hydroxy;
$R^3$ is —X—Z; and
$R^4$ is $CH_3$.

3. The compound of claim 1 that is:

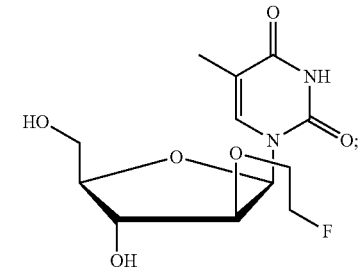

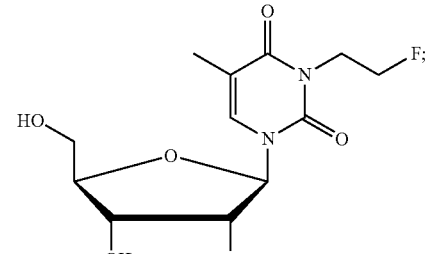

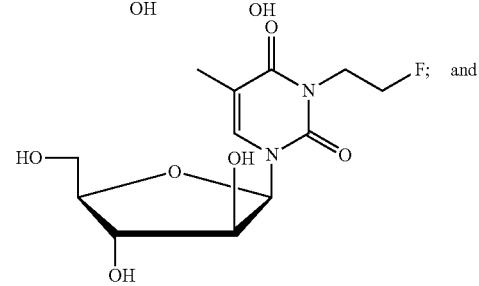 and

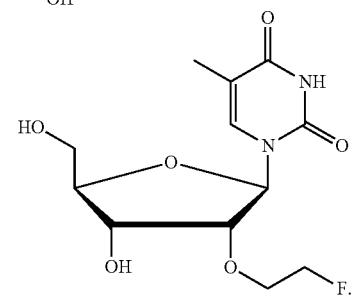

4. The compound of claim 2, wherein A is OH.

5. The compound of claim 1, wherein:
A is —O—X-halo, wherein X is —$CH_2CH_2$—;
Y is hydroxy;
$R^3$ is H; and
$R^4$ is $CH_3$—.

6. The compound of claim 1, wherein $R^3$ is selected from the group consisting of halo-$C_{1-4}$alkyl, perhalo$C_{1-4}$alkyl, halo-$C_{1-4}$alkyl-aryl, halo-$C_{1-4}$alkyl-heteroaryl-$C_{1-4}$alkyl, halo-$C_{1-6}$alkylOC(O)CH($C_{1-5}$alkyl)-, $C_{1-5}$alkyl, $C_{3-6}$cycloalkyl, $C_{3-12}$cycloalkyl$C_{1-5}$alkyl, $C_{6-14}$aryl, $C_{6-10}$aryl$C_{1-4}$ alkyl, heteroaryl, heteroarylC$_{1-3}$alkyl-heteroarylC$_{1-3}$alkyl-, (C$_{1-6}$alkyl)$_2$NC(O)CH(C$_{1-5}$alkyl)-.

7. The compound of claim 6, wherein R$^3$ is halo-C$_{1-4}$alkyl.

8. The compound of claim 1, wherein at least one of the alkylenyl groups of X is branched.

9. A compound of the Formula 1:

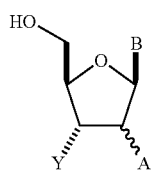

wherein B is

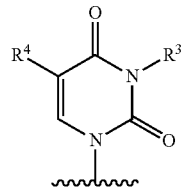

wherein:

A is H, hydroxy, or —O—X-halo-, provided that when A is —O—X-halo-, then Y is —O—R$^1$, wherein halo is optionally replaced by Z;

wherein each X is a bond, or is independently a linker selected from the group consisting of:
  a) C$_{1-10}$alkylenyl wherein at least one of the C$_1$alkylenyl in the C$_{1-10}$alkylenyl group is optionally replaced by —O—, —S—, —N(R$^{10}$)—, —C(O)—, —C(S)—, —C(O)O—, —C(S)O—, —N(R$^{10}$)C(O)—, —N(R$^{10}$)C(S)—, —S(O)N(R$^{10}$)— and —N(R$^{10}$)S(O)$_2$;

C$_{6-14}$arylenyl, C$_{1-3}$alkylenyl-arylenyl, C$_{1-3}$alkylenyl-aryl-C$_{1-3}$alkylenyl-aryl, C$_{3-6}$cycloalkylenyl, C$_{3-12}$cycloalkylC$_{1-5}$alkylenyl, C$_{6-10}$arylC$_{1-4}$alkylenyl, heteroarylenyl, —(CH$_2$CH$_2$O)$_{1-6}$C$_{1-3}$alkylenyl, C$_{1-3}$alkylenyl(OCH$_2$CH$_2$)$_{1-6}$O—, C$_{1-5}$alkylenyloxy, —CH$_2$CH$_2$O—, —CH$_2$CH$_2$—(OCH$_2$CH$_2$)$_{1-6}$O—, C$_{1-3}$alkylenyl-arylenyl-C$_{1-3}$alkylenyl, C$_{3-6}$cycloalkylenyloxy, C$_{3-12}$cycloalkylenylC$_{1-5}$ alkylenyloxy, C$_{1-3}$alkylenyl-heteroaryl-C$_{1-3}$alkylenyl-heteroaryl, heteroarylenylC$_{2-5}$alkylenyloxy, C$_{6-14}$arylenyloxy, C$_{6-10}$arylenylC$_{1-4}$alkylenyloxy and heteroarylenyloxy;

wherein each C$_{6-14}$arylenyl, C$_{1-3}$alkylenyl-arylenyl, C$_{1-3}$alkylenyl-aryl-C$_{1-3}$alkylenyl-aryl, C$_{3-6}$cycloalkylenyl, C$_{3-12}$cycloalkylC$_{1-5}$alkylenyl, C$_{6-10}$arylC$_{1-4}$alkylenyl, heteroarylenyl, —(CH$_2$CH$_2$O)$_{1-6}$C$_{1-3}$alkylenyl, C$_{1-3}$alkylenyl(OCH$_2$CH$_2$)$_{1-6}$O—, C$_{1-5}$alkylenyloxy, C$_{1-3}$alkylenyl-arylenyl-C$_{1-3}$alkylenyl, C$_{3-6}$cycloalkylenyloxy, C$_{3-12}$cycloalkylenylC$_{1-5}$alkylenyloxy, C$_{1-3}$alkylenyl-heteroaryl-C$_{1-3}$alkylenyl-heteroaryl, heteroarylenylC$_{2-5}$alkylenyloxy, C$_{6-14}$arylenyloxy, C$_{6-10}$arylenylC$_{1-4}$alkylenyloxy and heteroarylenyloxy is optionally substituted with one or two amino, halo, cyano, hydroxy, oxo, thio and azido group;

b) —NH—(R)CHCOO— where R is an amino acid side chain; a peptide, a monosaccharide, disaccharide or oligosaccharide; or
  c) a combination of at least one of the groups in a) and one of the groups in b);

Y is selected from the group consisting of Z, halo, halo-C$_{1-4}$alkyl-aryl, halo-C$_{1-4}$alkyl-heteroaryl, halo-C$_{1-4}$alkoxy, perhaloC$_{1-4}$-alkoxy, and C$_{1-10}$alkylenyl;
  wherein halo of halo-C$_{1-4}$alkyl-aryl, halo-C$_{1-4}$alkyl-heteroaryl, halo-C$_{1-4}$alkoxy, perhaloC$_{1-4}$alkoxy is optionally replaced by Z,
  wherein at least one of the carbon atoms of the C$_{1-10}$alkylenyl is optionally replaced by a halo or Z, —O— and/or amino, cyano, oxo, thio and azido,
  wherein at least one of the carbon atoms of the halo-C$_{1-4}$alkyl-aryl, halo-C$_{1-4}$alkyl-heteroaryl, halo-C$_{1-4}$alkoxy, perhaloC$_{1-4}$alkoxy is optionally substituted with hydroxy;

wherein each Z is independently a radionuclide selected from the group consisting of $^{11}$C, $^{18}$F, $^{123}$I, $^{124}$I, $^{125}$I, $^{131}$I and $^{77}$Br;

R$^3$ is H or is selected from the group consisting of halo-C$_{1-4}$alkyl, perhaloC$_{1-4}$alkyl, C$_{1-5}$alkyl, C$_{3-6}$cycloalkyl, C$_{3-12}$cycloalkylC$_{1-5}$alkyl, C$_{6-14}$aryl, C$_{6-10}$arylC$_{1-4}$alkyl, heteroaryl, heteroarylC$_{1-3}$alkyl-heteroarylC$_{1-3}$alkyl-, (C$_{1-6}$alkyl)$_2$NC(O)CH(C$_{1-5}$alkyl)-, halo-C$_{1-6}$alkylNR$^{11}$C(O)CH (C$_{1-5}$alkyl)-, halo-C$_{1-6}$ $_{alkyl}$OC(O)CH(C$_{1-5}$alkyl)-, wherein halo is optionally replaced by Z; and R$^4$ is H or is selected from the group consisting of CH$_3$—, C$_{2-5}$alkyl, aryl, heteroaryl, halo-C$_{1-4}$alkyl, halo-C$_{1-4}$alkyl-heteroaryl-, halo-C$_{1-4}$alkyl-heteroarylC$_{1-4}$alkyl, halo-C$_{1-4}$alkyl-aryl- and halo-C$_{1-4}$alkyl-arylC$_{1-4}$alkyl, wherein halo is optionally replaced by Z;

each R$^{10}$ is independently H or C$_{1-6}$alkyl; and
each R$^{11}$ is independently H or C$_{1-6}$alkyl,
or a pharmaceutically acceptable salt thereof.

10. The compound of claim 8, wherein A is H.

11. The compound of claim 8, wherein Y is Z or halo.

12. The compound of claim 10, wherein Y is selected from the group consisting of F and $^{18}$F.

13. The compound of claim 8, wherein R$^4$ is CH$_3$.

14. The compound of claim 8, wherein R$^4$ is C$_{2-5}$alkyl, aryl, heteroaryl, halo-C$_{1-4}$alkyl, halo-C$_{1-4}$alkyl-heteroaryl-, halo-C$_{1-4}$alkyl-heteroarylC$_{1-4}$alkyl, halo-C$_{1-4}$alkyl-aryl-and halo-C$_{1-4}$alkyl-arylC$_{1-4}$alkyl.

15. The compound of claim 8, wherein Y is selected from the group consisting of halo-C$_{1-4}$alkyl-aryl, halo-C$_{1-4}$alkyl-heteroaryl, halo-C$_{1-4}$alkoxy, perhaloC$_{1-4}$-alkoxy, wherein at least one of the carbon atoms of halo-C$_{1-4}$alkyl-aryl, halo-C$_{1-4}$alkyl-heteroaryl, halo-C$_{1-4}$alkoxy, perhaloC$_{1-4}$-alkoxy is optionally substituted with hydroxyl.

16. The compound of claim 14, wherein Y is halo-C$_{1-4}$alkyl-heteroaryl.

17. The compound of claim 15, wherein the heteroaryl is a triazole.

18. The compound of claim 14, wherein R$^3$ is H.

19. The compound of claim 10, wherein R$^3$ is halo-C$_{1-4}$alkyl.

20. The compound of claim 10, wherein R$^3$ is halo-C$_{1-4}$alkyl-heteroaryl-C$_{1-4}$alkyl.

21. The compound of claim 8, selected from the group consisting of:

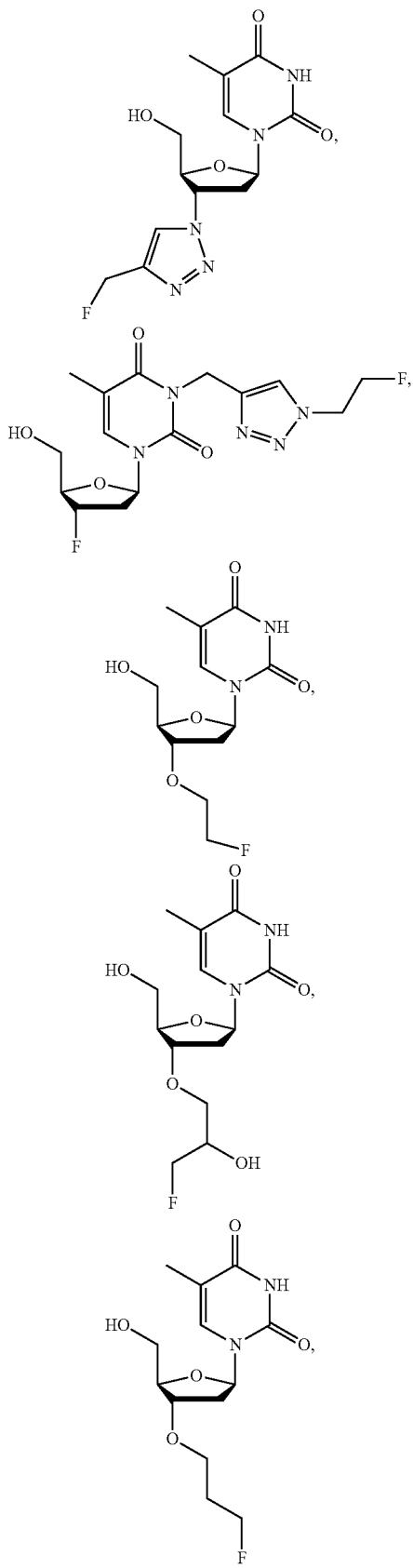

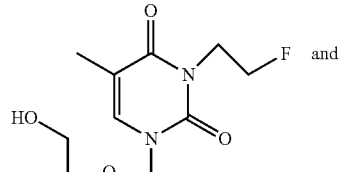

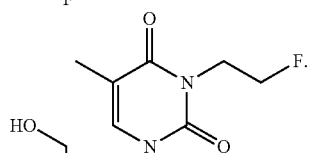

22. A compound of the Formula 1:

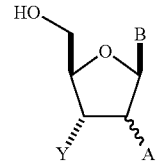

wherein B is

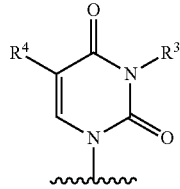

wherein:
A is H, hydroxy, or —O—X-halo-, provided that when A is —O—X-halo-, then Y is —O—R$^1$, wherein halo is optionally replaced by Z;
wherein each X is a bond, or is independently a linker selected from the group consisting of:
  a) $C_{1-10}$alkylenyl wherein at least one of the $C_1$alkylenyl in the $C_{1-10}$alkylenyl group is optionally replaced by —O—, —S—, —N(R$^{10}$)—, —C(O)—, —C(S)—, —C(O)O—, —C(S)O—, —N(R$^{10}$)C(O)—, —N(R$^{10}$)C(S)—, —S(O)N(R$^{10}$)— and —N(R$^{10}$)S(O)$_2$;
  $C_{6-14}$arylenyl, $C_{1-3}$alkylenyl-arylenyl, $C_{1-3}$alkylenyl-aryl-$C_{1-3}$alkylenyl-aryl, $C_{3-6}$cycloalkylenyl, $C_{3-12}$cycloalkylC$_{1-5}$alkylenyl, $C_{6-10}$arylC$_{1-4}$alkylenyl, heteroarylenyl, —(CH$_2$CH$_2$O)$_{1-6}$C$_{1-3}$alkylenyl, $C_{1-3}$alkylenyl(OCH$_2$CH$_2$)$_{1-6}$O—, $C_{1-5}$ alkylenyloxy, —CH$_2$CH$_2$O—, —CH$_2$CH$_2$—(OCH$_2$CH$_2$)$_{1-6}$O—, $C_{1-3}$alkylenyl-arylenyl-C$_{1-3}$alkylenyl, $C_{3-6}$cycloalkylenyloxy, $C_{3-12}$cycloalkylenylC$_{1-5}$alkylenyloxy, $C_{1-3}$alkylenyl-heteroaryl-C$_{1-3}$alkylenyl-heteroaryl, heteroarylenylC$_{2-5}$alkylenyloxy, $C_{6-14}$arylenyloxy, $C_{6-10}$arylenylC$_{1-4}$alkylenyloxy and heteroarylenyloxy;

wherein each $C_{6-14}$arylenyl, $C_{1-3}$alkylenyl-arylenyl, $C_{1-3}$alkylenyl-aryl-$C_{1-3}$alkylenyl-aryl, $C_{3-6}$cycloalkylenyl, $C_{3-12}$cycloalkyl$C_{1-5}$alkylenyl, $C_{6-10}$aryl$C_{1-4}$alkylenyl, heteroarylenyl, —(CH$_2$CH$_2$O)$_{1-6}$$C_{1-3}$alkylenyl, $C_{1-3}$alkylenyl(OCH$_2$CH$_2$)$_{1-6}$O—, $C_{1-5}$alkylenyloxy, $C_{1-3}$alkylenyl-arylenyl-$C_{1-3}$alkylenyl, $C_{3-6}$cycloalkylenyloxy, $C_{3-12}$cycloalkylenyl$C_{1-5}$alkylenyloxy, $C_{1-3}$alkylenyl-heteroaryl-$C_{1-3}$alkylenyl-heteroaryl, heteroarylenyl$C_{2-5}$alkylenyloxy, $C_{6-14}$arylenyloxy, $C_{6-10}$arylenyl$C_{1-4}$alkylenyloxy and heteroarylenyloxy is optionally substituted with one or two amino, halo, cyano, hydroxy, oxo, thio and azido group;

b) —NH—(R)CHCOO— where R is an amino acid side chain; a peptide, a monosaccharide, disaccharide or oligosaccharide; or c) a combination of at least one of the groups in a) and one of the groups in b);

Y is selected from the group consisting of hydroxy, halo, halo-$C_{1-4}$alkyl-aryl, halo-$C_{1-4}$alkyl-heteroaryl, halo-$C_{1-4}$alkoxy, perhalo$C_{1-4}$alkoxy, $C_{3-6}$cycloalkoxy, $C_{3-12}$cycloalkyl$C_{1-5}$alkoxy, aryl, $C_{6-14}$aryloxy, $C_{6-10}$aryl$C_{1-4}$alkoxy, heteroaryl, heteroaryl$C_{1-4}$alkyl and heteroaryloxy; wherein halo is optionally replaced by Z;

$R^3$ is H or is selected from the group consisting of halo-$C_{1-4}$alkyl, perhalo$C_{1-4}$alkyl, halo-$C_{1-4}$alkyl-aryl, halo-$C_{1-4}$alkyl-heteroaryl-$C_{1-4}$alkyl, halo-$C_{1-6}$alkylNR$^{11}$C(O)CH($C_{1-5}$alkyl)-, halo-$C_{1-6}$alkylOC(O)CH($C_{1-5}$alkyl)-, $C_{1-5}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, heteroaryl$C_{1-3}$alkyl-heteroaryl$C_{1-3}$alkyl-, ($C_{1-6}$alkyl)$_2$NC(O)CH($C_{1-5}$alkyl)-, wherein halo is optionally replaced by Z; and $R^4$ is selected from the group consisting of $C_{2-5}$alkyl, aryl, heteroaryl, halo-$C_{1-4}$alkyl, halo-$C_{1-4}$alkyl-heteroaryl-, halo-$C_{1-4}$alkyl-heteroaryl$C_{1-4}$alkyl, halo-$C_{1-4}$alkyl-aryl - and halo-$C_{1-4}$alkyl-aryl$C_{1-4}$alkyl, wherein halo is optionally replaced by Z;

each $R^{10}$ is independently H or $C_{1-6}$alkyl; and
each $R^{11}$ is independently H or $C_{1-6}$alkyl,
or a pharmaceutically acceptable salt thereof.

23. The compound of claim 21, wherein A is H.
24. The compound of claim 22, wherein $R^3$ is H.
25. The compound of claim 23, wherein Y is OH.
26. The compound of claim 24, wherein $R^4$ is halo-$C_{1-4}$alkyl-heteroaryl-.
27. The compound of claim 21, that is

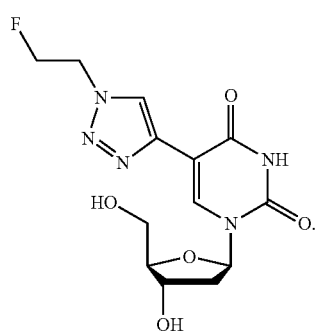

28. A compound of the Formula 1:

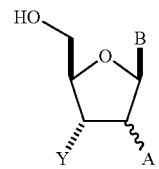

wherein B is

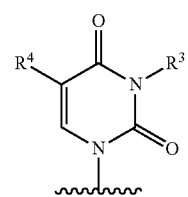

wherein:

A is Z or halo;

wherein each Z is independently a radionuclide selected from the group consisting of $^{11}$C, $^{18}$F, $^{123}$I, $^{124}$I, $^{125}$I, $^{131}$I and $^{77}$Br;

Y is OH or is $C_{1-4}$alkyl-aryl, $C_{1-4}$alkyl-heteroaryl, $C_{1-4}$alkoxy, $C_{3-6}$cycloalkoxy, $C_{3-12}$cycloalkyl$C_{1-5}$alkoxy, aryl, $C_{6-14}$aryloxy, $C_{6-10}$aryl$C_{1-4}$alkoxy, heteroaryl, heteroaryl$C_{1-4}$alkyl and heteroaryloxy;

$R^3$ is selected from the group consisting of halo-$C_{1-4}$alkyl, perhalo$C_{1-4}$alkyl, halo-$C_{1-4}$alkyl-aryl, halo-$C_{1-4}$alkyl-heteroaryl-$C_{1-4}$alkyl, halo-$C_{1-6}$alkylOC(O)CH($C_{1-5}$alkyl)-, $C_{1-5}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, heteroaryl$C_{1-3}$alkyl-heteroaryl$C_{1-3}$alkyl-, ($C_{1-6}$alkyl)$_2$NC(O)CH($C_{1-5}$alkyl)-, wherein halo is optionally replaced by Z; and $R^4$ is H or is $C_{1-10}$alkylenyl wherein at least one of the carbon atoms of the $C_{1-10}$alkylenyl is optionally replaced by a halo, Z, —O— and/or amino, cyano, hydroxy, oxo, thio and azido, or a pharmaceutically acceptable salt thereof.

29. The compound of claim 27, wherein Y is OH.
30. The compound of claim 28, wherein $R^3$ is CH$_2$—CH$_2$-halo.
31. A compound of the Formula 1:

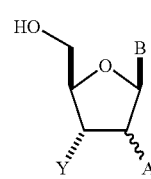

wherein B is

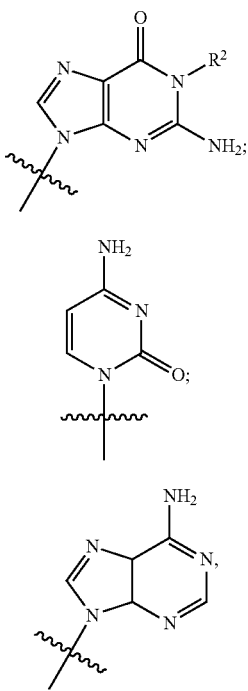

A is H, halo or hydroxy, or —O—X—Z, provided that when A is —O—X—Z, then Y is —O—$R^1$;

each X is a bond, or is independently a linker selected from the group consisting of:
  a) $C_{1-10}$alkylenyl wherein at least one of the $C_1$alkylenyl in the $C_{1-10}$alkylenyl group is optionally replaced by a —O—, —S—, —N($R^{10}$)—, —C(O)—, —C(S)—, —C(O)O—, —C(S)O—, —N($R^{10}$)C(O)—, —N($R^{10}$)C(S)—, —S(O)N($R^{10}$)— and —N($R^{10}$)S(O)$_2$ group;
  $C_{6-14}$arylenyl, $C_{1-3}$alkylenyl-arylenyl, $C_{1-3}$alkylenyl-aryl-$C_{1-3}$alkylenyl-aryl, $C_{3-6}$cycloalkylenyl, $C_{3-12}$cycloalkyl$C_{1-5}$alkylenyl, $C_{6-10}$aryl$C_{1-4}$alkylenyl, heteroarylenyl, —(CH$_2$CH$_2$O)$_{1-6}$C$_{1-3}$alkylenyl, $C_{1-3}$alkylenyl(OCH$_2$CH$_2$)$_{1-6}$O—, $C_{1-5}$alkylenyloxy, —CH$_2$CH$_2$O—, —CH$_2$CH$_2$—(OCH$_2$CH$_2$)$_{1-6}$O—, $C_{1-3}$alkylenyl-arylenyl-$C_{1-3}$alkylenyl, $C_{3-6}$cycloalkylenyloxy, $C_{3-12}$cycloalkylenyl$C_{1-5}$alkylenyloxy, $C_{1-3}$alkylenyl-heteroaryl-$C_{1-3}$alkylenyl-heteroaryl, heteroarylenyl$C_{2-5}$alkylenyloxy, $C_{6-14}$arylenyloxy, $C_{6-10}$arylenyl$C_{1-4}$alkylenyloxy and heteroarylenyloxy;
  wherein each $C_{6-14}$arylenyl, $C_{1-3}$alkylenyl-arylenyl, $C_{1-3}$alkylenyl-aryl-$C_{1-3}$alkylenyl-aryl, $C_{3-6}$cycloalkylenyl, $C_{3-12}$cycloalkyl$C_{1-5}$alkylenyl, $C_{6-10}$aryl$C_{1-4}$alkylenyl, heteroarylenyl, —(CH$_2$CH$_2$O)$_{1-6}$C$_{1-3}$alkylenyl, $C_{1-3}$alkylenyl(OCH$_2$CH$_2$)$_{1-6}$O—, $C_{1-5}$alkylenyloxy, $C_{1-3}$alkylenyl-arylenyl-$C_{1-3}$alkylenyl, $C_{3-6}$cycloalkylenyloxy, $C_{3-12}$cycloalkylenyl$C_{1-5}$alkylenyloxy, $C_{1-3}$alkylenyl-heteroaryl-$C_{1-3}$alkylenyl-heteroaryl, heteroarylenyl$C_{2-5}$alkylenyloxy, $C_{6-14}$arylenyloxy, $C_{6-10}$arylenyl$C_{1-4}$alkylenyloxy and heteroarylenyloxy is optionally substituted with one or two amino, halo, cyano, hydroxy, oxo, thio and azido group;
  b) —NH—(R)CHCOO—where R is an amino acid side chain; a peptide, a monosaccharide, disaccharide or oligosaccharide; or
  c) a combination of at least one of the groups in a) and one of the group in b); and Y is selected from the group consisting of hydroxy, fluoro, chloro, bromo, iodo, halo-$C_{1-4}$alkyl-aryl, halo-$C_{1-4}$alkyl-heteroaryl, halo-$C_{1-4}$alkoxy, perhalo$C_{1-4}$alkoxy, $C_{3-6}$cycloalkoxy, $C_{3-12}$cycloalkyl$C_{1-5}$alkoxy, aryl, $C_{6-14}$aryloxy, $C_{6-10}$aryl$C_{1-4}$alkoxy, heteroaryl, heteroaryl$C_{1-4}$alkyl and heteroaryloxy; or Y is —X—Z;

$R^1$ is H or is selected from the group consisting of halo-$C_{1-4}$alkyl, perhalo$C_{1-4}$alkyl, $C_{1-5}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl and heteroaryl; and $R^2$ is H or is selected from the group consisting of halo-$C_{1-4}$alkyl, perhalo$C_{1-4}$alkyl, $C_{1-5}$alkyl, $C_{3-6}$cycloalkyl, $C_{3-12}$cycloalkyl$C_{1-5}$alkyl, $C_{6-14}$aryl, $C_{6-10}$aryl$C_{1-4}$alkyl, heteroaryl, halo-$C_{1-4}$alkyl-aryl-$C_{1-4}$alkyl, halo-$C_{1-4}$alkyl-heteroaryl-$C_{1-4}$alkyl, ($C_{1-6}$alkyl)$_2$NC(O)CH($C_{1-5}$alkyl)-, halo-$C_{1-6}$alkylNR$^{11}$C(O)CH($C_{1-5}$alkyl)-, and halo-$C_{1-6}$alkylOC(O)CH($C_{1-5}$alkyl)-;

each $R^{10}$ is independently H or $C_{1-6}$alkyl; and
each $R^{11}$ is independently H or $C_{1-6}$alkyl;
wherein each Z is independently a radionuclide selected from the group consisting of $^{11}$C, $^{18}$F, $^{123}$I, $^{124}$I, $^{125}$I, $^{131}$I and $^{77}$Br,
or a pharmaceutically acceptable salt thereof.

\* \* \* \* \*